US011109800B2

(12) United States Patent
Hooven et al.

(10) Patent No.: US 11,109,800 B2
(45) Date of Patent: Sep. 7, 2021

(54) MEDICAL FLUID INJECTION APPARATUS AND METHOD WITH DETACHABLE PATCH AND MONITORING

(71) Applicant: Enable Injections, Inc., Cincinnati, OH (US)

(72) Inventors: Michael D. Hooven, Cincinnati, OH (US); Matthew J. Huddleston, Loveland, OH (US); David Stefanchik, Morrow, OH (US); Rowan Converse, Liberty Township, OH (US); Kory Gunnerson, Cincinnati, OH (US); James Marous, South Vienna, OH (US); Phillip Schultz, Covington, KY (US); Benjamin Webb, Cleves, OH (US)

(73) Assignee: ENABLE INJECTIONS, INC., Cincinnati, OH (US)

( * ) Notice: Subject to any disclaimer, the term of this patent is extended or adjusted under 35 U.S.C. 154(b) by 0 days.

(21) Appl. No.: 16/785,408

(22) Filed: Feb. 7, 2020

(65) Prior Publication Data
US 2020/0214625 A1    Jul. 9, 2020

Related U.S. Application Data

(63) Continuation of application No. PCT/US2019/069142, filed on Dec. 31, 2019.
(Continued)

(51) Int. Cl.
*A61M 5/00* (2006.01)
*A61B 5/00* (2006.01)
(Continued)

(52) U.S. Cl.
CPC .............. *A61B 5/4833* (2013.01); *A61B 5/01* (2013.01); *A61B 5/02042* (2013.01);
(Continued)

(58) Field of Classification Search
CPC ............ A61M 5/1723; A61M 5/14248; A61M 2005/1726; A61M 2005/14252;
(Continued)

(56) References Cited

U.S. PATENT DOCUMENTS

| 929,577    | A  | 7/1909  | Fry  |
| 7,637,891  | B2 | 12/2009 | Wall |

(Continued)

FOREIGN PATENT DOCUMENTS

| AU | 2003212260 B2 | 2/2008 |
| AU | 2009330321 B2 | 3/2013 |

(Continued)

OTHER PUBLICATIONS

PCT/US2019/069142 International Search Report and Written Opinion dated Apr. 29, 2020.
(Continued)

*Primary Examiner* — Nathan R Price
*Assistant Examiner* — Anh Bui
(74) *Attorney, Agent, or Firm* — Wilson Sonsini Goodrich & Rosati

(57) ABSTRACT

Provided herein are systems and methods for monitoring one or more health or physiological parameters in a subject. The systems and methods may comprise a patch coupled to an injector. Data may be transmitted to a mobile device or remote server, where the data may be processed. Processed data may be used to inform a subject on a health or physiological condition.

28 Claims, 72 Drawing Sheets

Related U.S. Application Data

(60) Provisional application No. 62/848,511, filed on May 15, 2019, provisional application No. 62/788,589, filed on Jan. 4, 2019.

(51) Int. Cl.

| | | |
|---|---|---|
| *A61B 5/01* | (2006.01) | |
| *A61B 5/02* | (2006.01) | |
| *A61B 5/024* | (2006.01) | |
| *A61M 5/142* | (2006.01) | |
| *A61M 5/31* | (2006.01) | |
| *A61M 5/315* | (2006.01) | |
| *A61M 5/20* | (2006.01) | |

(52) U.S. Cl.
CPC .......... *A61B 5/02438* (2013.01); *A61B 5/444* (2013.01); *A61M 5/14248* (2013.01); *A61M 5/20* (2013.01); *A61M 5/31* (2013.01); *A61M 5/3158* (2013.01); *A61M 5/31568* (2013.01); *A61B 2562/08* (2013.01); *A61M 2205/18* (2013.01); *A61M 2205/3584* (2013.01); *A61M 2205/3592* (2013.01); *A61M 2205/581* (2013.01); *A61M 2205/582* (2013.01); *A61M 2205/583* (2013.01); *A61M 2205/584* (2013.01); *A61M 2205/6054* (2013.01)

(58) Field of Classification Search
CPC ........... A61M 2005/14256; A61M 2005/1426; A61M 2205/581; A61M 2205/582; A61M 2205/583

See application file for complete search history.

(56) References Cited

U.S. PATENT DOCUMENTS

| | | |
|---|---|---|
| 7,713,238 B2 | 5/2010 | Mernoe |
| 8,277,435 B2 | 10/2012 | Estes |
| 8,382,700 B2 | 2/2013 | Straessler et al. |
| 8,414,532 B2 | 4/2013 | Brandt et al. |
| 8,784,380 B2 | 7/2014 | Wall |
| 8,801,611 B2 | 8/2014 | Brister et al. |
| 9,741,139 B2 | 8/2017 | Kamath et al. |
| 9,925,333 B2 | 3/2018 | Hooven et al. |
| 10,117,993 B2 | 11/2018 | Estes et al. |
| 2004/0116847 A1* | 6/2004 | Wall ................ A61M 5/2033 604/93.01 |
| 2006/0253086 A1 | 11/2006 | Moberg et al. |
| 2008/0215035 A1* | 9/2008 | Yodfat ................ A61M 5/158 604/513 |
| 2008/0269687 A1* | 10/2008 | Chong ................ A61L 27/28 604/180 |
| 2014/0276414 A1* | 9/2014 | Baker ................ A61M 5/1456 604/135 |
| 2014/0324021 A1 | 10/2014 | Ulrich et al. |
| 2016/0089056 A1 | 3/2016 | Limaye et al. |
| 2016/0296699 A1 | 10/2016 | Cabiri |
| 2017/0173261 A1 | 6/2017 | O'Connor et al. |
| 2017/0196771 A1 | 7/2017 | Hooven et al. |
| 2017/0259015 A1* | 9/2017 | Caspers ............ A61M 5/14248 |
| 2018/0161491 A1 | 6/2018 | Sanders et al. |
| 2018/0200430 A1* | 7/2018 | Vazquez ................ A61M 5/142 |
| 2019/0282756 A1* | 9/2019 | Hanson ................ A61M 5/1684 |

FOREIGN PATENT DOCUMENTS

| | | |
|---|---|---|
| CA | 2346639 C | 8/2008 |
| EP | 1624913 B1 | 7/2010 |
| EP | 1881859 B1 | 1/2011 |
| JP | 5113847 B2 | 1/2013 |
| KR | 100853949 B1 | 8/2008 |
| WO | WO-2017091624 A1 | 6/2017 |
| WO | WO-2017189707 A1 | 11/2017 |
| WO | WO-2018218082 A1 | 11/2018 |
| WO | WO-2018218128 A1 | 11/2018 |
| WO | WO-2019036181 A1 | 2/2019 |
| WO | WO-2019038751 A1 | 2/2019 |
| WO | WO-2019040118 A1 | 2/2019 |
| WO | WO-2019040313 A1 | 2/2019 |
| WO | WO-2019046436 A1 | 3/2019 |
| WO | WO-2020142544 A1 | 7/2020 |

OTHER PUBLICATIONS

PCT/US2019/069142 Invitation to Pay Additional Fees dated Mar. 4, 2020.

* cited by examiner

Enable Compliance Monitoring

- Provide real-time monitoring of patient adherence/compliance
    - User Identification
    - Device Identification
    - Different states of transfer package/device
    - When dose has started
    - When dose is complete
    - User feedback/progress

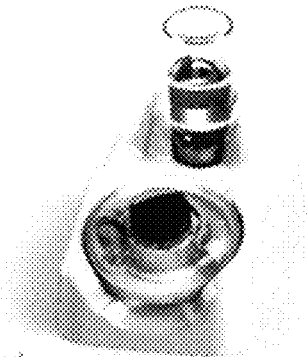

Compliance monitoring and transmission electronics can be incorporated into both the transfer package and device to provide necessary information

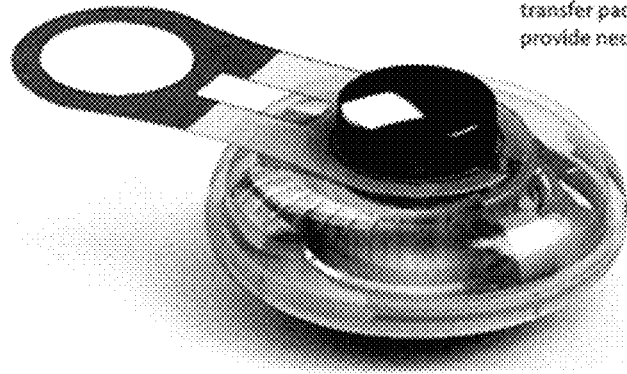

Figure 50

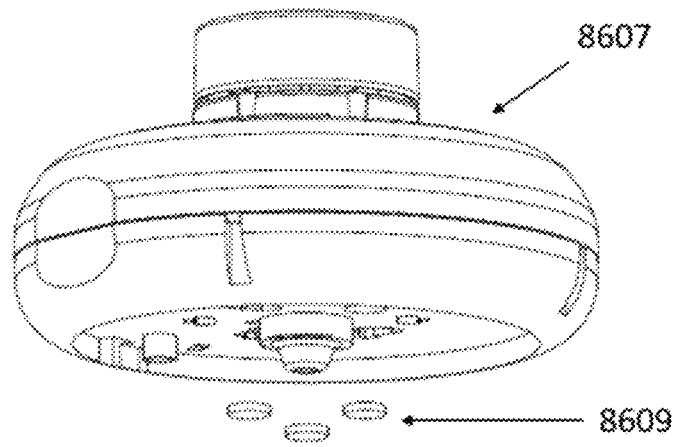
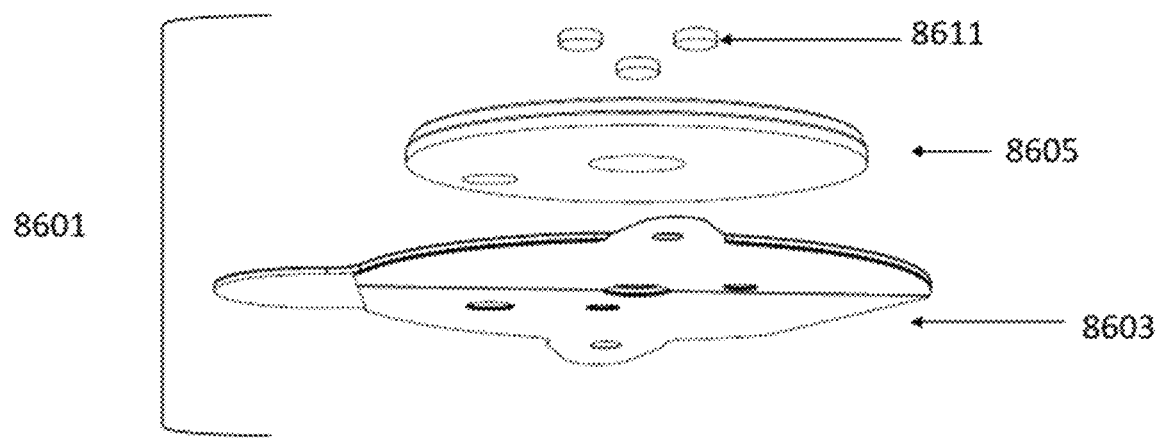
Figure 86

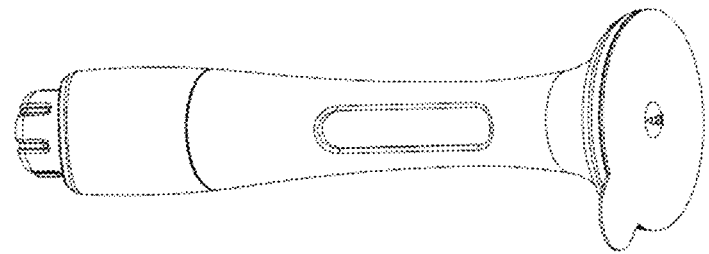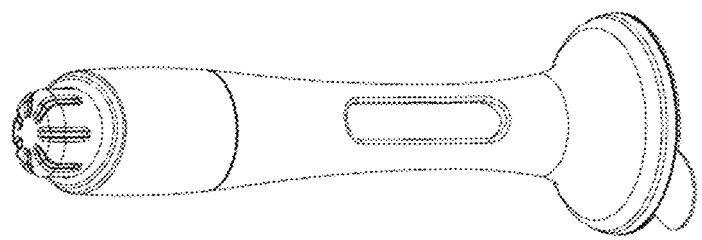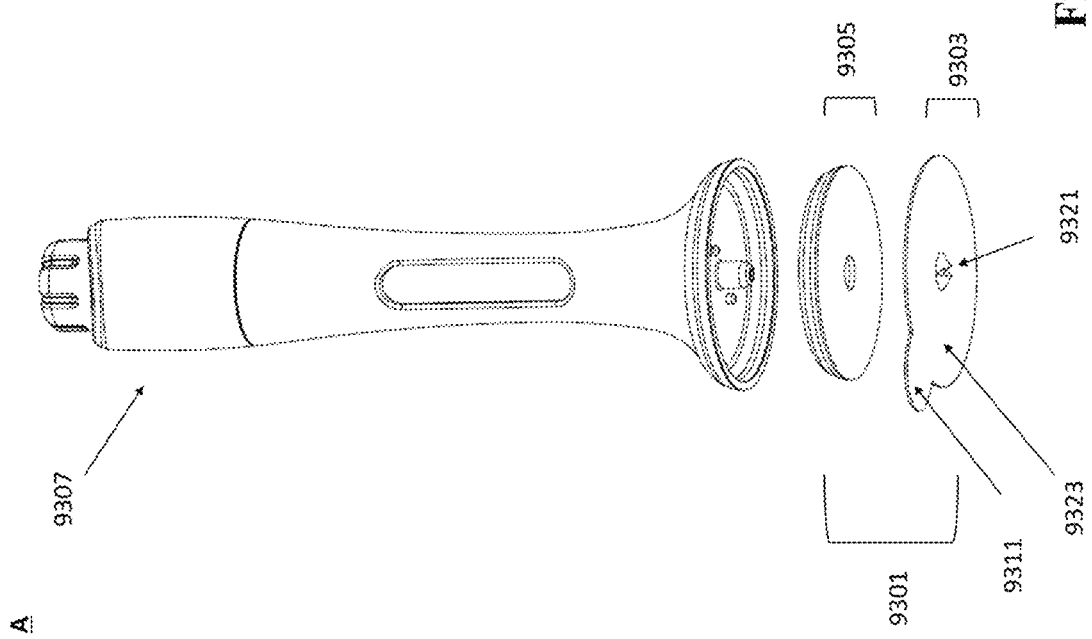
Figure 93

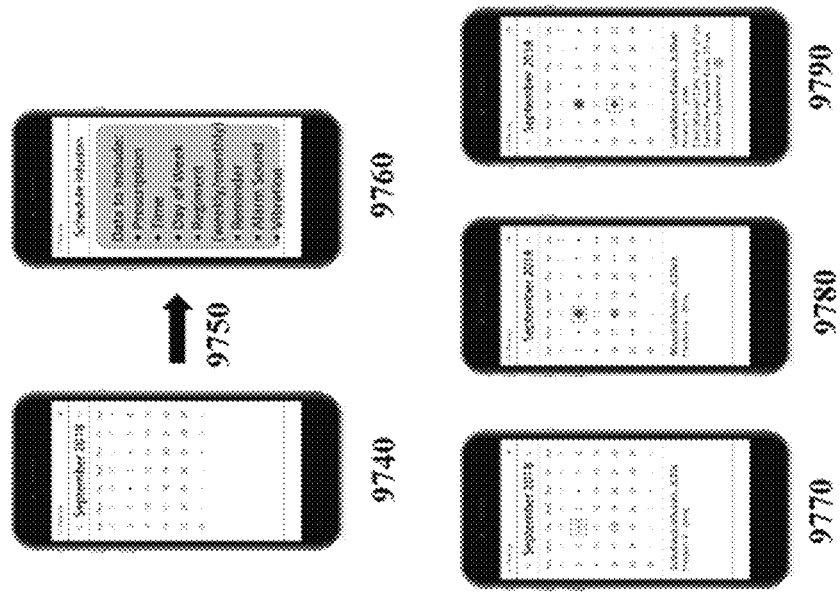
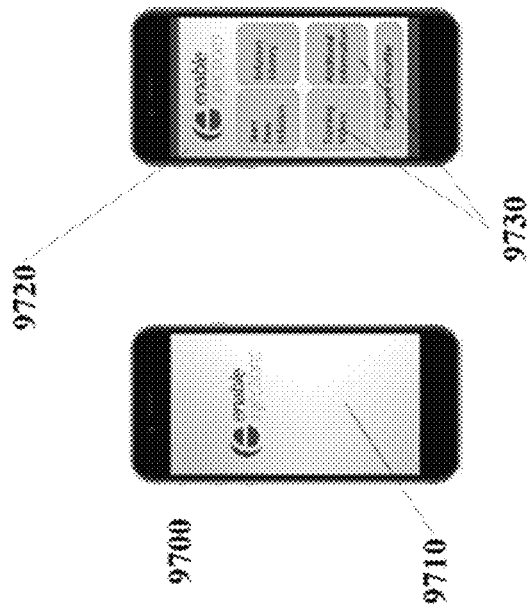
Figure 97

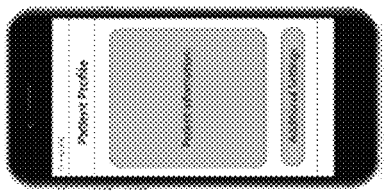
FIG. 99C
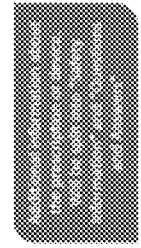
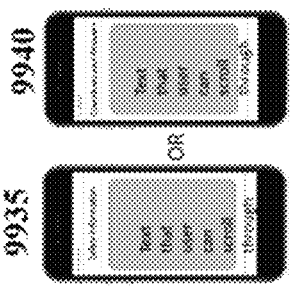
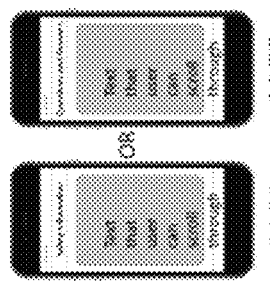
FIG. 99B
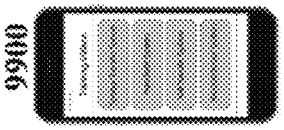
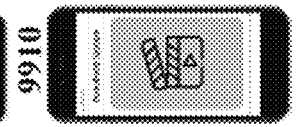
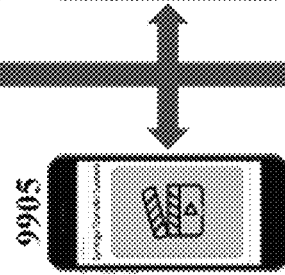
FIG. 99A
Figure 99

MEDICAL FLUID INJECTION APPARATUS AND METHOD WITH DETACHABLE PATCH AND MONITORING

CROSS-REFERENCE

This application is a continuation of International Patent Application No. PCT/US2019/069142, filed on Dec. 31, 2019, which claims priority to U.S. Provisional Patent Application Nos. 62/848,511, filed May 15, 2019, and U.S. Provisional Patent Application No. 62/788,589, filed Jan. 4, 2019, each of which is entirely incorporated herein by reference.

BACKGROUND

Vials are one of the preferred reservoirs or container closure systems used by the pharmaceutical industry due to their extensive clinical history and record of long-term stability with a wide variety of drugs. Pharmaceutical drugs including biologics are provided in standard containers such as vials. Additionally, the industry has made a significant investment in capital equipment for aseptic vial filling. However, vials require the transfer of the contained drug from the vial to an injection device (e.g., injector, autoinjector, infuser, etc.) for delivery to the patient. New container closure systems such as prefilled syringes and cartridges have been introduced that allow direct transfer of the drug from the syringe or cartridge to the patient. Injection devices such as auto-injectors and pens have been developed to utilize these newer forms of container closure. Because of uncertainty about long-term drug stability, and the extensive manufacturing resources already in place, devices that incorporate standard container closure systems such as vials, prefilled syringes or cartridges are greatly preferred by the pharmaceutical industry over devices that require a custom form of drug containment.

However, vials, prefilled syringes and cartridges are not necessarily the optimum containers for a drug delivery device. This is especially true in the case of delivery devices that deliver relatively high volumes of drugs (2-50 cc) or high viscosity (over 15 cP and up to about 100 cP). Vials, prefilled syringes, and cartridges are almost exclusively cylinders made of glass, which imposes design constraints on forces and geometries. Typical syringes and auto-injectors are limited on the viscosities of drug that can be delivered as well as by the forces that can be applied to the glass container closure systems. New injection devices have been developed including pumps for the delivery of insulin that use custom container closures, but these systems are very expensive, cannot generate high forces or pressures and typically reusable and/or refillable.

On-body injection devices have been the subject of continuing development in efforts to develop injection devices and methods that offer benefits such as greater comfort and less pain while providing effective subcutaneous injection.

SUMMARY

Recognized herein is a need for new and/or improved apparatuses, systems and methods for injection of medicaments (e.g., drugs) from a reservoir, e.g., source vial or vials, to and into a subject. Further, recognized herein is a need for apparatuses, systems, and methods for monitoring a health or physiologic parameter prior to, during, and/or following injection of a medicament into a subject. Such an apparatus or system may be useful, for example, in regulatory procedures and patient monitoring.

The present disclosure provides apparatuses, systems, and methods that may be used for medical fluid transfer and injection, and methods for administering a substance (e.g., medicament) to a subject and monitoring the subject for one or more physical parameters or attributes before, during and/or after the administration of the substance.

In an aspect, provided herein is a system for measuring a health or physiological parameter from a subject, comprising: (a) a patch comprising a first housing having a sensor configured to: (i) measure said health or physiological parameter from said subject when said patch is secured to a body of said subject, and (ii) provide one or more outputs corresponding to said health or physiological parameter from said subject, wherein said first housing comprises an opening; and an injector having a second housing comprising a cannula in fluid communication with a fluid flow path, wherein said second housing is coupled to said first housing such that said cannula is directed through said opening and in contact with a body of said subject when said patch is secured to said body, wherein said injector is configured to (i) direct a substance from a reservoir to said fluid flow path in fluid communication with said reservoir, and (ii) direct said substance from said fluid flow path into said subject through said cannula.

In some embodiments, the system further comprises a pump integrated with the cannula, wherein the pump is configured to direct the substance from the fluid flow path into the subject through the cannula. In some embodiments, the cannula is configured to extend towards or retract away from the body of the subject. In some embodiments, the opening comprises a pierce-able membrane. In some embodiments, the pierce-able membrane is pierced by the cannula to generate the opening. In some embodiments, the reservoir is secured to the injector. In some embodiments, the reservoir is removable from the injector. In some embodiments, the reservoir is part of the injector. In some embodiments, the substance is a medicament. In some embodiments, the medicament is for treating one or more diseases selected from the group of cardiovascular, musculoskeletal, gastrointestinal, dermatology, immunology, ophthalmology, hematology, neurology, oncology, endocrinology, metabolic and respiratory disease. In some embodiments, the injector comprises the reservoir, wherein the reservoir is configured to contain a formulation having the substance. In some embodiments, the first housing is removably coupled to the second housing. In some embodiments, the patch comprises a communication interface for transmitting data corresponding to the plurality of health or physiological parameters to an electronic device in communication with the communication interface. In some embodiments, the communication interface comprises a wireless communication interface. In some embodiments, the communication interface comprises a Wi-Fi interface. In some embodiments, the communication interface comprises a near field communication interface. In some embodiments, the communication interface comprises a Bluetooth interface. In some embodiments, the communication interface comprises an optical wireless interface. In some embodiments, the communication interface comprises a direct electrical contact digital or analog interface. In some embodiments, an input transducer/sensor of the plurality of sensors is selected from the group consisting of a conductivity sensor, impedance sensor, capacitance sensor, charge sensor, humidity sensor, temperature sensor, heart rate sensor, interstitial pressure sensor, resistance sensor, optical sensor, distension sensor, acoustic sensor, vibration sensor, blood pressure sensor, color sensor, chemical sensor, and a substance-tracking sensor. In some embodiments, the system further comprises a second sensor, wherein the second sensor is configured to measure one or more device parameters chosen from the group consisting of: a dosage of the substance that is administered, a flow rate of dispensing of the substance, a volume of the substance that is administered, an occlusion of the cannula, and contact of the cannula into the body of the subject. In some embodiments, the patch or the injector comprises the second sensor. In some embodiments, the patch further comprises one or more transducers. In some embodiments, the one or more transducers is configured to generate an output signal, wherein the output signal comprises a vibration signal, audio signal, or visual signal. In some embodiments, an output transducer of the plurality of transducers is selected from the group consisting of a haptic(vibration) transducer, audio transducer, visual transducer, and direct electrical stimulation (e.g. transcutaneous electrical nerve stimulation/TENS).

In another aspect, disclosed herein is a method for measuring a plurality of health or physiological parameters from a subject, comprising: (a) providing: (i) a patch comprising a first housing having a plurality of sensors and comprising an opening, and (ii) an injector having a second housing comprising a cannula in fluid communication with a fluid flow path, wherein the second housing is coupled to the first housing of the patch, and wherein the injector comprises a reservoir comprising a substance and a fluid flow path in fluid communication with the reservoir; (b) securing the patch to a body of the subject; (c) when the patch is secured to the body of the subject, directing the cannula through the opening to (i) direct the substance from the reservoir to the fluid flow path, and (ii) direct the substance from the fluid flow path into the subject through the cannula; and (d) using the plurality of sensors to (i) measure the plurality of health or physiological parameters from the subject, and (ii) provide one or more outputs corresponding to the plurality of health or physiological parameters from the subject.

In some embodiments, the method further comprises using a pump integrated with the cannula to direct the substance from the fluid flow path into the subject through the cannula. In some embodiments, the cannula is configured to extend towards or retract away from the body of the subject. In some embodiments, the opening comprises a pierce-able membrane. In some embodiments, the pierce-able membrane is pierced by the cannula to generate the opening. In some embodiments, the reservoir is secured to the injector. In some embodiments, the reservoir is removable from the injector. In some embodiments, the reservoir is part of the injector. In some embodiments, the substance is a medicament. In some embodiments, the medicament is used for treating one or more diseases selected from the group of cardiovascular, musculoskeletal, gastrointestinal, dermatology, immunology, ophthalmology, hematology, neuroscience, oncology, endocrinology, metabolic and respiratory disease. In some embodiments, the injector comprises the reservoir, wherein the reservoir is configured to contain a formulation having the substance. In some embodiments, the first housing is removably coupled to the second housing. In some embodiments, the patch comprises a communication interface for transmitting data corresponding to the plurality of health or physiological parameters to an electronic device in communication with the communication interface. In some embodiments, the communication interface is a wireless communication interface. In some embodiments, the communication interface is a Wi-Fi interface. In some embodiments, the communication interface is a near field communication interface. In some embodiments, the communication interface is a Bluetooth interface. In some embodiments, the communication interface is an optical wireless interface. In some embodiments, an input transducer/sensor of the plurality of sensors is selected from the group consisting of a conductivity sensor, impedance sensor, capacitance sensor, charge sensor, humidity sensor, temperature sensor, heart rate sensor, interstitial pressure sensor, resistance sensor, distension sensor, acoustic sensor, vibration sensor, blood pressure sensor, color sensor, chemical sensor, and a substance-tracking sensor. In some embodiments, an output transducer of the plurality of transducers is selected from the group consisting of a haptic(vibration) transducer, audio transducer visual transducers, and direct electrical stimulation (e.g. transcutaneous electrical nerve stimulation/TENS).

In some embodiments, a second sensor of the plurality of sensors is selected from the group consisting of temperature sensor, humidity sensor, flow rate sensor, button position sensor, vibration sensor, audible sensor, skin sensor.

In yet another aspect, provided herein is an injector comprising; (a) a housing; (b) a medicament reservoir provided in the housing; (c) an injection cannula moveable within the housing between a pre-dispense position and a dispense position in fluid communication with the reservoir; (d) an injector transducer/sensor mounted on or within the housing; (e) a skin attachment layer attached to the housing, the skin attachment layer including an adhesive configured to secure the housing to a user's skin with a first holding force; (f) a patch removably secured to the housing with a second holding force, the patch including a sensor adhesive layer configured to secure the patch to a user's skin with a third holding force, a patch input transducer/sensor, output transducer and circuitry configured to receive data from the injector transducer/sensor and the patch transducer/sensor and transmit received data to a remote receiver; (g) wherein the third holding force is greater than the second holding force.

In some embodiments, the second holding force is greater than the first holding force and the patch is removably attached to the skin attachment layer. In some embodiments, the patch is removably attached to the skin attachment layer by perforations. In some embodiments, the patch is removably secured to the housing by a magnet. In some embodiments, a magnet is positioned within or on the housing of the injector and the patch includes a metallic portion configured to be engaged by the magnet. In some embodiments, the skin attachment layer includes an opening and the patch is positioned within the opening when it is removably secured to the housing of the injector. In some embodiments, the opening is centrally located in the skin attachment layer and the injection cannula of the injector passes through the opening of the skin attachment layer and an orifice of the patch when in the dispense position. In some embodiments, the patch includes an extension including the orifice through which the injection cannula of the injector passes when in the dispense position, the extension configured to compress a user's skin around an injection site. In some embodiments, the patch includes a printed circuit board upon which the circuitry is positioned and to which the sensor adhesive layer and the patch transducer/sensor are attached, the sensor adhesive layer including a central window through which the extension passes.

In some embodiments, the extension is generally conical shaped. In some embodiments, the patch includes a printed circuit board upon which the circuitry is positioned and to which the sensor adhesive layer and the patch sensor are attached. In some embodiments, the circuitry of the patch includes a microcontroller/microprocessor and a transmitter. In some embodiments, the sensor of the injector includes a transmitter and the circuitry of the patch further includes a receiver through which data is received from the injector transducers/sensors by wireless transmission and through which data is sent to transducers through wireless transmission. In some embodiments, the microcontroller/microprocessor, transmitter and receiver are combined into a single component. In some embodiments, the injector further comprises a wire connection between the injector transducers/sensor and the circuitry of the patch, the wire connection configured to disconnect as or after the injector is removed from the patient. In some embodiments, the microcontroller/microprocessor and the transmitter are combined into a single component. In some embodiments, the transmitter is a Bluetooth transmitter. In some embodiments, the injector sensor includes a plurality of input transducers/sensors and output transducers. In some embodiments, the patch sensor includes a plurality of input transducers/sensors and output transducers. In some embodiments, the patch sensor includes a plurality of either input transducers/sensors and output transducers.

In yet another aspect, provided herein is a method for collecting data from an injector and a patient comprising (a) attaching an injector including an injector sensor and a patch including a patch sensor, output transducers and circuitry to the patient; (b) receiving data from the injector sensor and the patch sensor using the patch circuitry; (c) transmitting the received data to a remote receiver using the patch circuitry; (d) removing the injector from the patient; (e) receiving additional data from the injector sensor using the patch circuitry after removal of the injector from the patient; and (f) transmitting the additional received data to a remote receiver using the patch circuitry.

In some embodiments, the injector and the patch are attached to the patient simultaneously. In some embodiments, (a) includes attaching the patch before the injector and, before attaching the injector to the patient, further comprising the steps of receiving data from the patch sensor using the patch circuitry transmitting the received data to a remote receiver using the patch circuitry. In some embodiments, the data collected from the patient includes measurable attributes that may be affected by a drug administered by the injector and/or injection of the drug using the injector. In some embodiments, the data collected from the patient includes measurable attributes that may affect or are indicators of the safety and/or efficacy of a drug administered by the injector and/or use of the injection.

In yet another aspect, provided herein is a method for monitoring an injection site of a patient for an injection site reaction comprising the steps of: (a) attaching an injector including a patch including a patch sensor and circuitry to the patient, where the patch sensor includes a skin temperature transducer/sensor and a skin color monitor; (b) receiving data from patch sensor using the patch circuitry; (c) transmitting the received data to a remote receiver using the patch circuitry, wherein the data includes an indication of temperature rise or change in skin color so that an injection site reaction may be identified.

In another aspect, disclosed herein is an injector comprising (a) a housing; (b) a medicament reservoir provided in the housing; (c) an injection cannula moveable within the housing between a pre-dispense position and a dispense position in fluid communication with the reservoir; (d) a patch sensor configured to receive and transmit data, the patch sensor removably secured to the housing with a first holding force; (e) an attachment layer attached to the patch sensor, the attachment layer including an adhesive configured to secure the patch sensor to a user's skin with a second holding force; (f) wherein the second holding force is greater than the first holding force so that the patch sensor remains attached to the user's skin as the housing is removed from the patch sensor.

In some embodiments, the body of the subject is skin. In some embodiments, the patch is configured to receive data from the injector. In some embodiments, the data is used to adjust a device parameter of the patch or the injector. In some embodiments, the device parameter comprises one or more device parameters selected from the group consisting of a dosage of the substance that is administered by the injector, a flow rate of dispensing of the substance of the injector, and a volume of the substance that is administered by the injector. In some embodiments, the data is used to generate a notification to the subject via a transducer. In some embodiments, the notification comprises one or more notifications selected from the group consisting of: a vibration, a sound, direct electrical stimulation, and a visual indicator.

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

The present subject matter includes a transfer device and/or an injector of any suitable detailed construction but transfer and injectors that are particularly useful in combination with the apparatus here are described in U.S. Pat. No. 9,925,333, the contents of which are hereby incorporated by reference herein.

In an aspect, an injector includes a housing. A medicament reservoir is provided in the housing and an injection cannula is moveable within the housing between a pre-dispense position and a dispense position in fluid communication with the reservoir. An injector sensor is mounted on or within the housing. A skin attachment layer is attached to the housing and includes an adhesive configured to secure the housing to a user's skin with a first holding force. A patch is removably secured to the housing with a second holding force and includes a sensor adhesive layer configured to secure the patch to a user's skin with a third holding force. The third holding force is greater than the second holding force. The patch also includes a patch sensor and circuitry configured to receive data from the injector sensor and the patch sensor and transmit received data to a remote receiver.

In another aspect, a process is provided for collecting data from an injector and a patient includes the steps of: attaching an injector including an injector sensor and a patch including a patch sensor and circuitry to the patient; receiving data from the injector sensor and the patch sensor using the patch circuitry; transmitting the received data to a remote receiver using the patch circuitry; removing the injector from the patient; receiving additional data from the injector sensor using the patch circuitry after removal of the injector from the patient; and transmitting the additional received data to a remote receiver using the patch circuitry.

In still another aspect, a process for monitoring an injection site of a patient for an injection site reaction includes the steps of: attaching an injector including a patch including a patch sensor and circuitry to the patient, where the patch sensor includes a skin temperature sensor and a skin color monitor; receiving data from patch sensor using the patch circuitry; and transmitting the received data to a remote receiver using the patch circuitry, wherein the data includes an indication of temperature rise or change in skin color so that an injection site reaction may be identified.

In still another aspect, an injector includes a housing with a medicament reservoir provided in the housing. An injection cannula is moveable within the housing between a pre-dispense position and a dispense position in fluid communication with the reservoir. A patch sensor configured to receive and transmit data is removably secured to the housing with a first holding force. A skin attachment layer is attached to the patch sensor and is configured to secure the patch sensor to a user's skin with a second holding force, where the second holding force is greater than the first holding force.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" herein), of which:

FIG. 50 further depicts a compliance monitoring system.

FIG. 86 shows a schematic of another example of an injector coupled to a patch.

FIG. 93 shows a schematic of an example patch with a pierceable membrane configured to couple to an autoinjector.

FIG. 97 schematically illustrates an example workflow of a mobile application.

FIG. 99 schematically illustrates another example workflow of a mobile application. FIG. 99A shows a schematic. FIG. 99B shows another schematic. FIG. 99C shows yet another schematic.

DETAILED DESCRIPTION

Figure 1:
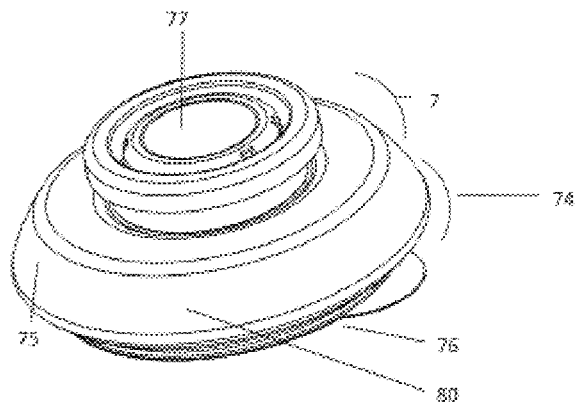
FIG. 1 shows a perspective view of an injector.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "subject," as used herein, generally refers to a user of a device, system, or method of the present disclosure, or an individual on which a device, system, or method of the present disclosure is being used. The subject may be a patient (e.g., a patient that is being treated or monitored by a physician or healthcare provider). As an alternative, the subject may not be a patient. The subject may have or be suspected of having a disease or disorder. As an alternative, the subject may be asymptomatic with respect to a disease or disorder. The subject may be a vertebrate, a mammal (e.g., human or animal), a non-human primate, etc. The subject may be an animal, such as a rodent (e.g., rat or mouse), a canine (e.g., dog), a feline (e.g., cat), a bovine, or other animal.

The term "medicament," as used herein, generally refers to a substance that is used for treating a health or physiological state or condition of a subject (e.g., medical treatment). The medicament may be a drug or therapeutic agent. The medicament may be a solid, liquid, gas, or combinations thereof. The medicament may be an aerosol, pill, tablet, capsule, pastille, elixir, emulsion, effervescent powder, solution, suspension, tincture, liquid, gel, dry powder, vapor, droplet, ointment, or a combination or variation thereof. A medicament may be used to treat an illness, ailment, or disease, or may be used as a health supplement (e.g., vitamins, minerals, probiotics, etc.).

The present disclosure provides devices, methods and systems for delivering a substance (e.g., a medicament) to a subject and monitoring the subject prior to, concurrently with and/or subsequent to delivering the substance. A device of the disclosure may be an injector that delivers the medicament. Alternatively, or in addition to, the device may be a patch that is configured to monitor the subject and/or communicate with the injector. In some examples, the injector and patch are separate devices (e.g., separable from each other). As an alternative, the injector and patch may be part of single device (e.g., not separable from each other).

Injector

Referring to FIG. 1, the injector 7 may be of any suitable configuration. As explained earlier, the injector may advantageously employ one or more of the features of the injectors described in U.S. Pat. No. 9,925,333, the contents of which are hereby incorporated by reference herein.

Figure 2:
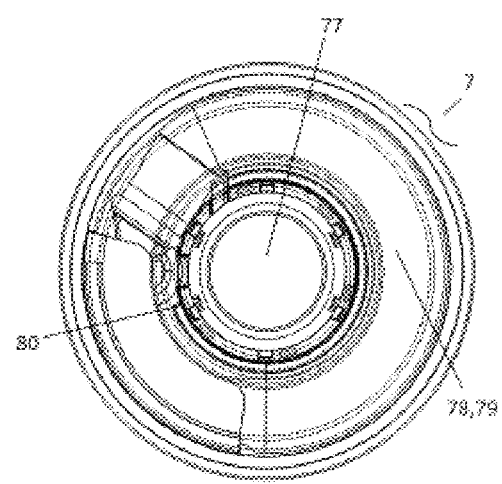
FIG. 2 shows a top view of a filled injector showing the delivery indicator in a full state.
Figure 3:
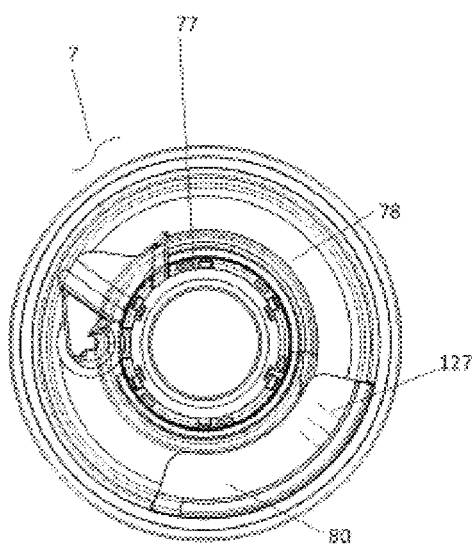
FIG. 3 shows top view of a filled injector showing the delivery indicator in an empty state.

Referring to FIGS. 1-3, the injector 7 has a generally low-profile, disc-shaped outer housing 74 with an upper surface 75 and a lower surface 76, through which a cannula or needle protrudes when actuated by the user. The upper surface 75 has an actuator or button 77 to start the injection and a section 80 of the housing 74 that allows the subject or medical professional to view the expandable member 78 to ascertain the amount of a substance 79, e.g., injectable fluid or medicament, in the in a reservoir of injector 7. In such cases, the section 80 of the housing may comprise a transparent material, and the user could determine whether the injection has commenced or concluded. In some cases, the expandable member 78 and/or the section 80 of the housing 74 may be graduated, such as by demarcations 127 or the like, so that the subject or a medical professional can visually determine the amount of substance 79 remaining with greater precision—such as, for example, about 50% complete or about 75% complete. In addition, the expandable member 78 may itself include or interact with a feature on the outer housing 74 to show the amount of substance 79 remaining in the reservoir of the injector. For example, when the injector 7 is full of substance 79, the clear section 80 may show one color such as but not limited to green. When the injector 7 is empty of substance 79, the clear section 80 may show a different color such as but not limited to red. In the middle of dispense, the clear section 80 could show a combination of colors.

Figure 4:
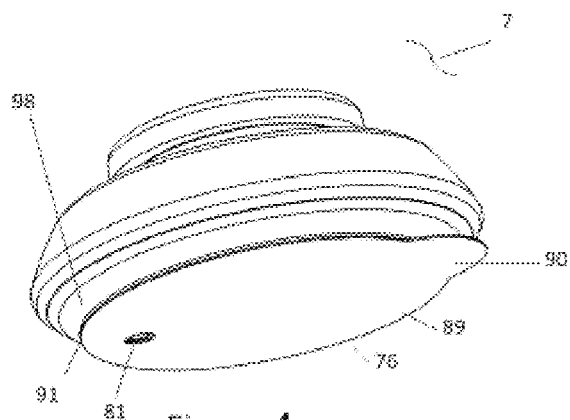
FIG. 4 shows a perspective view showing the underside of the injector with attached tape and fill port.
Figure 5:
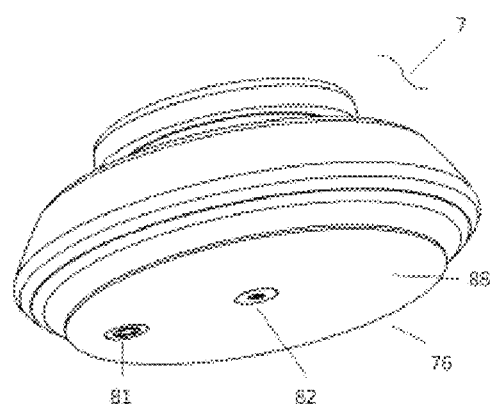
FIG. 5 shows a perspective view showing the underside of the injector with tape detached and the fill and dispense ports exposed.
Figure 6:
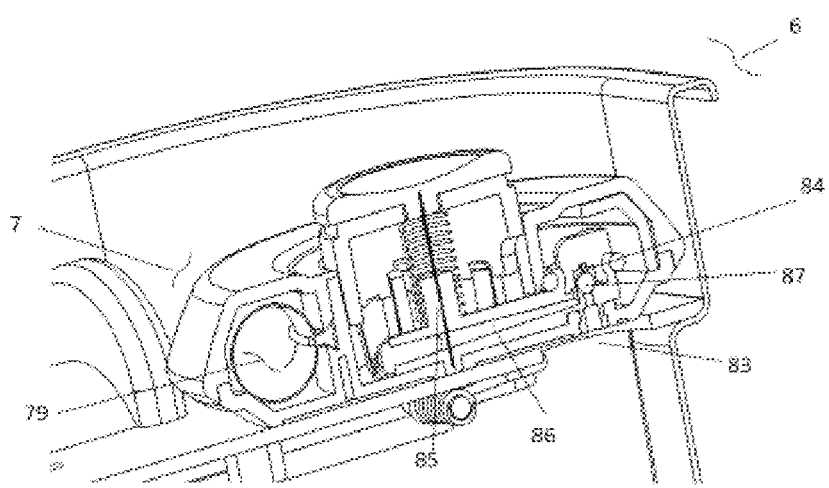
FIG. 6 shows a cross-section of the injector on the transfer apparatus.

Referring to FIGS. 4-6, the undersurface 76 of the injector 7 includes a filling port 81 and a dispense port 82. The filling port 81 is the interface that allows the transfer apparatus filling tube 83 to transfer substance 79 to the injector 7 (e.g., a reservoir of the injector). The dispense port 82 also contains an internal pathway 84 between the expelled substance 79 from the expandable member 78 and the cannula 85. The filling port 81 and dispense port 82 may be in direct fluid communication through internal pathways 86, or they may be combined into a single port.

Referring to FIGS. 4-6, the injector may include a filling port 81 that includes a check valve 87 to prevent pressurized substance 79 from leaking out of the injector 7 when the injector 7 is removed from the transfer apparatus 6 and the filling port 81 is removed from the filling tube 83.

Referring to FIGS. 4-6, the injector 7 may also have a filling port 81 that is configured to accept the insertion of a syringe. This syringe may be configured with a luer fitting or a cannula. This filling port 81 configuration allows for the manual filling of the injector by the user. The transfer apparatus 6 may still be used but would not be required in this configuration.

Referring to FIGS. 4-26, the injector 7 may also have a dispense port 82 that is configured to directly connect to a cannula via attached tubing or a standard cannula port.

Referring to FIGS. 4-6, the undersurface 76 of the injector 7 carries an adhesive 88 for securing the injector 7 temporarily to a body (e.g., the skin) of a subject until the injection is complete. During removal of the injector 7, an adhesive tape liner 89 may be removed automatically exposing an adhesive surface 88 on the undersurface 76 of the injector 7 that may be used to adhere the injector 7 to the patient's body (e.g., skin). Alternatively, the tape liner 89 may have a tab 90 that the user pulls to manually remove before adhering the injector 7 to the skin. Alternatively this tab may be attached to the surface of the transfer device 4 so that the tape liner is automatically removed upon removal of the injector 7.

Referring to FIGS. 4-6, the injector 7 may have an adhesive tape flange 91 that extends beyond the undersurface base 76. This flange 91 of adhesive tape 88 can act as a strain relief between the injector 7 and skin surface, reducing the risk of accidentally dislodging the injector 7 from the skin. In other words, similar to a tapered strain relief on a wire where it enters into a connector, the extended adhesive flange 91 acts to distribute the load on both sides of the connection point between the adhesive tape 88 and the undersurface base 76 of the injector 7 to reduce any stress risers at the adhesive tape 88 and skin interface.

Referring to FIGS. 4-6, the injector 7 may be configured with a tapered underside surface 98 that presses on the adhesive flange 91 to securely attach the adhesive tape 88 to the skin as the user is securing the injector 7 to the skin without additional user intervention. By using the compliance of a person's skin when pressing the injector 7 against the skin, the tapered underside surface 98 of the injector 7 effectively presses the flange 91 of the adhesive tape 88 against the skin but the upper exposed surface of the flange 91 portion does not have exposed adhesive and therefore is not attached to that portion of the tapered underside surface 98. The user is not required to run their finger around the flange 91 to secure the injector 7 to the skin making it a much simpler method of adhesive tape 88 attachment.

Referring to FIGS. 4-6, the injector 7 may have an underside surface 76 that is flexible or compliant in lieu of being rigid to allow for improved attachment by conforming of the injector 7 to the skin during application.

Figure 7:
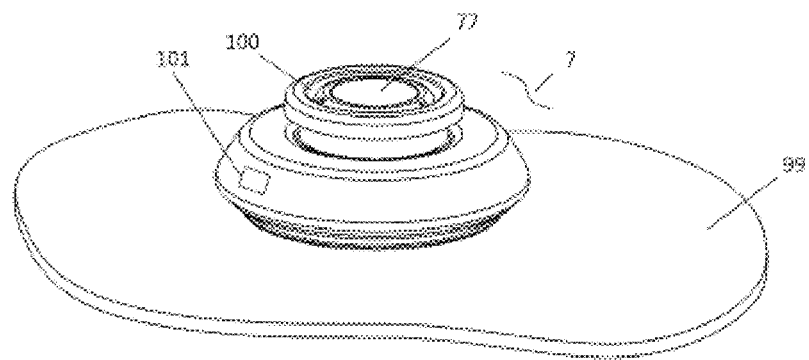
FIG. 7 shows a perspective view of the injector attached to the body (e.g., skin) with the safety device installed.
Figure 8:
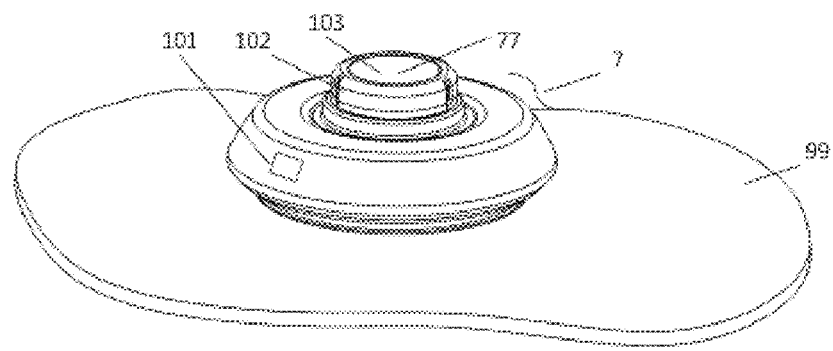
FIG. 8 shows a perspective view of the injector attached to the body (e.g., skin) with the safety device removed and the button up in a pre-fire state.
Figure 9:
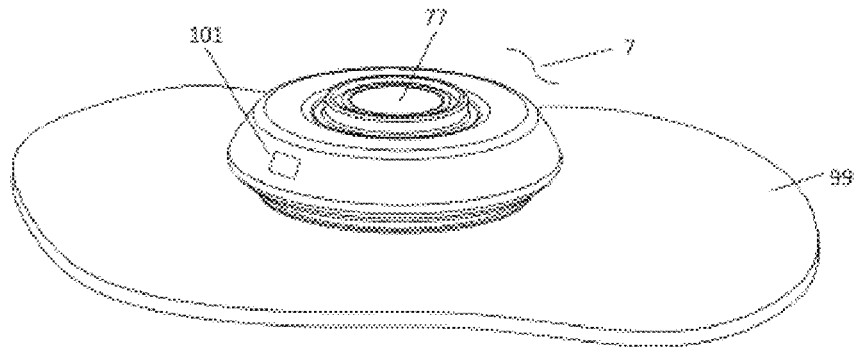
FIG. 9 shows a perspective view of the injector attached to the body (e.g., skin) with the safety device removed and the button down in a fired state.

Referring to FIGS. 7-9, after the injector 7 is placed against or adhered to the body (e.g., skin) 99 of the subject, a safety mechanism or lock-out mechanism may be automatically released and the injector 7 is ready to fire (inject). In such cases, the injector 7 is prevented from being actuated (it is locked out) until it is placed against the skin. Alternatively, the user may manually remove a safety 100 such as a safety pin, safety sleeve, tab, or collar to release the injector to be ready to fire (to inject, or to direct the cannula through the opening into the subject). The injector 7 in some instances cannot be fired until the safety mechanism 100 is released. The safety mechanism 100 may be passive or active and manually triggered by the user or automatically triggered by the injector 7.

Referring to FIGS. 7-9, the injector 7 may use an actuator or button 77 and a visual indicator 101 in combination to indicate a parameter of the injector 7 after it has been removed from the transfer apparatus. For example, when the button 77 is in the up position and the indicator 101 has one color such as but not limited to green, this may indicate that the injector 7 is ready to start the injection. Additionally, the button 77 may have a side wall 102 that is a different color from its top 103. When the button 77 is depressed, the user cannot see the sidewall 102 of the button 77; this may indicate that the injector 7 is in use. The injector 7 may alert the user when the injection of the drug is completed. This alert could be in the form of visual indicators, audible sounds, mechanical movements or a combination. The button 77 is ideally designed to give the subject or user audible, visual and tactile feedback when the button 77 'pops up' into the locked-out position. The injector 7 may indicate to the subject that it is has completed dispensing and the full dose has been delivered to the patient with the button 77 in the up position and indicator window 101 showing the injector reservoir is empty. For example, when the button 77 is in the up position and indicator 101 shows a different color such as but not limited to red, this may indicate that the injector 7 has completed the injection.

Figure 10:
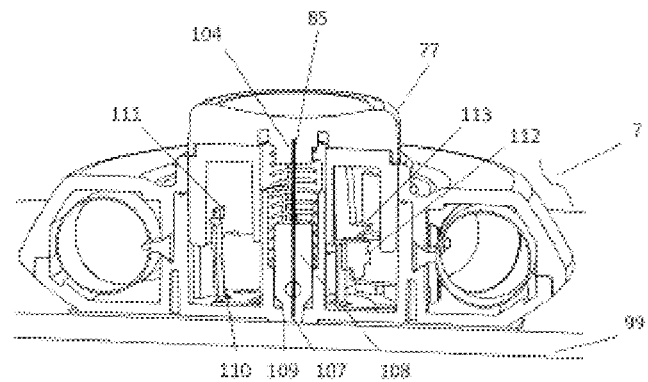
FIG. 10 shows a cross-section view of the injector attached to the body (e.g., skin) with the button up in a pre-fire state.
Figure 11:
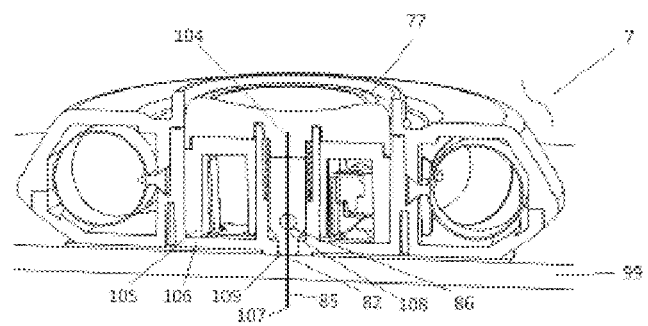
FIG. 11 shows a cross-section view of the injector attached to the body (e.g., skin) with button down in a first fired state.
Figure 12:
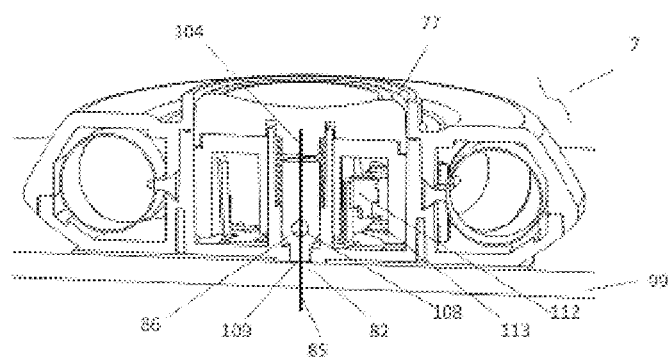
FIG. 12 shows a cross-section view of the injector attached to the body (e.g., skin) with button down in a dispense state.

Referring to FIGS. 10-12, the injector 7 may have an actuator or button 77 that the subject or user depresses on the injector 7 to start the injection. The button 77 may be configured to be an on/off switch, i.e., to only have two states, open and closed such as a light switch. This may prevent the user from pushing the button 77 half way and not actuating the injector 7. Once activated, this 'light switch' type button 77 would direct the cannula 85 rapidly into the skin 99, independent of the user manipulation of the button 77. Alternatively, the button 77 could have a continuous motion, allowing the user to slowly direct the cannula 85 into skin 99. The button 77 may preferably be directly coupled to the cannula 85 by using adhesive 104 creating a button 77 and cannula 85.

Referring to FIGS. 10-12, the injector 7 may have a cannula 85 that, when the injector 7 is coupled to the skin and upon actuation, directs the substance from the reservoir to a fluid flow path in fluid communication with the reservoir, thereby directing the substance from the reservoir into the skin 99. Upon actuation of the button 77 that initially goes to a first position or depth as shown in FIG. 11 and retracts slightly to a second position of depth, in some cases automatically, as shown in FIG. 12. The first depth shown in FIG. 11 is achieved from over travel of the button 77 during actuation. The first depth may be controlled by features 105 in the button 77 in direct contact with the base 106 of the injector 7. The final depth of the cannula 85 is suitable for subcutaneous injections. Alternatively, the final depth of the cannula 85 may be reduced for intradermal injections. Alternatively, the final depth of the cannula 85 may be increased for intramuscular injections. Upon reaching the first depth, the cannula 85 retracts away from the body of the subject to a second depth as shown in FIG. 12. The retraction distance of the cannula to the second depth is in the range of 0.1-2 mm. This retraction feature is used, in such cases, to prevent the cannula 85 from being blocked by tissue during the initial insertion process. This tissue blockage could require a very high pressure to overcome and prevent the injector 7 from delivering the drug. The retraction of the cannula 85 from the first position to a second position generates an open pocket ahead of the cannula tip 107 allowing reduced pressure for initiation of flow of drug from the cannula 85. This reduced pressure for initiation of the flow of drug from the cannula is necessary, in some instances, for the injector 7 to maintain a relatively constant pressure, to direct the substance through the cannula during injection.

Referring to FIGS. 10-12, the injector 7 may include a cannula 85 with a side opening 108. As shown in FIG. 12, once the button 77 on the injector 7 is fully depressed, the cannula 85 will be fully inserted into the skin 99 through the dispense port 82 and the injector 7 will begin dispensing of the substance. Until the button 77 is fully depressed, the side-hole 108 and therefore the internal lumen of the cannula 85 is not in communication with the fluid channel 86 of the dispense port 82. Both the side-opening 108 and cannula-tip 107 are retained within a septum 109. With the side-opening 108 and cannula-tip 107 being retained within the septum 109, the entire drug path is kept sterile until the time of use. When the button 77 is fully depressed and the cannula 85 is in the dispense position, the side opening 108 in the cannula 85 is in communication with the fluid channel 86 of the dispense port 82 and the injection of the substance (e.g., injectable medicament or fluid) begins.

Referring to FIGS. 10-12, the septum 109 provides the advantage of sealing the cannula tip 107 as well as the side opening 108 from the injectable before and after dispensing. Sealing the cannula tip 107 and the side opening 108 of the cannula 85 at the end of the injection has a particular advantage to prevent dripping of the substance (e.g. injectable liquid) from the injector 7 after end of dispense and/or after it is removed from the skin surface. It also prevents contaminates from entering the hollow cannula prior to being actuated into the skin. The septum 109 may comprise a pierceable membrane that can be made of any suitable material to allow for sealing once the cannula 85 has punctured it. The material composition of septum 109, or of the pierceable membrane, may comprise silicone. Alternatively, the material composition of the septum 109, or pierceable membrane, may also be a blend of different materials including but not limited to bromobutyl, chlorobutyl, isoprene, polyisoprene, SBR, polybudtadiene, EPDM, PTFE, natural rubber and silicone. Alternatively, the fluid pathway 86 including the dispense port 82 could comprise a rigid plastic with a silicone injected overmold to produce the septum previously described.

Referring to FIGS. 10-12, the septum 109 at the dispense port 82 could protrude slightly from the underneath surface into the skin surface 99 of the injector 7 to provide for pressure on the skin surface 99 at the injection site. This pressure on the skin surface 99 by the dispense port 82 after the cannula is retracted could eliminate the substance from coming out of the injection site commonly referred to as blowback.

Referring to FIGS. 10-12, the injector 7 may include a set of spring tabs 110 that interface with the button 77 to perform locking functions. A spring tab 110 is biased to lock into an undercut 111 in the button 77 to keep the button 77 in a first up position or pre-fire position as shown in FIG. 10. The geometry of the undercut 111 and spring tab 110 help to produce the light switch actuation force described previously. This light switch actuation is accomplished by the translation of the button 77 relative to the spring tab 110 and the geometry of the mating undercut 111 surfaces.

Referring to FIGS. 10-12, the injector 7 may include a spring tab 112 that interact with the button 77 in the injector 7 to perform locking functions such that when the button 77 is actuated to the first depth and retracts slightly back to the second depth or dispense position, undercut features 113 in the button 77 allow a spring tab 112 to hold the button 77 in the dispense position until the injector 7 has completed dispensing.

Figure 13:
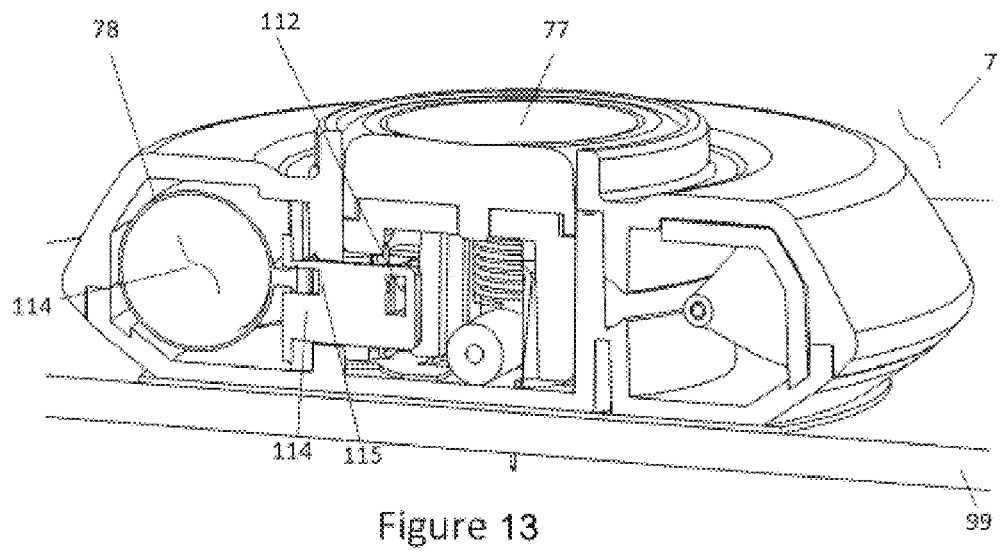
FIG. 13 shows a cross-section view of the injector attached to the body (e.g., skin) showing the end of delivery indicator not triggered.
Figure 14:
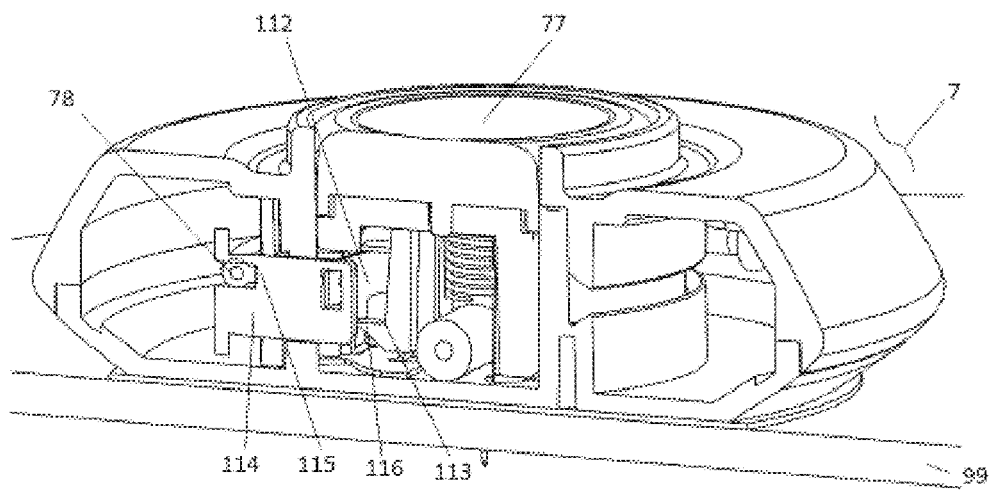
FIG. 14 shows a cross-section view of the injector attached to the body (e.g., skin) showing the end of delivery indicator triggered.

Referring to FIGS. 13-14, the injector 7 may include an end of delivery indication or empty indicator 114 to sense when all of the substance (e.g., medicament or injectable fluid) has been expelled from the expandable member 78 and the injector 7 has completed dispensing. The empty indicator 114 may be configured with a slot or other opening 115 to slide over the expandable member 78 at the exit port when the expandable member 78 is in a deflated state after all of the substance has been expelled. There may be two states of the empty indicator. As shown in FIG. 13, the empty indicator may be in a first position or deflected-out state when the expandable member 78 is full of the substance at that section and is not contained within the slot or opening 115. This first position would translate to a non-empty state of the expandable member 78 when the diameter of the expandable member 78 is larger than its minimum due to residual substance contained within. As shown in FIG. 14, the empty indicator 114 may be in a second position or deflected-in state when the expandable member 78 is partially or fully contained within the slot or opening 115. This second position would translate to an empty state of the expandable member 78 when the diameter is at a minimum.

Referring to FIGS. 13-14, the injector 7 may include an automatic cannula retraction mechanism at the end of dispense. This mechanism includes a direct coupling between a spring tab 112, button undercut feature 113 and the empty indicator 114, all previously mentioned. When the expandable member 78 is filled with the substance (e.g., medicament or injectable fluid) and the button 77 is depressed from a first pre-fire position to a second dispense position as shown in FIG. 14, undercut features 113 in the button 77 allow a spring tab 112 to hold the button 77 in the dispense position until the injector 7 has completed dispensing. This spring tab 112 may also be directly coupled to the empty indicator 114 which is naturally in the first position or deflected-out state. The motion of depressing the button 77 to a second position or dispense position allows a post feature 116 in the button 77 to provide a bias or pre-tension on the spring tab 112 to direct the empty indicator 114 to its second position or deflected-in state. However, since the expandable member 78 is initially full of substance at a large diameter, the empty indicator 114 cannot move to the second position or deflected-in state as shown in FIG. 13. After the button 77 is depressed, the substance starts to expel out of the expandable member 78 through the cannula as previously mentioned. Once the expandable member 78 has expelled all of the substance and is at a minimum diameter, the empty indicator 114 (under pretension from the spring tab 112) will move to the second position or deflected-in state as shown in FIG. 14. The spring tab 112 directly coupled to the empty indicator 114 also moves with the empty indicator 114. This movement releases the spring tab 112 from the undercut feature 113 in the button 77 to allow the button 77 (and cannula) to move up to a final position or post fire position after the dispense is completed as shown in FIG. 15.

Figure 15:
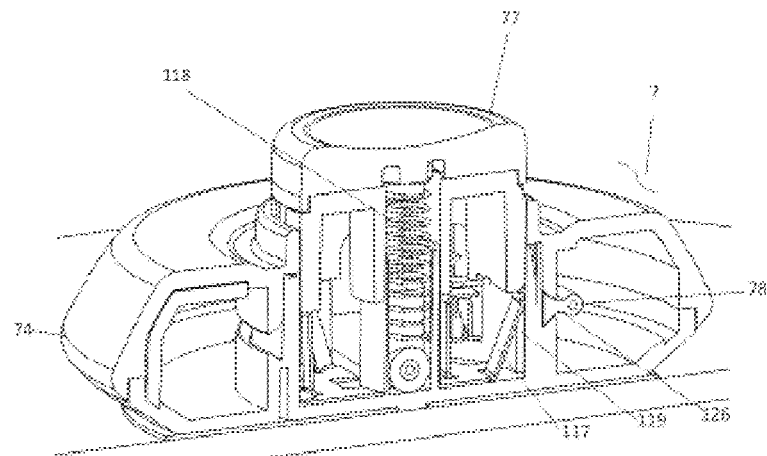
FIG. 15 shows a cross-section view of the injector attached to the body (e.g., skin) with button locked up in a post-fired state.

Referring to FIG. 15, lock out spring tabs 117 may also interact with the button 77 in the injector 7 to perform locking functions such that when the injection is complete the button 77 is released, and the button 77 is urged up by the return spring 118 to a final up position or post-fire position. The button height 77 relative to the top of the injector 7 in the final up position or post-fire position (shown in FIG. 15) may be higher than the pre-firing position (shown in FIG. 10). The end of the lock out spring tabs 117 move out to the outer diameter surface 119 of the button 77 within the outer housing 74 to lock the button 77 in the up position or post-fire position and prevent the button 77 from being actuated again.

Referring to FIG. 15, the injector 7 may include a return spring 118 that interacts with the button 77 to provide a bias to the button 77 into a first up position or pre-fire position. When the button is actuated down to a second depth or dispense position, the return spring 118 is compressed causing more of a bias or preload. At the end of the dispense period, the button 77 is unlocked from the second depth or dispense position (shown in FIG. 12) to move up to a final position or post fire position after the dispense is completed as previously mentioned. It is the bias of the return spring 118 that forces the button 77 up to a final position or post-fire position.

Figure 16:
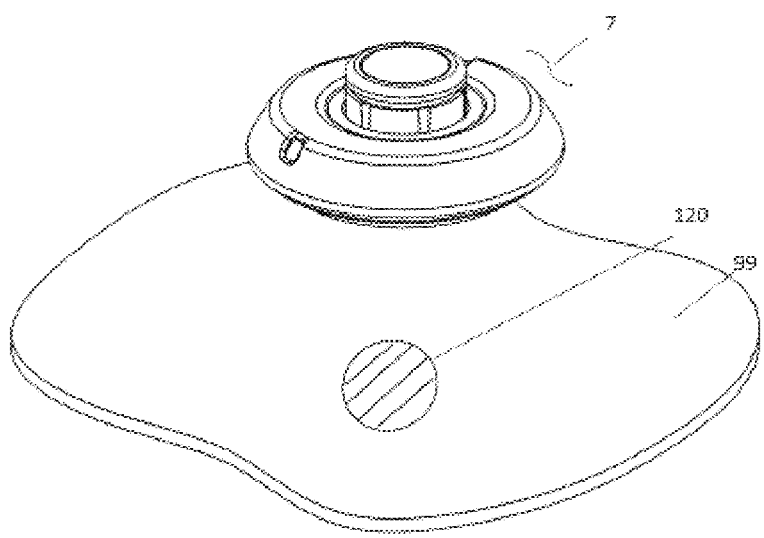
FIG. 16 shows a perspective view of the injector removed from the body (e.g., skin) with the bandage remaining on the skin.

Referring to FIG. 15-16, upon removal of the injector 7 from the skin 99, the injector 7 will preferably be locked out, preventing non-destructive access to the cannula or reuse of the injector 7. The injector 7 may indicate to the user that the full dose has been delivered. This indication could be in the form of a visual indictor, audible sound, mechanical movement or a combination.

Figure 16B:
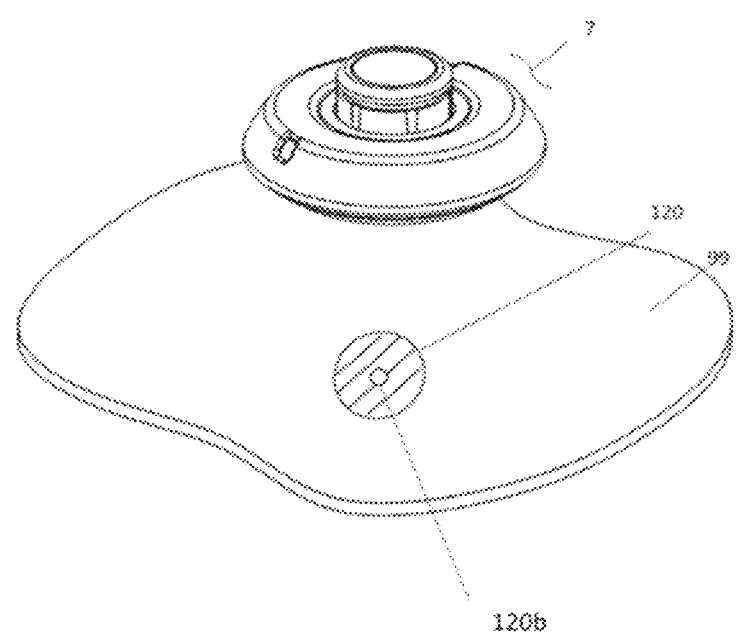
FIG. 16B shows a perspective view of the injector removed from the body (e.g., skin) with the bandage, comprising an opening, remaining on the skin.

Referring to FIG. 16, upon removal of the injector 7 from the skin 35, a bandage 120 may release from the injector 7 and remain on the skin surface 35. This can be affected by using an adhesive on the bandage portion that more strongly attaches the bandage to the skin than the adhesive that attaches the bandage to the injector 7. Thus when the housing is lifted from the skin, the bandage 120 remains in place over the injection site as described in U.S. Pat. No. 7,637,891 and U.S. patent application Ser. No. 12/630,996, which are incorporated by reference herein. The bandage 120 may comprise an opening 120b (e.g. hole or slit in the center of the bandage), as shown in FIG. 16B.

Referring to FIGS. 36-39, the injector 7 may preferably include a manifold 121 that assembles to both the expandable member 78 and the filling port 81 and dispensing ports 82 and provides direct fluid communication between the expandable member 78 and the filling 81 and dispensing 82 ports of the injector 7. The manifold 121 may be configured on the end that assembles to the expandable member 78 to be large in diameter to facilitate filling and expelling all of the substance out of the expandable member 78 as previously discussed. The manifold 121 may preferably include internal passageways 122 to allow for fluid flow in and out of the expandable member 78. The manifold 121 may be configured with a filter 123 in the injectable fluid pathway 122 for filtering the substance to remove particulate before and after it is introduced into the expandable member 78. The filter 123 may be a membrane, depth filter or other suitable filtration media that is of sufficiently small pore size or effective pore size to remove objectionable particulate, which may include but not be limited to undissolved substance in those situations where the substance is reconstituted by the transfer apparatus. The manifold 121 may also be configured with a filter 123 for the removal or air. Such an air remover filter 123 may include a bubble trap, air gap, or other configuration in the injectable fluid pathway 122 that removes air from the injectable fluid pathway 122 before it is introduced into the expandable member 78. This air remover filter 123 may be configured with a hydrophobic filter or a combination of hydrophobic and hydrophilic filters. A hydrophobic filter would allow for the venting of air from the transfer apparatus but not the passage of liquid. A hydrophilic filter would allow the passage of liquid but not the passage of particulate or air. The air remover filter 123 may also have check valves to allow for venting of trapped air. Alternately, the air remover and filters 123 may be located at any point in the fluid pathway from the filling port 81 to the cannula 85. For example, the most downstream point in the fluid pathway is the distal end 128 of the expandable member 78. An internal mandrel 124 may be connected to distal end 128 of the expandable member 78. An air remover or filter 123 may be integrated into this downstream point to allow for venting of trapped air during filling of the injector 7. Furthermore, the mandrel 124 could include a slot along its length that is in communication with the downstream filter 123 to aid in the venting of air during the filling process.

Referring to FIGS. 36-39, the injector 7 may include a resilient expandable member 78 such as an elastomeric balloon or bladder. The material composition of expandable member 78 may preferably be silicone. Alternatively, the material composition of the expandable member 78 may also be a blend of different materials including but not limited to bromobutyl, chlorobutyl, isoprene, polyisoprene, SBR, polybudtadiene, EPDM, PTFE, natural rubber and silicone. In addition, the expandable member 78 may be coated to improve their surface properties. Coatings may include parylene, silicone, Teflon and fluorine gas treatments. Alternatively, the expandable member 78 may be made from a thermoplastic elastomer.

Referring to FIGS. 36-39, the injector 7 may include a resilient expandable member 78 which the substance is transferred under pressure. This causes the expandable member 78 to enlarge and the resilience of the expandable member 78 creates a pressure which tends to expel the substance. The pressure chamber of the transfer apparatus described previously (or such other pump or pressurizing means as may be employed in the transfer apparatus) transfers the substance to the injector 7 under pressure. Introducing the substance into the expandable member 78 under pressure causes it to stretch and expand both in diameter and length. An example of this would be blowing up a long, skinny balloon. The volume range of the injector 7 may be 0.5 to 30 milliliters. When expanded, the resilient expandable member 78 exerts an expulsion pressure in the range of 1 to 200 psi on the substance contained in the expandable member 78 so that the injector 7 is ready to administer the substance automatically when triggered by the user by depression of the button as previously described. Thus, the transfer apparatus as previously described operates not only to transfer a measured amount of substance (and if necessary mix, dilute and filter it) to the injector 7, but also simultaneously charges or provides the motive pressure to the injector 7 (by expanding the resilient expandable member 78) so that the injector 7 is ready to automatically dispense the substance under the pressure exerted by the resilient expandable member 78 when actuated by the user.

This aspect of the transfer apparatus (simultaneous transferring and charging) is particularly beneficial. While the above applications show the injector 7 in a pre-filled or charged condition for injection of the substance 79 when the injector 7 is actuated, the present disclosure contemplates that the injector 7 can remain empty and the expandable member 78 in a more relaxed and un-filled condition, i.e., in a non-charged or non-filled condition, until administration of the substance is required. Only then is the substance mixed or processed as necessary and introduced into the injector 7, expanding the expandable member 78 to a filled (charged) condition. In the present disclosure, the drug is stored in its original container closure (vial) until the time of use. Because the substance will typically be injected within seconds to hours after transfer from the vial into injector 7, shelf life and material compatibility of the drug with the materials in the fluid pathway within the injector 7 are not significant issues. The challenges and expense of designing an injector 7 and selecting materials for an extended shelf life of pre-filled injector 7 are significantly reduced.

Referring to FIGS. 36-39, the present subject matter may use features of the injector 7 described in the patent applications incorporated by reference herein as previously described. However, the expandable member 78 employed in the injector 7 here may also preferably take the form of an elongated balloon or bladder arranged, for example, in a planar helical or spiral configuration as illustrated. As previously mentioned, the injector 7 includes a circular shaped outer housing 74 that has a spiral slot or recess 125 formed therein. The elongated balloon or bladder 78 rests in the slot 125, with one end for communicating directly or indirectly with an injection cannula 85 through fluid pathways 122 and the other end for communicating directly or indirectly with a dispense indicator 101. The elongated spiral configuration allows the balloon or bladder 78 to have substantial volume for such quantity of substance 79 as may be desired, while also contributing to the low-profile configuration of the injector 7. In some cases, by utilizing a relatively long expandable member 78 with a large length to diameter ratio, very high pressures and volumes can be achieved with a minimum of forces required. Additionally the volume of the expandable member 78 can be changed by changing the filling length, without significantly altering the pressure/volume curves of the expandable member 78.

Figure 36:
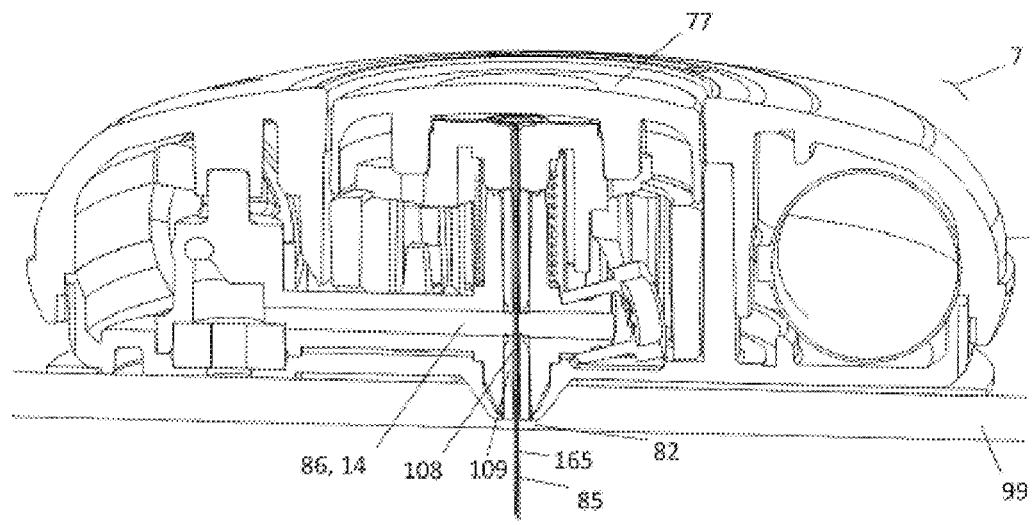
FIG. 36 shows a cross-section of FIG. 25 showing an injector with the button in the first position or pause position.
Figure 37:
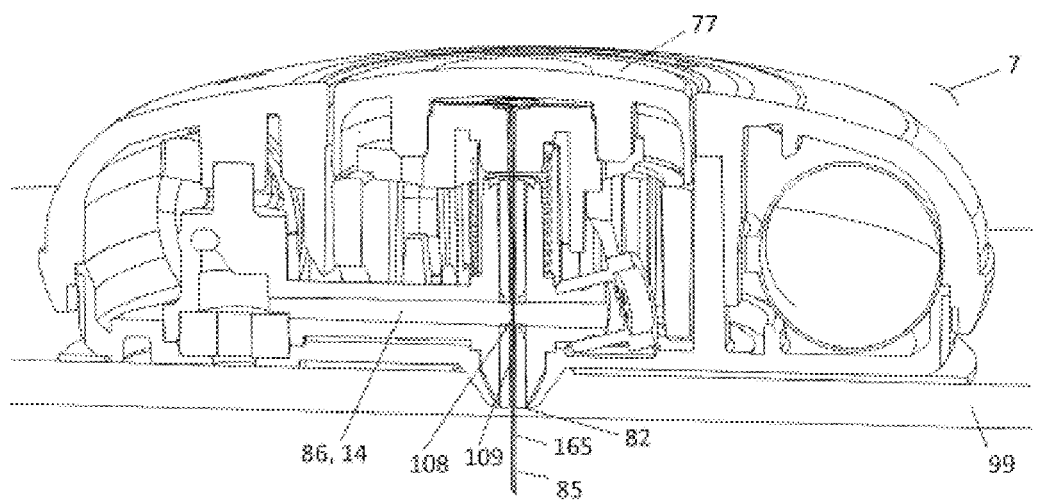
FIG. 37 shows a cross-section of FIG. 25 showing an injector with the button in a second position or dispense position.
Figure 38:
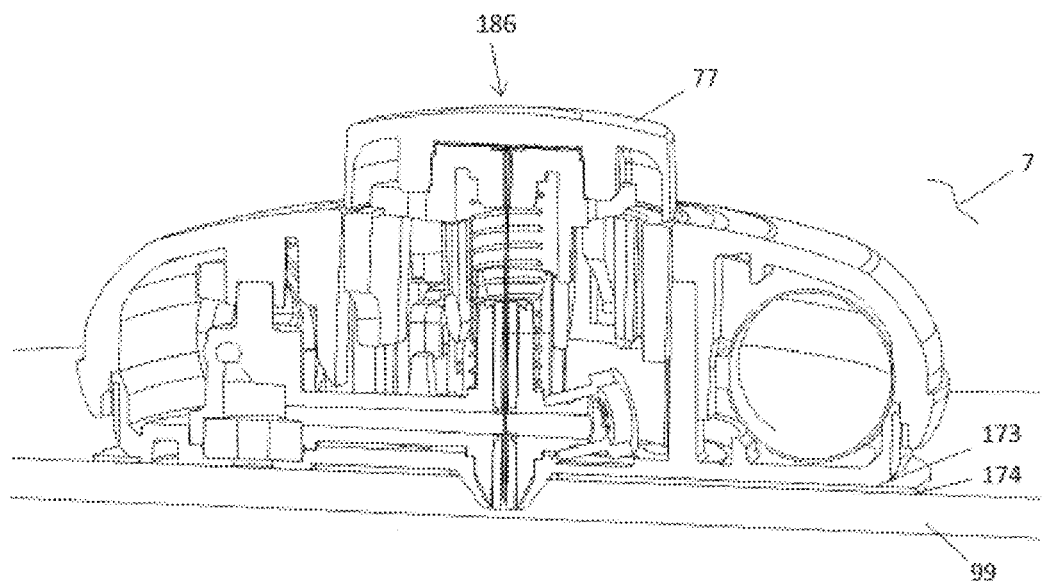
FIG. 38 shows a cross-section of FIG. 25 showing an injector with the cannula retracted and the button in the up or pre-fire position.
Figure 39:
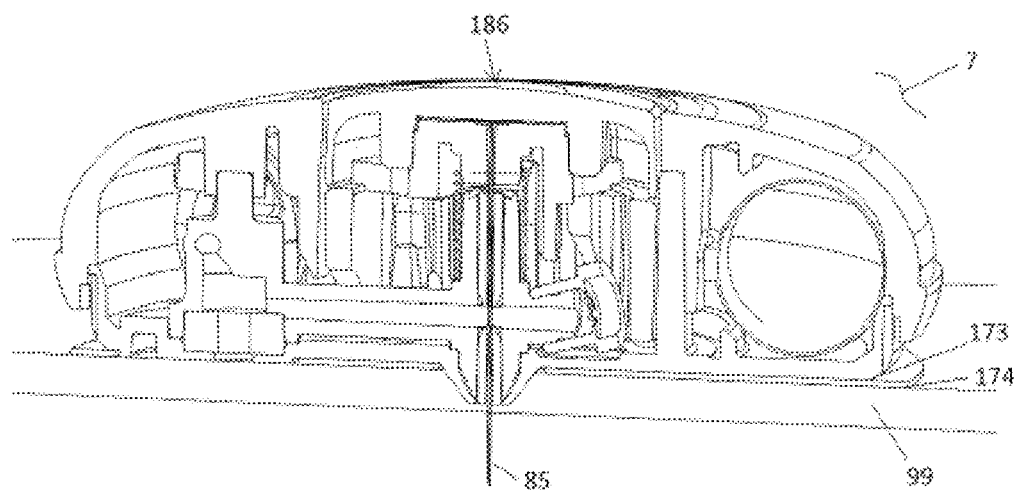
FIG. 39 shows a cross-section of FIG. 25 showing an injector with the button in a second position or dispense position.

Referring to FIGS. 36-39, one of the other aspects that may be employed in the present subject matter is the use of an insert or plug or mandrel 124 within the expandable member 78 to pre-stress the expandable member 78 to a slightly expanded position when unfilled, so that when the expandable member 78 expels the substance, it will contract or collapse to a condition where it is still stretched or stressed and continues to exert pressure on any fluid there within as shown in FIGS. 38 and 39. This better assures that all or substantially all of the substance is fully expelled from the injector 7. The mandrel or shaft 124 could be a fluid filled expandable member if desired. This would allow for a variable size mandrel 124. Alternatively, the expandable member 78 could have a sufficiently small internal volume (small diameter) when unstressed so that virtually all the substance is expelled without the need for and internal mandrel or shaft 124. Additionally, the expandable member 78 could be flattened/stretched by 'wrapping' it around a surface within the injector such as a cylindrical wall 134. The pre-stress created in the expandable member 78 would act to eliminate any residual fluid volume remaining within.

There are a number of different ways to cause an expandable member 78 to expand and/or contract in an arcuate manner as previously described. Referring back to FIG. 15, one way is to design the expandable member 78 with a thicker wall cross section 126 in one area around the circumference of the expandable member 78 that would cause the expandable member 78 to expand in a circular fashion. Alternatively, a separate element 126 could be affixed along the length of the expandable member 78 to effectively stiffen the expandable member 78 in that portion of the circumference that would cause the expandable member 78 to expand in an arcuate manner. Referring back to FIG. 17, another way is to use internal features such as slots or recesses 125 in the housing 74 of the injector 7 to guide the expandable member 78 around a circular or spiral path. These features 125 could interact with the expandable member 78 in a number of ways, the simplest being the outer shape of the expandable member is constrained by a slot 125 in the housing 74 of the injector 7. Friction between the expandable member 78 and the inner surfaces 125 of the housing 74 could be reduced by lubricating the outside surface of the expandable member 78, or by inserting the expandable member 78 within a low spring rate spring that would limit both the friction and outer diameter of the expandable member 78 while not constraining the length.

Referring to FIGS. 36-39, the elongated expandable member 78 may be preferably configured to expand along an arc with a predetermined tube diameter without the aid of walls or a guide within the injector. Referring back to FIG. 15, looking at a cross-section of the elongated expandable member 78, a thicker wall area 126 in a small portion of the circumference of the expandable member 78 may be added to cause the elongated expandable member 78 to expand in an arc as previously described. The arcuate expandable member 78 grows in length due to increase in pressure and volume there within; the thicker section 126 deflects less than the thinner section.

Figure 17:
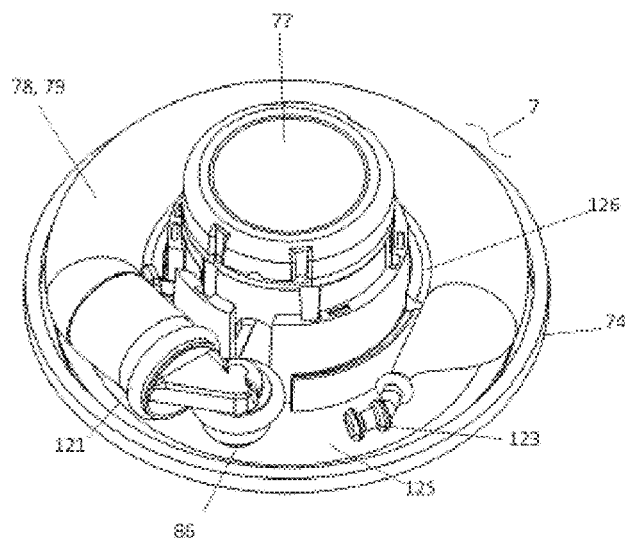
FIG. 17 shows a perspective view of the injector with the top housing removed in a filled state.

Referring to FIG. 17, the arcuate expandable member 78 will expand in length in an arc shape as to orient its heavy wall thickness zone 126 or less deflecting zone to the inside of the circle. Increasing the wall thickness 126 of the expandable member 78 within the small zone 126 around the circumference will effectively continue to decrease the radius of the arc of the expandable member 78. The increase in wall thickness 126 may be achieved by molding or extruding it into the arcuate expandable member 78 or by bonding a strip of material to one side 126 of the expandable member to cause that portion of the wall 126 to lengthen at a slower rate, thereby causing the expandable member 78 to expand in an arc shape as previously discussed.

Figure 18:
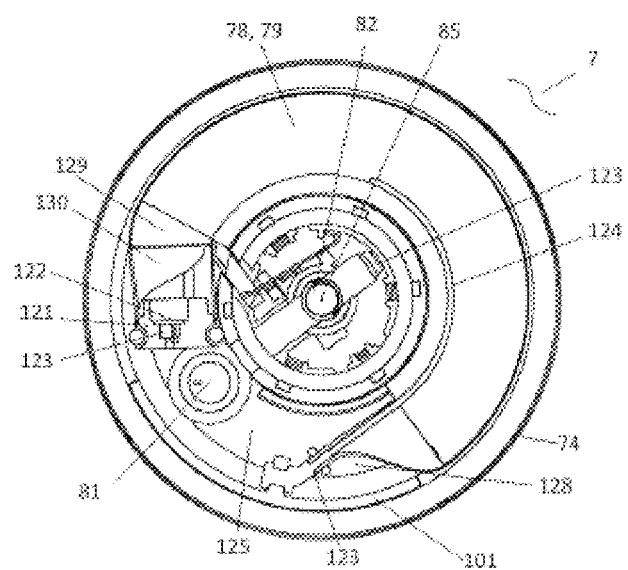
FIG. 18 shows a top view of the injector shown in FIG. 17.
Figure 19:
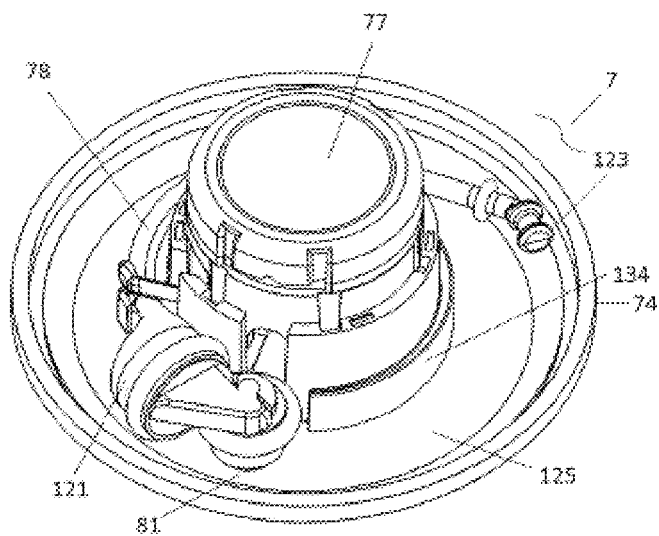
FIG. 19 shows a perspective view of the injector with the top housing removed in an empty state.
Figure 20:
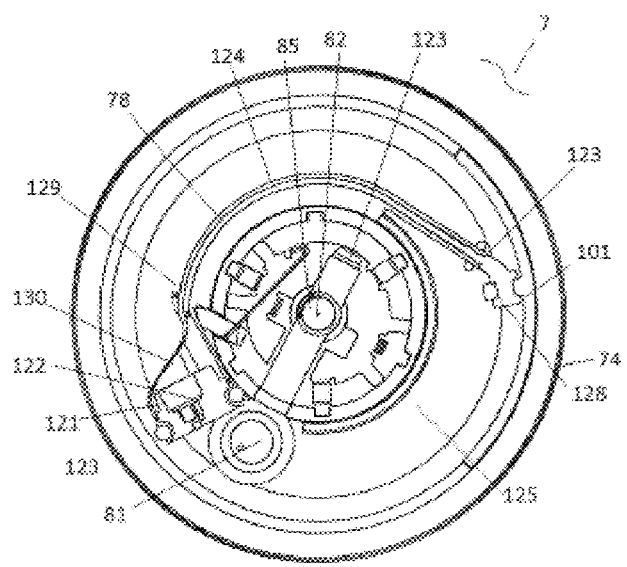
FIG. 20 shows a top view of the injector shown in FIG. 19.

Referring to FIG. 18, the distal end of the expandable member 78 could be affixed an element such as an indicator 101, which is constrained to follow guide path within the inner surfaces 125 of the housing 74. Alternately, the expandable member 78 could be pre-stretched and flattened around a circular diameter inside the injector 7 such as wall 134 so that there would be no change in expandable member length. Alternatively, a straight or curved mandrel 124 whose length is more than the unstressed expandable member could be used to stretch the expandable member into a circular shape within the injector 7 prior to filling. Alternatively, the mandrel 124 could be used as a visual indicator to show the state of the injector 7 and the progress of the injection. The mandrel 124 could be colored to allow it to be easily viewed through the housing.

Referring to FIGS. 36-39, the substance is injected into the expandable member 78 by the transfer apparatus and the expandable member 78 is expanded to a certain outer diameter controlled by the configuration of the inner surfaces 125 of the housing 74. In this way, the entire length of the expandable member 78 can be filled with a known volume of drug, and the outer diameter is known at each lengthwise location along the expandable member 78. It is desirable to have the expandable member 78 fill and empty along its length in a controlled way, from one end to the other to encourage the expandable member 78 to completely empty, and to allow the easy and accurate measurement of substance in the expandable member. To visually aid in determining how much substance is in the expandable member 78, graduated markings could be printed on the expandable member 78, like a syringe, to indicate the volume remaining in the expandable member 78. As previously described and referring to FIGS. 21-22, the expandable member 78 and housing 74 could be clear to allow the user to see the drug 74 and the volume remaining in the injector 7. Alternatively, graduated markings 127 could be printed on the housing 74 to indicate the volume remaining in the expandable member 78.

Referring to FIGS. 36-39, in accordance with an aspect of this subject matter mentioned above, the substance can be expelled progressively from the distal end 128 of the elongated expandable member 78 toward the proximal end 129. The proximal end 129 of the expandable member is closest to the dispensing cannula 82 or cannula. This allows the user to visually ascertain or approximate the injection status visually alone or with the aid of graduation markings 127 on the injection housing 74, the window 80 or the expandable member 78. Progressive expulsion may be achieved in a variety of ways. For example, the substance exits the expandable member 78 at the manifold 121 at the proximal exit port section 130 and is preferably located at the proximal end 129 of the elongated expandable member (e.g., balloon or bladder). The thickness of the wall of the expandable member 78 may be varied, uniformly or stepwise increased, along its length from the distal end 128 toward the proximal end 129. Due to restraint by the walls of the spiral channel 125 in which the expandable member 78 resides, the expandable member 78 would be inflated with substance to a substantially uniform diameter along its length. However, the thicker wall at the distal end 128 of the expandable member 78 would exert greater contraction force on the substance than the thinner wall at the proximal end 129 and thus collapse or contract in diameter first during expulsion of the substance. The expandable member 78 would then collapse progressively from the distal end 128 toward the proximal end 129 as the wall of the expandable member 78 becomes thinner along its length in that direction. Because the thickness of the expandable member 78 preferably substantially uniformly increases from the proximal end 129 toward the distal or closed end 128, the contractive force of the expandable member 78 wall when expanded will increase substantially uniformly along the length of the elongated expandable member 78 from the proximal port end 129 to the distal or closed end 128. Thus, when the substance is expelled into the subject, the expandable member 78 will progressively collapse in diameter as well as shrink in length, which collapse in diameter and shrinkage in length is preferably viewable by the user as described above. The distal end 128 of the elongated expandable member may allow for the connection of a movable indicator component 101 in the injector 7 which will follow the shrinkage in length of the elongated expandable member 78. This indicator 101 is preferably viewable by the user through the outer housing 74 and indicates the state of the injector 7 and the progress of the injection. Alternatively, the expandable member 78 is configured with a constant wall thickness and could be prestressed in manufacturing to bias it to fill from the proximal end 129 to the distal end 128 and collapse or empty from the distal end 128 to the proximal end 129 in a progressive manner as previously discussed.

Referring to FIGS. 36-39, the elongated expandable member 78 of the injector 7 may be configured to have a section 130 of the expandable member 7 adjacent to the proximal exit port end 130 that fills first and collapses last during filling and expulsion of the substance from the injector 7. In other words, during filling of the injector 7 by the transfer apparatus, it is advantageous to have the most proximal exit port section 130 of the expandable member 79 to fill with injectable first. Additionally, during dispense of the substance from the injector 7, it is advantageous to have the last remaining volume of substance to be contained within the most proximal exit port section 130 the expandable member 79. There are several advantages to the abovementioned configuration. The proximal end section 130 of the expandable member 78 could have a thin wall that would cause it to remain inflated under a lower pressure than the rest of the expandable member 78. This would assure that the section 130 of the expandable member 78 would remain inflated until all substance had been expelled from the rest of the expandable member 78. As previously discussed, this section 130 may be directly coupled to an empty indicator to provide for full or empty indication. Additionally, as previously mentioned, this section 130 could be mechanically coupled to the empty indicator to allow for the automatic withdrawal of the button 77 and cannula 82 upon complete expulsion of the substance.

Referring to FIGS. 36-39, alternatively or in addition to varying the wall thickness 126 of the expandable member 78, an elongated internal mandrel or shaft 124 within the expandable member 78 may progressively (linearly or stepwise) decrease in cross-sectional size along the length of the expandable member 78 from proximal end (the exit port end) 129 toward the distal end (closed end) 128 of the expandable member 78. Additionally, the manifold 121 which allows for attachment of the expandable member 78 to the injector 7 may also be configured with a large diameter section 130 at the proximal end 129 of the expandable member 78. A large diameter section 130 of the mandrel 124 or manifold 121 at the proximal end exit port 129 of the expandable member 78 insures that the expandable member 78 will fill with substance in this area 129 first. In other words, the expandable member 78 is being held at nearly a fill diameter at the proximal end exit port 129 by the large diameter section 130 of the mandrel 120 or manifold 121. As substance first starts to fill the expandable member 78, it reaches a fill diameter first in the large diameter section 130 then fills progressively along the length of the expandable member 78 from the proximal end 129 to the distal end 128 as previously discussed.

Referring to FIGS. 36-39, as previously discussed, during dispense of substance from the expandable member 78, the diameter of the expandable member 78 at its distal end continuously collapses in a progressive fashion (similar to deflating a long skinny balloon) from its distal 128 to proximal end 129 until all of the fluid is expelled from the expandable member 78. A large diameter section 130 of the mandrel 124 or manifold 121 at the proximal end exit port 129 of the expandable member 78 provides the same benefit (as previously described for filling) during dispense of the substance. This large diameter section 130 insures that the last remaining substance in the expandable member 78 will be contained and dispensed from this area 130. As previously discussed, this section 130 may be directly coupled to an empty indicator to provide for full or empty indication as well as for the automatic withdrawal of the button 77 and cannula 82 upon complete expulsion of the substance.

Figure 21:
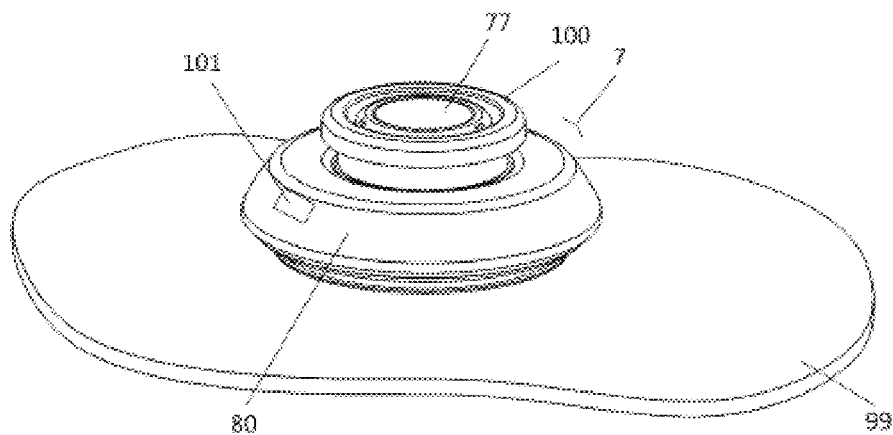
FIG. 21 shows a perspective view of the injector placed on the body (e.g., skin) and the safety in place.

Referring to FIG. 21, the user attaches the injector 7 to their skin 99. There may be an adhesive on the bottom of the injector 7 that allows for adhesion to the skin 99 surface and hands-free operation. The adhesive may extend past the outline of the injector to allow the user to firmly adhere the tape to the skin. Alternatively, the user may hold the injector 7 against the skin 99 for the duration of the injection.

Figure 22:
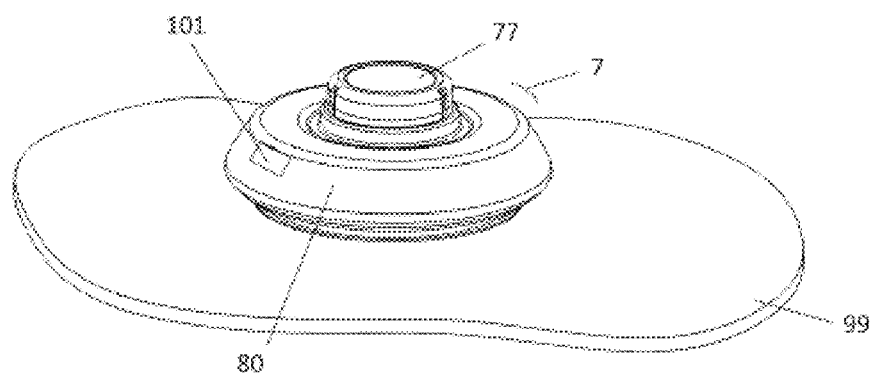
FIG. 22 shows a perspective view of the injector placed on the body (e.g., skin) and the safety removed.
Figure 23:
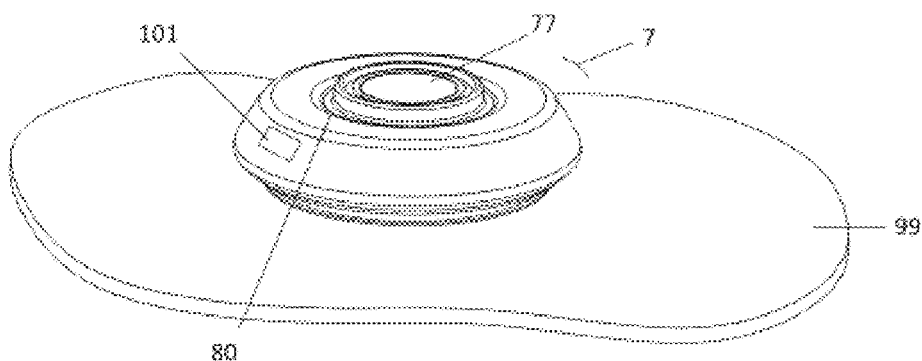
FIG. 23 shows a perspective view of the injector placed on the body (e.g., skin) and the button depressed to fire start the injection.

Referring to FIGS. 21-23, the user removes the safety 100 and depresses the button 77 on the injector 7 to start the injection. Once the button 77 on the injector 7 is fully depressed, it is locked into place and the cannula will be fully inserted into the patient and the injector 7 will begin dispensing the injectable drug. The injector 7 may alert the user that injection of the drug has started. This alert could be in the form of visual indictors, audible sounds, mechanical movements or a combination. The time of the injection could be in a range of a few seconds to several hours. The injector 7 may indicate to the user that it is dispensing with the button 77 locked in the down position and indicator window 101 showing the injector 7 is less than full. The injector 7 preferably has a clear section 80 that allows the user to easily determine the amount of drug remaining in the injector 7.

Figure 24:
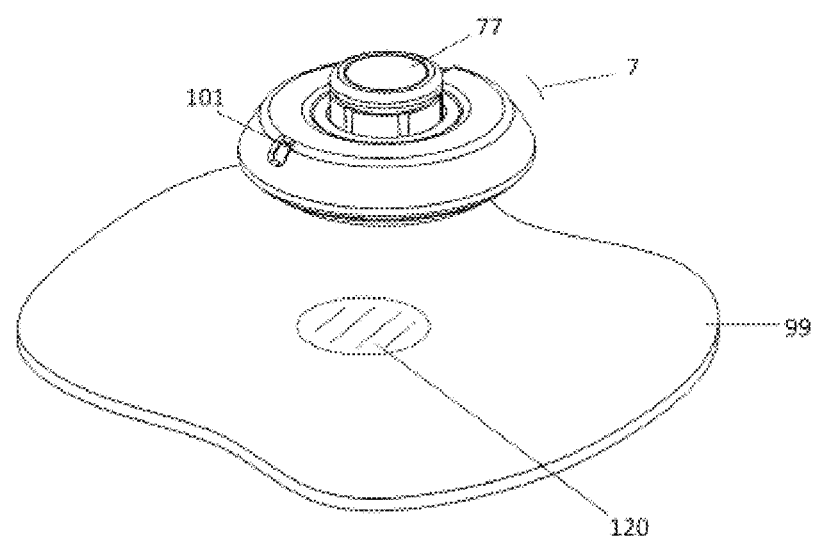
FIG. 24 shows a perspective view of the injector removed from the body (e.g., skin) after the injection with the button in a locked position and a bandage remaining on the body (e.g., skin).

Referring to FIG. 24, the user will be alerted when the injection of the drug is completed. This alert could be in the form of visual indicators, audible sounds, mechanical movements or a combination. The injector 7 may indicate to the user that it is has completed dispensing with the button 77 moving to a locked-up position with tactile and audible sounds and indicator window 101 showing the injector is empty. At the end of the dispense, the cannula will automatically retract into a locked position within the injector 7.

Referring to FIG. 21, upon removal of the injector 7 from the skin 99, a bandage 120 could release from the injector 7 and remain on the skin surface 99. Upon removal from the skin 99, the injector 7 will preferably be locked out, preventing non-destructive access to the cannula or reuse of the injector 7. The injector 7 may indicate to the user that the full dose has been delivered. This indication could be in the form of a visual indictor, audible sound, mechanical movement or a combination.

In accordance with further aspects of the present subject matter, when administering an injection with a syringe and cannula that is meant to be infused under the skin, it is desirable to know if the cannula is properly placed within the skin or improperly placed within a blood vessel. It is common for a user performing an intradermal (ID), subcutaneous (SC) or intramuscular (IM) injection to aspirate the syringe by pulling back on the plunger to create a pressure drop within the syringe to see if any visible blood comes up the cannula into the syringe. If blood is visualized, this means the tip of the cannula is in a blood vessel. A number of injectable drugs meant for infusion under the skin specifically indicate not to inject into a blood vessel. Blood aspiration using a syringe and cannula is a common technique and can be performed by anyone with adequate training. In some cases, an autoinjector may be used, and the autoinjector may comprise a mechanism for determining whether the autoinjector is properly placed.

Figure 25:
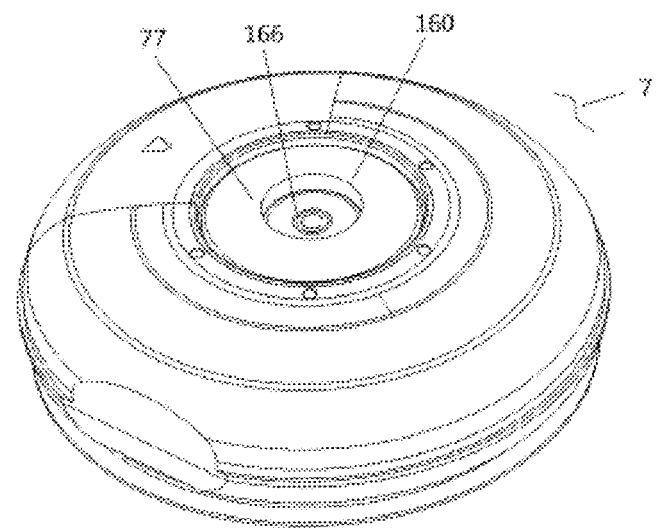
FIG. 25 shows a perspective view of an injector.
Figure 26:
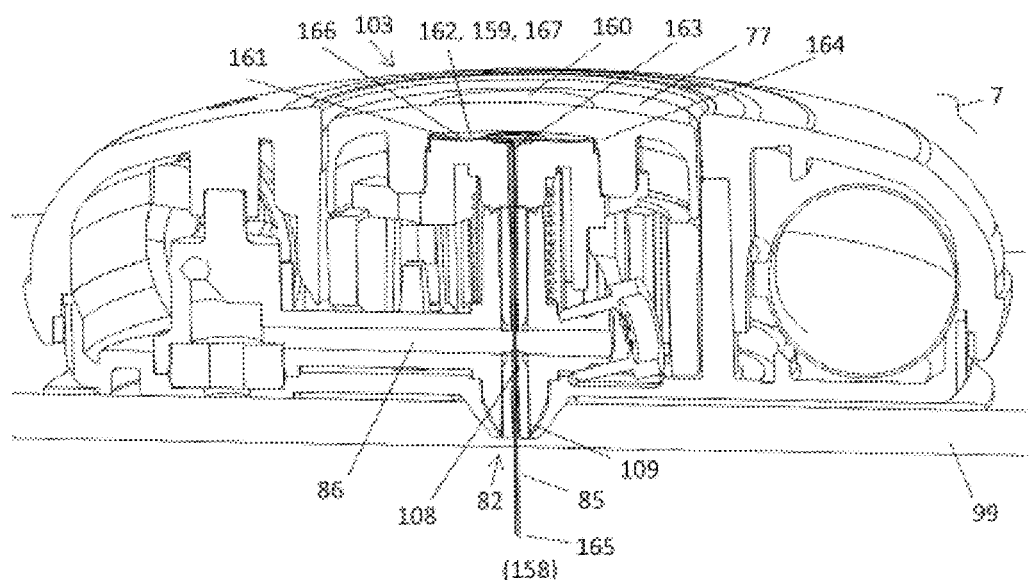
FIG. 26 shows a cross-section of FIG. 25 showing the injector with the button in the first position.

Referring to FIGS. 25-26, the injector 7 may have a cannula 85 with a side-opening (e.g., hole) 108 in operative engagement with the button 77 slidable within a septum 109 advancing into the skin 99. The button 77 may have a viewing window 160 on the button top 103 that is in fluid communication with the proximal end 161 of the cannula 85. The button top 103 may include a cavity 162 for blood 159 to accumulate and be seen through the button window 160 by a user. The cavity 162 may include a center hole 163 that allows fluid communication with the proximal end 161 of the cannula 85 via cannula lumen 165. The outer walls 164 of the cavity 162 are formed by the button top 103. Additionally, a portion of the outer walls 164 may include a hydrophobic filter 166. In this configuration, the proximal end 161 of the cannula 85 is at atmospheric pressure. If fluid 14 or blood 159 travel up the internal lumen 165 of the cannula 85, it exits the proximal end 161 of the cannula 85 and fills the cavity 162. The air 167 in the cavity 162 is easily displaced through the hydrophobic filter 166 until all of the air 167 has been displaced from the cavity 162 and it is full of fluid 14 or blood 159. At this point, the flow of fluid 14 or blood 159 stops as the fluid 14 or blood 159 cannot penetrate the hydrophobic filter 166 and can be easily viewed through the window 160 of the button top 103 by the user thus providing a method for determining if the injector 7 cannula 85 is in a blood vessel 158.

Figure 27:
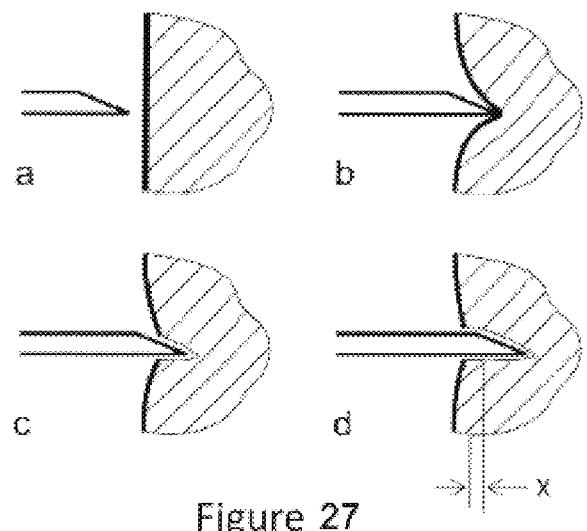
FIG. 27 shows an illustration (Van Gerwen, D. J. *Cannula-Tissue Interaction by Experiment*. Ph. D. Thesis, Delft University of Technology, 2013. ISBN 978-94-6186-238-9, pg. 11) showing four stages of cannula penetration into tissue including a) no contact, b) boundary displacement, c) tip insertion and d) shaft insertion.

Referring to FIG. 27, cannula insertion into tissue can be generally divided into four stages. These include no contact (panel a), boundary displacement (panel b), tip insertion (panel c) and shaft insertion (panel d). During boundary displacement, the tissue boundary in the contact area deflects under the influence of the load applied by the cannula tip, but the cannula tip does not penetrate the tissue. The boundary of the skin follows the tip of the cannula up to a maximum boundary displacement point in the contact area as the cannula tip starts to penetrate the skin. After the cannula tip penetrates the skin, the shaft is inserted into the tissue. Even after tip and shaft insertion, the boundary of the skin surface in the contact area does not return to its original no contact state but remains displaced by a distance x. The amount of boundary displacement x is a function of several parameters including but not limited to cannula diameter, cannula tip geometry, cannula shaft friction, cannula insertion speed and physical skin properties. Boundary displacement x of the skin in the contact area is characterized in cannula-based injectors because it effects how much of the cannula penetrates the skin and therefore reduces the actual cannula penetration depth by the amount of boundary displacement x. If the boundary displacement x could be intentionally induced by stretching or preloading such as pushing the skin out at the contact site prior to cannula tip insertion, there would be no additional boundary displacement by the cannula tip or shaft during insertion and the cannula tip depth could be predictably defined. The advantage of this intentional displacement is the amount of cannula penetration into tissue would not be affected by variations in the boundary displacement x. Without intentionally inducing boundary displacement at the skin surface prior to cannula tip insertion, the actual cannula penetration depth into the skin is not specifically known because some of the cannula length (depending on the abovementioned parameters) is outside the skin due to the naturally occurring boundary displacement x shown in FIG. 27. On the other hand, if the maximum boundary displacement could be induced at the contact site, the actual cannula penetration depth would not change with the variations in the abovementioned parameters including cannula diameter, cannula tip geometry, cannula shaft friction, cannula insertion speed and physical skin properties.

Figure 28:
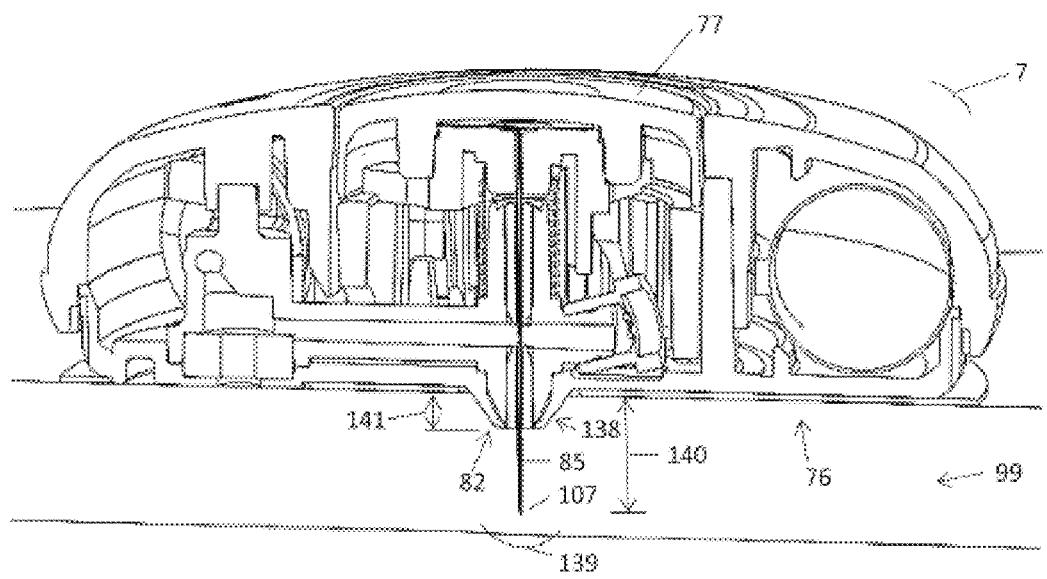
FIG. 28 shows a cross-section of FIG. 25 showing an injector with the button in a second position or dispense position.
Figure 47:
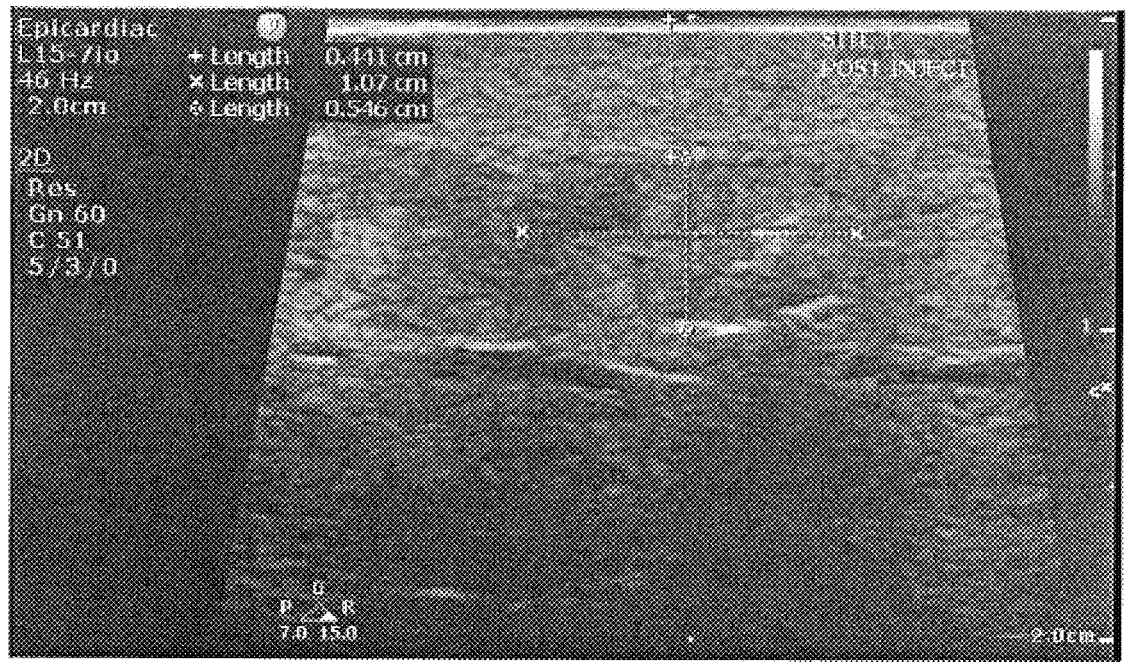
FIG. 47 shows an ultrasound image showing the subcutaneous depth of a bolus injection employing a commercial infusion pump with a 9 mm subcutaneous cannula depth.
Figure 48:
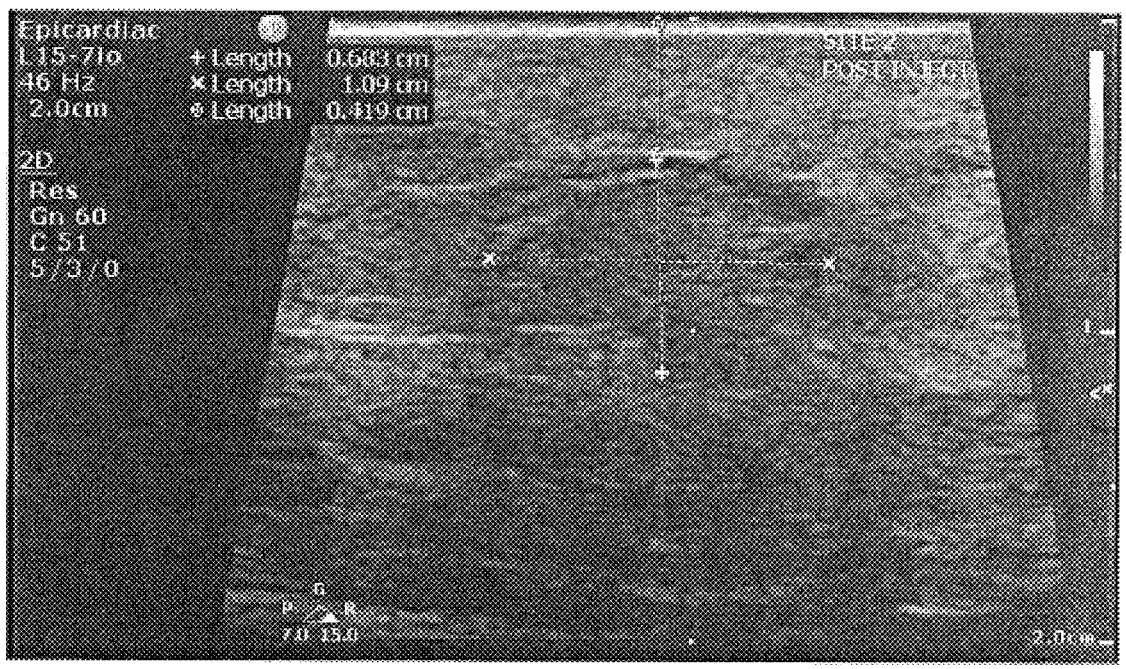
FIG. 48 shows an ultrasound image showing the depth of a bolus injection employing injector 7 with a 5 mm cannula depth.
Figure 49:
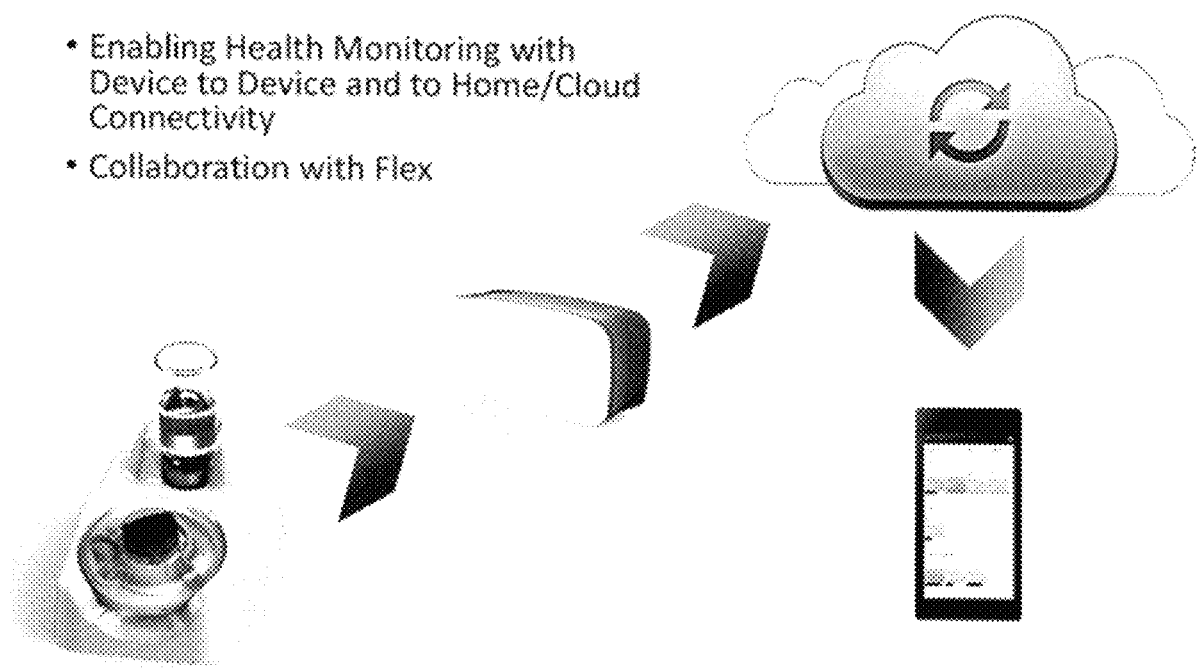
FIG. 49 depicts a compliance monitoring system.
Figure 51:
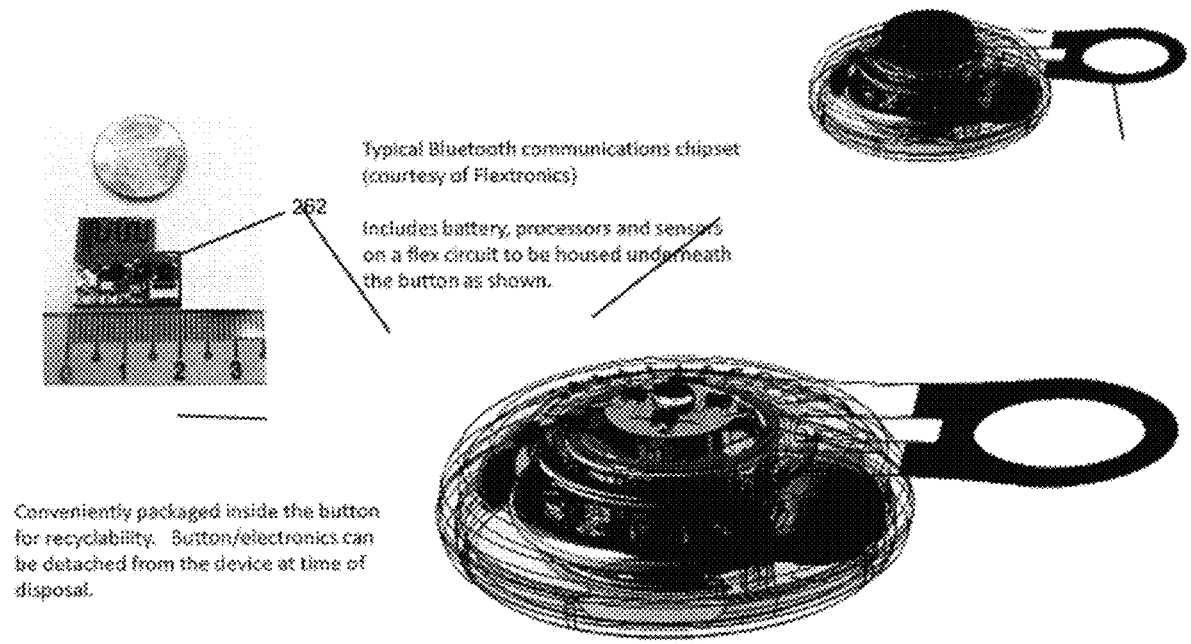
FIG. 51 shows additional aspects of a compliance monitoring with an injector of the type described herein.

Referring to FIG. 28, the injector 7 may have a skin boundary displacement extension or structure, such as an underside surface 76 that includes an extension 138 at or around the dispense port 82 or as part of the dispense port 82. The extension extends substantially normal to plane of the tissue at the point of cannula insertion. When the injector 7 is attached to the skin 99, the extension 138 will protrude against the skin 99 surface resulting in displacement or compression of the skin 99 in this contact area 139. The compression of the skin helps to reduce or eliminate "tenting" of the tissue surface upon cannula insertion. In other words, by "pre-loading" the tissue by compressing it, the extension 138 serves to eliminate further tissue defection or tenting, or results in more reproducible and lesser amount of skin surface deflection or tenting. During actuation of the button 77 from a pre-fire state to first position, the cannula 85 advances out of the injector 7 through the dispense port 82 and/or extension 138 into the skin 99 to start the dispense of drug. For the reasons described above, as the cannula 85 advances out of the injector 7, the tip of the cannula 107 does not produce additional boundary displacement 141 (already intentionally induced by the extension 138) in the skin 99 at the contact area 139. Thus the actual cannula penetration depth 140 into the skin 99 is better characterized and controlled. Also, the extension, through which the cannula passes, compresses the tissue immediately around the cannula, which has several advantages. During the injection, the compression of the tissue by the extension 138 in the contact area 139 increases the local density of tissue thus creating a higher-pressure zone compared to the surrounding adjacent tissue 99. As injectable enters the skin 99, the fluid will migrate from this high-pressure zone 139 to lower pressures areas in the skin 99 which helps to prevent injected fluid or drug from flowing or migrating into the immediate area around the cannula/skin puncture site and acts to reduce or minimize fluid leakage (backflow) and/or bleeding from the puncture site. This higher-pressure zone also effectively provides the benefit of a much longer injection cannula. For example, in an ultrasound evaluation comparing the subcutaneous deposition depth of a 10 mL fluid bolus (saline) using the injector 7 with a 5 mm needle depth and an off-the-shelf infusion pump (Freedom 60, RMS) with a butterfly needle extension set (9 mm needle depth), results show that the subcutaneous depth of the 10 mL bolus, post injection was equivalent between the injector 7 with a 5 mm needle length and the pump with a 9 mm needle length. In all results, bolus position is characterized by distance (Zd) from the skin surface to top edge of bolus. FIG. 47 shows the top edge of the 10 mL subcutaneous bolus using the pump with 9 mm cannula length. The Zd distance is measured at 0.44 cm. FIG. 48 shows the top edge of the 10 mL subcutaneous bolus using the injector 7 with a 5 mm cannula length. The Zd distance is measured at 0.42 cm. Thus, a similar depth of the bolus is provided with a cannula depth (5 mm) and the tissue displacement structure that is more than 40% shorter than the other tested cannula (9 mm) without a tissue displacement structure.

Another advantage of the extension 138 is compression of the tissue in the contact area 139 after the injection has completed. In the post-fired state, the button 77 has popped up alerting the user that the injector 7 has completed. The cannula 85 is fully retracted out of the puncture hole in the skin 99. The dwell time between when the injector 7 has completed dispense and is removed by the user can be several minutes or more, depending on the environment in which the user is in at the time of completion. For the same reasons described earlier, the compression of the tissue by the extension 138 in the contact area 139 increases the local density of tissue thus creating a higher-pressure zone compared to the surrounding adjacent tissue 99. Similar to how a nurse may apply pressure to an injection site with their thumb after injection, this pressure helps close the puncture hole and prevents injected fluid or drug from flowing back up the injection site and acts to reduce or minimize fluid leakage and/or bleeding from the puncture site.

Figure 29:
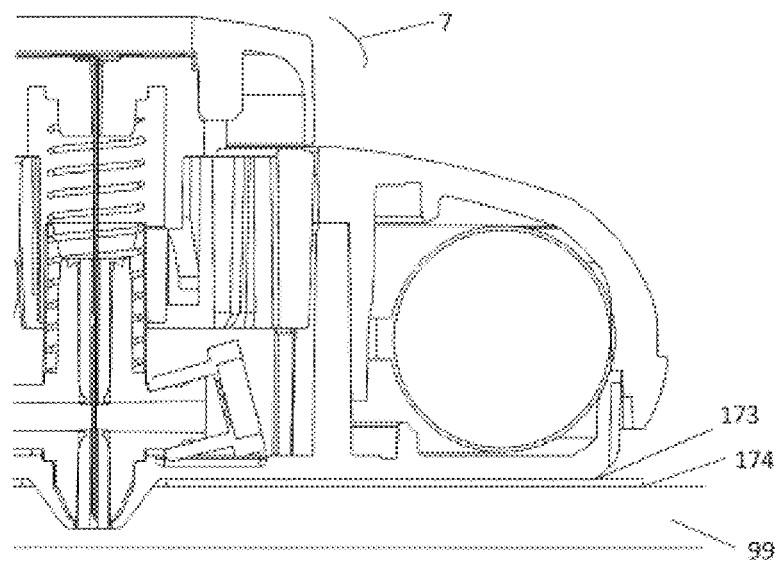
FIG. 29 shows a cross-section of FIG. 25 showing adhesive/device and adhesive/body (e.g., skin) interfaces.

Referring to FIG. 29, there are two interfaces related to adhering the injector 7 to the skin 99. The first is the adhesive/device interface 173 and the second is the adhesive/skin interface 174.

Figure 30:
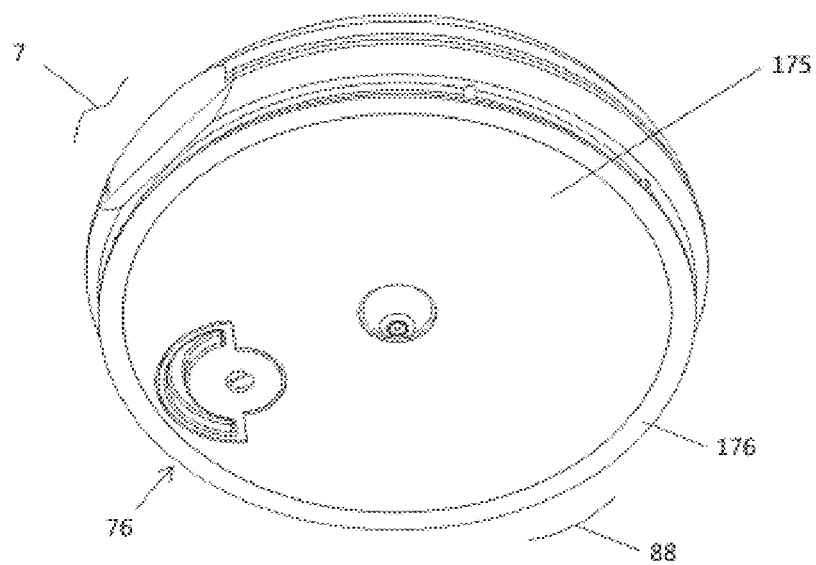
FIG. 30 shows a perspective view of the bottom of an injector showing the different zones of the adhesive.

Referring to FIG. 30, the adhesive 88 could be configured on the injector 7 with at least two zones. The first zone 175 may include a permanent bond using mechanical or chemical means between the adhesive 88 and the injector 7 and preferably be positioned within the perimeter of the injector 7. The second zone 176 may be configured to be detachable or unattached from the injector 7 and preferably be adjacent and on the outside (e.g., radially outward) of zone 1.

Figure 31:
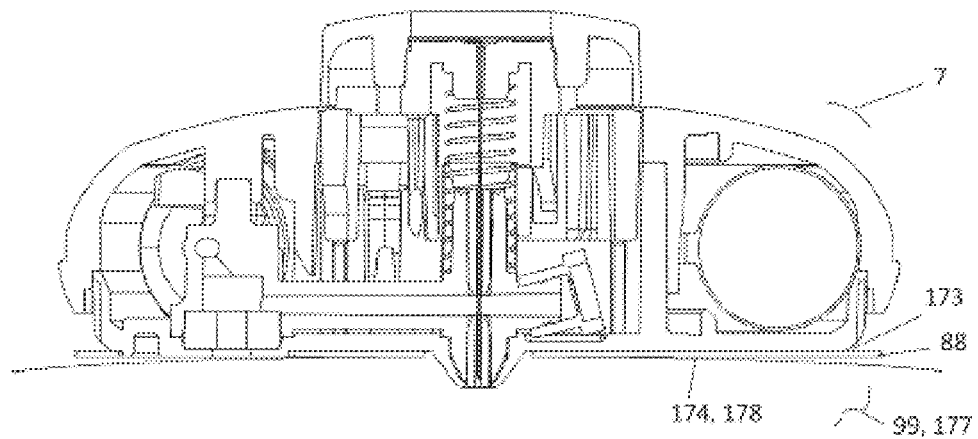
FIG. 31 shows a cross-section of FIG. 25 showing bulging tissue on a device with permanently attached adhesive.

Referring to FIG. 31, if the adhesive 88 were completely attached to the bottom 76 of the device 7, during a tissue bulge 177 event the adhesive 88 at the adhesive/skin interface 174 would start to peel from the skin 99 because this interface 174 is weaker than the adhesive/device interface 173. This is demonstrated on a bulging surface in FIG. 31. This may result in the injector 7 becoming dislodged from the skin surface 99 and falling off the patient.

Figure 32:
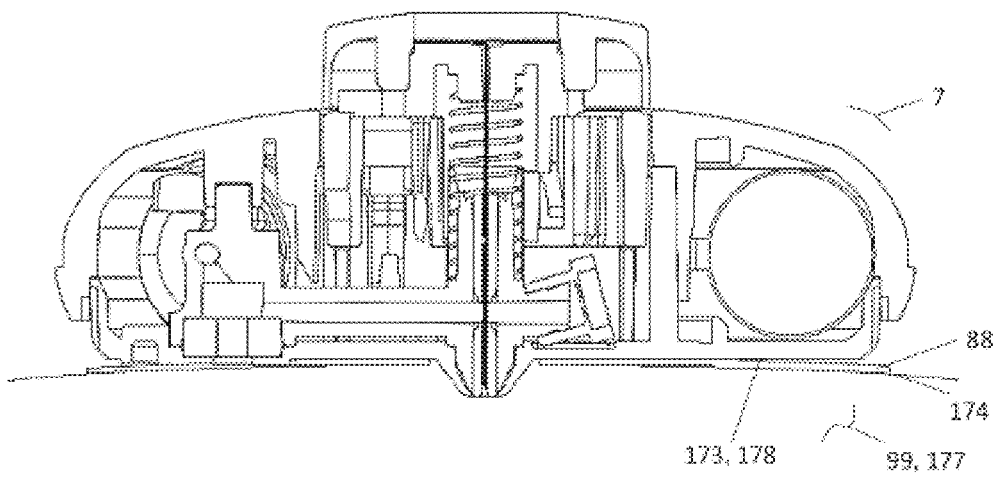
FIG. 32 shows a cross-section of FIG. 25 showing bulging tissue on a device with multi-zone attached adhesive.

Referring to FIGS. 30 and 32, instead of permanently attaching the adhesive 88 completely to the bottom 76 of the injector 7 as shown in FIG. 31, the adhesive 88 could be configured on the injector 7 with the abovementioned zones 175, 176. During a tissue bulge event 177 in this configuration, the adhesive 88 in zone two 176 would detach from the injector 7 and be firmly attached to the skin 99 surface at the adhesive/skin interface 174. This would allow for transfer of the peel edge 178 from the adhesive skin interface 174 to the adhesive/device interface 173 effectively creating a strain relief at the adhesive/skin interface. The adhesive/device interface 173 may be designed to be much stronger and prevent injector 7 separation from the skin surface 99.

When performing self-injections with automatic injectors, protecting the user from accidental cannula sticks is a beneficial requirement for the device. Typically, the cannula is retracted within the device before and after use, preventing the user from accessing the cannula. However, during the injection, the cannula can be extended outside of the device. In some instances, the automatic injector comprises a skin dislodgement sensor to automatically retract a cannula if the device becomes dislodged from the skin during the injection.

Figure 33:
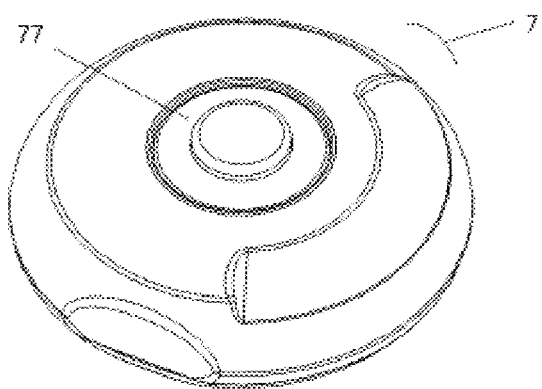
FIG. 33 shows a perspective view of the top of an alternative injector.
Figure 34:
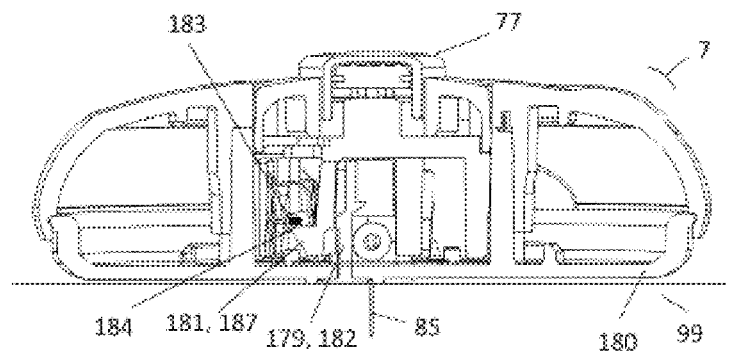
FIG. 34 shows a cross-section of FIG. 33 showing a dislodgment sensor non-engaged and the cannula locked in the dispense position.
Figure 35:
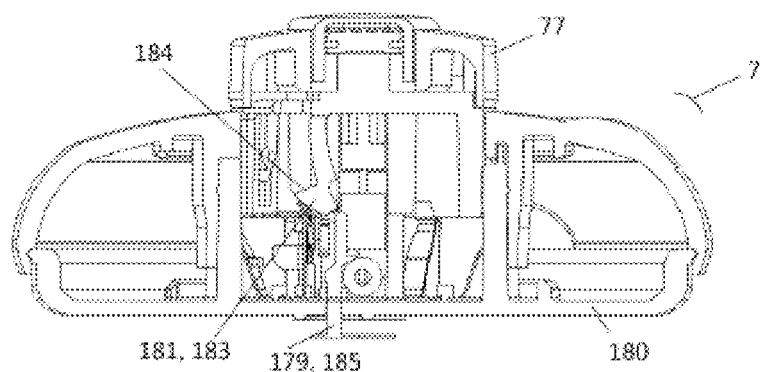
FIG. 35 shows a cross-section of FIG. 33 showing a dislodgment sensor engaged and the cannula and button retracted to post-fire position.

Referring to FIG. 33-35, a skin dislodgement sensor 179 may be in operative engagement with a flexible latch 181 of the button 77 and slidable within the lower housing 180 of the injector 7. Referring to FIG. 34, when the injector 7 is attached to the skin surface 99, the skin dislodgement sensor 179 is forced into a first or up position 182 inside the injector 7. When the button 77 is actuated to a fired state or second position or dispense position (exposing the cannula 85), the flexible latch 181 is forced into a lock position 187 by the skin dislodgement sensor 179 under the latch board 183. The latch board 183 holds the button 77 at the latch board surface 184 on the button 77 down in the fired state or dispense position until the end of dispense. At the end of dispense, the latch board 183 translates away from the latch board surface 184 on the button 77, allowing the button 77 and cannula 85 to retract to a post fire position where the cannula 85 is contained within the injector 7. Referring to FIG. 35, in the event that the injector 7 becomes dislodged from the skin surface 99 during injection, the skin dislodgement sensor 179 extends to a second or down position 185 out of the injector 7. This allows the flexible latch 181 to spring back to an unlocked position and disengage from the latch board 183. This allows the button 77 and cannula 85 to retract to a post fire position where the cannula 85 is contained within the injector 7.

When performing self-injections with a syringe and cannula, users may have the need to temporarily stop or pause the injection due to acute pain or irritation at the injection site. This pause in flow of injectable into the injection site, accomplished by removing pressure on the plunger rod of the syringe, helps to reduce the pain at the injection site by allowing the injectable fluid bolus more time to diffuse into the surrounding tissue and thus reducing the local pressure and associated pain and irritation. In some instances, the injector comprises a mechanism for pausing the injection, e.g., automatically or manually.

Referring to FIGS. 36-37, upon actuation of the button 77, the cannula 85 and button 77 travel to a first position or depth as shown in FIG. 36. In this first position or depth, the side-hole 108 is covered by the septum 109 and therefore the internal lumen 165 of the cannula 85 is not in communication with the fluid channel 86 of the dispense port 82. The button 77 may be intentionally held in this first position or depth to prevent flow of injectable 14 from the fluid channel 86 into the side-hole 108 of the cannula 85 and into the skin 99. As shown in FIG. 37, when the button 77 is released, the cannula 85 and button 77 return to a second position or dispense position where the side-hole 108 is exposed to the fluid channel 86 allowing the flow of injectable 14 from the fluid channel 86 into the side-hole 108 of the cannula 85 and into the skin 99 until the end of the injection. This action of pushing the button 77 to the first position or depth may be performed as many times a necessary during the entire injection.

Referring to FIGS. 38-39, the button 77 actuation force 186 is the transition load applied to the button 77 required to start displacement of the button 77 and cannula 85 from a pre-fire position to a fired state or dispense position. Until this transition load is met, the force 186 applied to the button 77 is transferred directly to the injector 7. Specifically, this load 186 may be transferred to adhesive skin interface 174 and/or the adhesive device interface 173 resulting in better securement of the injector 7 to the skin surface 99 prior to actuation of the injector 7.

Figure 40:
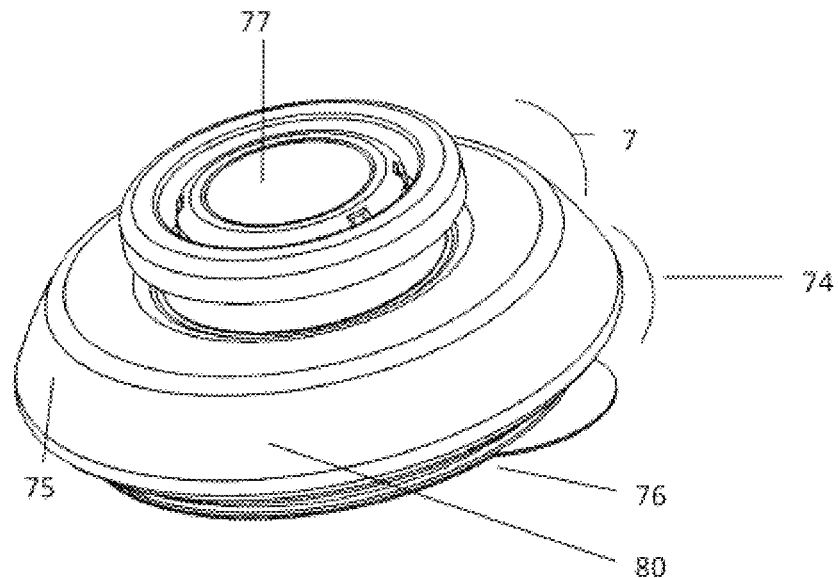
FIG. 40 shows a perspective view of an injector.
Figure 41:
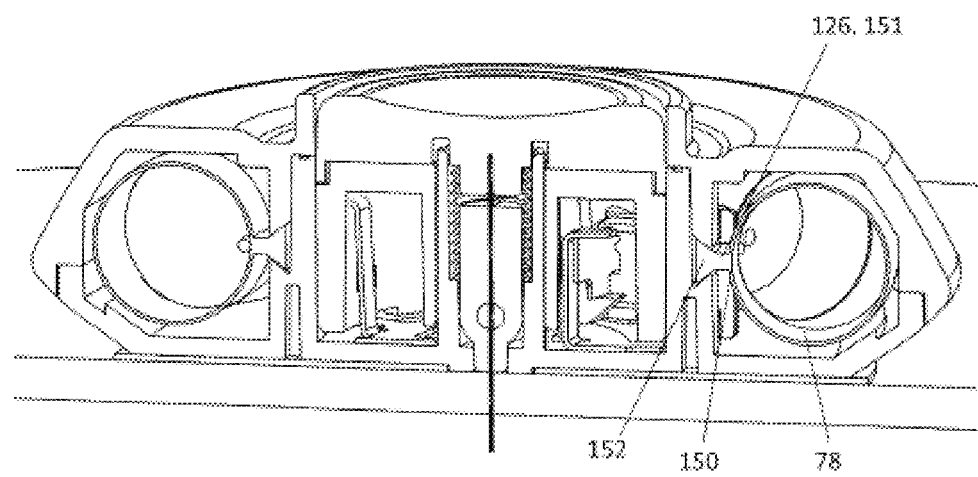
FIG. 41 shows a cross-sectional perspective of an injector with the button in a second position or dispense position.

Referring to FIGS. 40-41, the arcuate expandable member 78 is positioned and/or will preferably expand in length in an arc shape. In the illustrated embodiment, the arc shape is induced by providing a less resilient area for example a thicker or relatively heavy wall thickness zone 126 which will result in less deflection of the expandable member in that zone and result in formation of an expanded arc shape. This heavy wall thickness zone 126 may be configured in any shape that will allow for the arc shape in the expandable member 78 during expansion. A preferred configuration for the heavy wall thickness zone 126 is to minimize its thickness or attachment 150 in the circumferential direction on the expandable member 78 wall and maximize the radial thickness or projection 151 away from the expandable member 78. This serves to urge the expandable member 78 to expand in an arc shape but also maximizes the amount of material along the circumference that is unaffected by the heavy wall thickness zone 126 for expansion. Additional features including but not limited to a T-shape may be configured to the end of the radial projection 152 to help urge the expandable member 78 into an arc shape.

Figure 42:
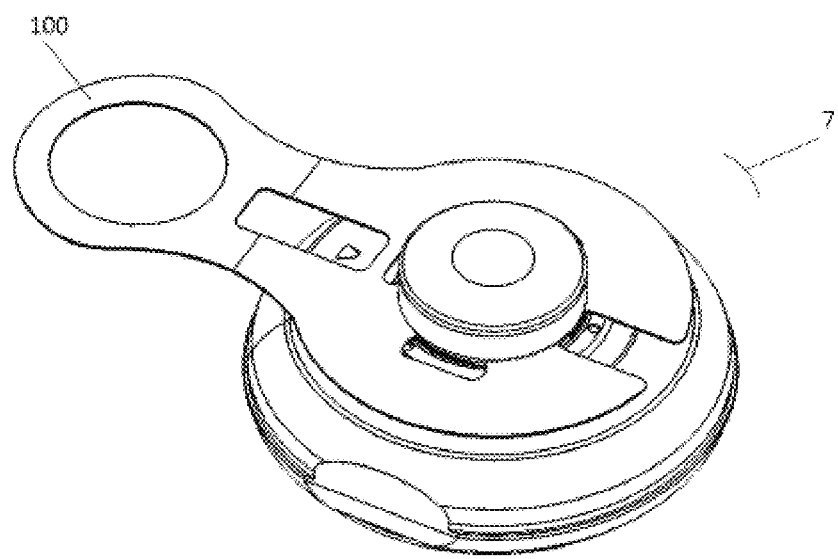
FIG. 42 shows a perspective view of an injector with the attached safety sleeve.

Referring to FIG. 42, a safety, such as a safety pin or safety sleeve 100 may be configured to allow for removal from the injector 7 in any direction to release the injector 7 to be ready to fire (inject).

Figure 43:
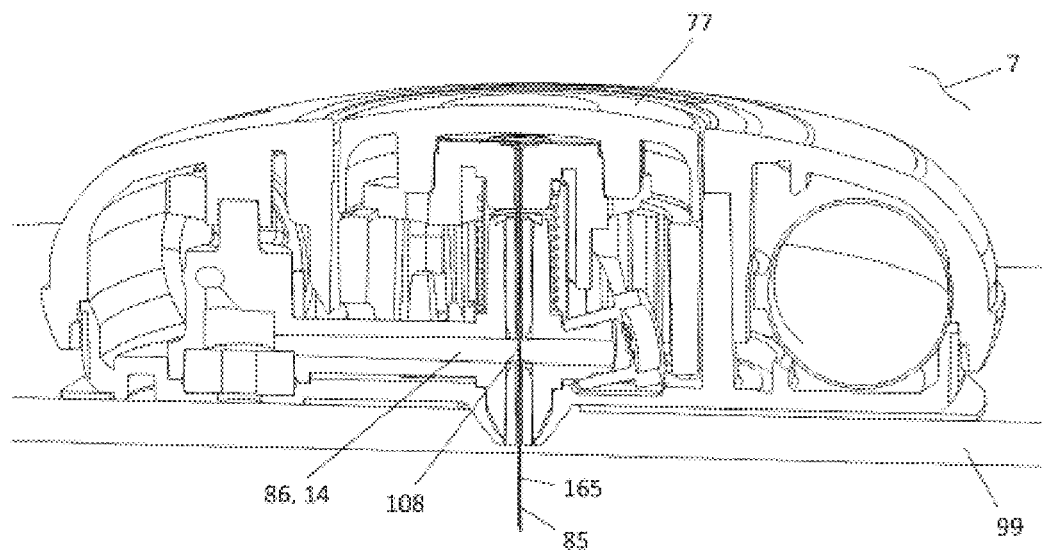
FIG. 43 shows a cross-sectional perspective of an injector with the button in second position or dispense position.

Referring to FIG. 43, the injector 7 includes a cannula 85 with a side-hole 108 that allows for fluid communication between the fluid channel 86 and the skin 99 once the button 77 is fully depressed in the injector 7. This starts dispensing of the injectable 14. The inner diameter 165 of the cannula 85 is significant in controlling the rate of dispense from the injector 7. Referencing the Hagen-Poiseuille equation for fluid flowing in a pipe, the flow rate through a pipe is directly proportional to the radius of the pipe to the fourth power. Thus, small variations in the inner diameter 165 of the cannula 85 result in large variations in flow through the cannula 85, especially as the inner diameter 165 gets smaller. The cannula 85 in the injector 7 may range from 21G to 34G (Stubs Iron Wire Gauge System) in various wall thickness configurations. This range corresponds to an inner diameter 165 range of 0.021" to 0.003", recognizing that there is manufacturing variation or tolerance with the cannula inner diameter 165 in any given cannula size. This is based on cannula size and can have an inner diameter variation as much as ±0.00075". To limit the range of the inner diameter 165 within any given cannula size and resulting variation in flow, the cannula 85 may be modified prior to assembly into the injector 7. This modification could include crimping, flattening or rolling the cannula to a new, prescribed effective inner diameter 165 over a portion of the length of the cannula 85 from a circular shape to a non-circular shape. This has the advantage of allowing for specific delivery rate control from the injector 7.

Radiofrequency Compliance Monitoring

In some instances, the injector comprises a mechanism to alert the subject, the prescriber, the healthcare provider or another third-party participant when non-compliance or non-adherence is occurring.

In accordance with further aspects of the present subject matter, when administering an injection with an automatic injector, it is desirable to know when the prescription for the injector was initially filled or refilled as well as whether the injector was used properly and on time. While many prescription drugs are tracked at the time they are filled by the patient using specialized labeling, there are limited options to confirm if the patient actually took the medication. As more drugs are being presented in injectors, the ability to automatically track prescription initiation currently has limited usage. Further, the ability to automatically track whether the injector was used properly does not exist.

As described herein, automatic tracking both for adherence and compliance can be accomplished wirelessly using RF (radio frequency) techniques installed within or in cooperative association the transfer and/or injectors described herein. Current technology allows for the use of radiofrequency identification (RFID) to transfer data, for the purposes of automatically identifying and tracking tags or microcircuit chips attached to objects. As used herein, RF or RFID or RF tags or RF chips are used comprehensively and interchangeably and are intended to include wireless electronic tags or chips for transmitting data/information using any suitable wireless communication protocol or technology, such as Bluetooth or any other wireless technology (e.g., wireless LAN, wireless PAN, or other wireless technologies described in the Institute of Electrical and Electronics Engineers (IEEE) 802 standards).

RF tags or chips may be active or passive. While both types use RF energy communicate between a tag or transponder and a reader, the method of powering the tags is different. Active RFID uses an internal power source (such as a battery) within or associated with the tag to continuously power the tag and its RF communication circuitry, whereas passive RFID relies on RF energy transferred from the reader to the tag to power the tag. In the present subject matter, the injector or the transfer package may include an RFID tag, may optionally include a power source for the tag and be read or received by an external reader. In one embodiment, the RF tag or chip is removably associated with the injector such that it can be physically removed from the injector when the injector is used. This allows for the subsequent disposal of the injector free of the limitations or restrictions that might apply if the tag or chip remained as part of the injector after its use.

Figure 44:
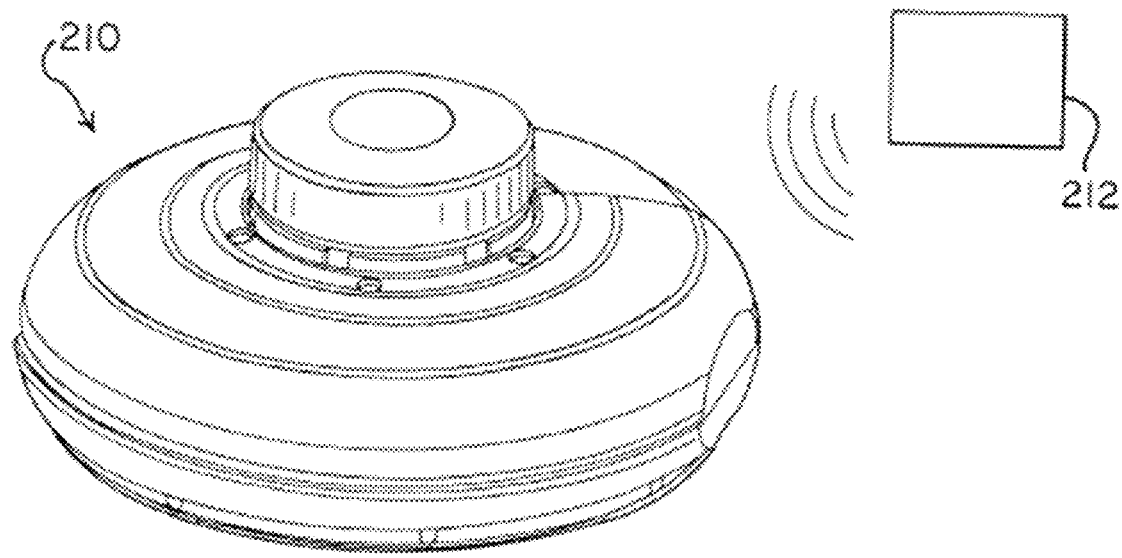
FIG. 44 shows a perspective view of an injector including a radiofrequency (RF) tag and a tag reader or interrogator.
Figure 45:
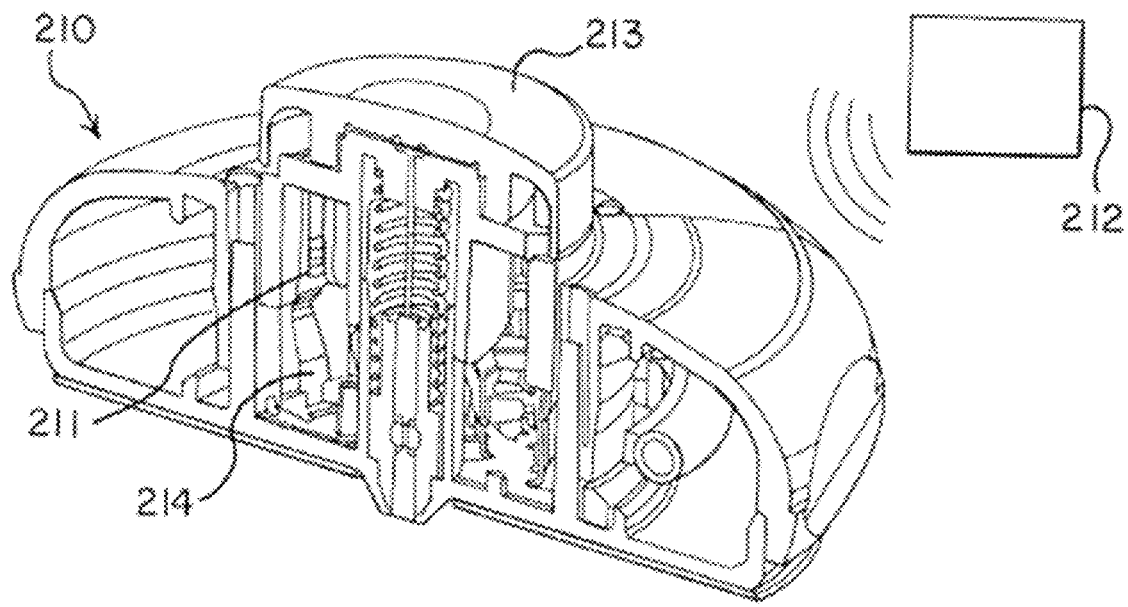
FIG. 45 shows similar to FIG. 44 but shows the injector in cross section.

Referring to FIGS. 44-45, the injector 210 may include an electronic RF tag or chip 211 to monitor the status of the injector 210. For example, the RF tag 211 may broadcast to an external reader 212 (if active) or present (if passive, read by an external reader 212) information or status—such as "the injector 210 has been prescribed," "the injector 210 has been removed from its packaging," and "the injector 210 has been actuated" and/or "the injector 210 has completed its dose." The RF tag reader could also be associated with or in communication with an on-site or off-site data collection facility, such as by wireless or hardwired connection to allow recordation and compilation of information regarding compliance.

Referring to FIGS. 44-45, an RF tag 211 may be used to monitor whether the injector 210 has been activated or has initiated or completed its dose. The injector 210 may include an active or passive radio frequency (RF) tag or chip 211 at any suitable location. As shown below, when used internally of the injector, the RF tag or chip 211 may be attached to the button 213 and in slide-able communication with the spring tabs 214 during the first and second positions of the button 213. While the RF tag 211 is in slide-able communication with the spring tabs 214, the RF tag 211 may broadcast (if active) or present (if passive, read by an external reader 212) a first state to include an unused status. In the event the injector 210 is activated, the button 213 is depressed to the dispense position. At the end of the dispense period, the button 213 is unlocked from the second depth or dispense position (shown in FIG. 45) to move up to a final position or post fire position. At this post-fire position, the RF tag 211 may no longer be in contact with the spring tabs 214, thus allowing for a change in state (second state) of the RF tag 211. In this second state, the RF tag 211 may broadcast (if active) or present (if passive, read by an external reader 212) a second state to include a used status. Alternatively the RF tag 211 may be deformed or altered in such a way upon use of the injector that, upon interrogation, the RF tag 211 presents a 'used' signature. For instance, if the RF tag consists of two coils joined by a conductor, the initial signature of the tag 211 would be the 'dual coil' signature. Once the tag 211 has been used, if the conductor joining the two coils is broken, then the two independent coils produce a different signature.

Location of the RF tab or chip outside of the injector may be desired for regulatory and/or disposability reasons. For example, the RF tag or chip 211 also may be associated with the transfer device or with another part of the system, such as for example, safety sleeve or pull tab 100 (see FIG. 42), to activate the tag or chip at a selected point or points in the operation of the transfer device and/or injector. An active RF tag or chip could, for example, be located on the safety sleeve and configured so that removal of the safety sleeve to start the injection process closes a contact between a long shelf-life battery and the tag or chip transmitter.

Figure 52:
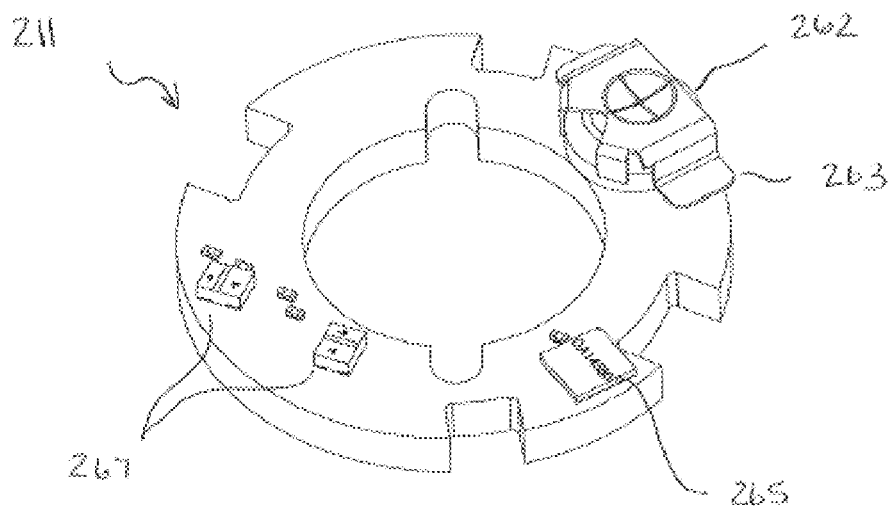
FIG. 52 shows a top perspective view of a RF chip in an embodiment of the injector of the disclosure.
Figure 53:
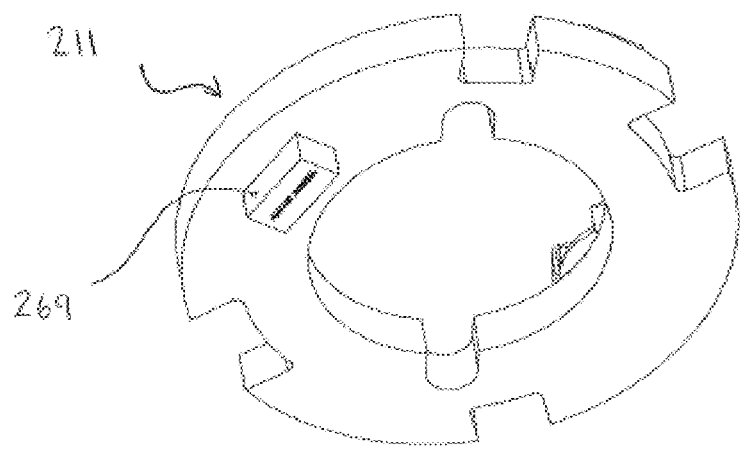
FIG. 53 shows a bottom perspective view of the RF chip of an embodiment of the present disclosure.
Figure 54:
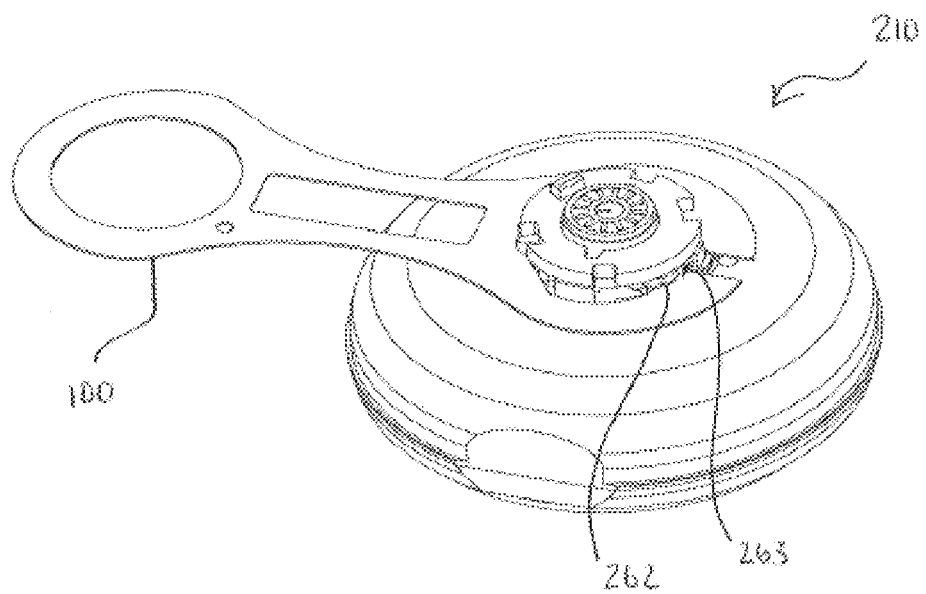
FIG. 54 shows a top perspective view of an embodiment of the injector of the disclosure with a safety tab installed.
Figure 55:
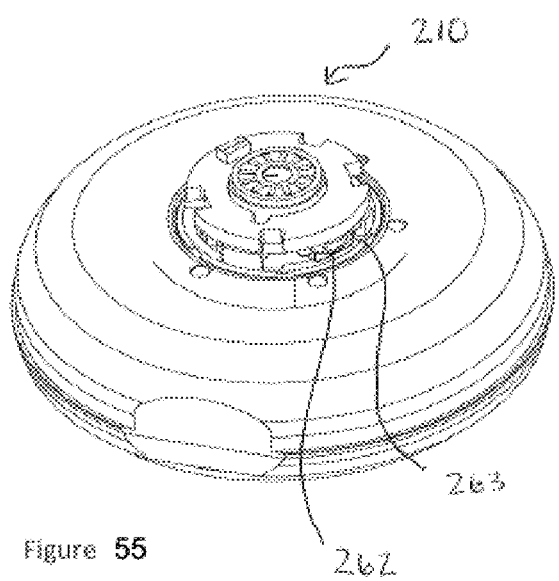
FIG. 55 shows a top perspective view of the injector with the safety tab removed.

Referring to FIGS. 52-55, the RF chip or tag 211 within the injector 210 may have two states, a standby or off state and an active, or transmitting, state. With reference to FIGS. 52 and 54, the state may be changed by making or breaking a contact between a battery 262 and a contact 263. As illustrated in FIG. 54, this may be achieved, for example, by configuring the safety release or pull tab 100 to prevent electrical contact between the battery 262 and the contact 263 by spatial separation when the pull tab 100 is in position on the injector 210. Upon removal of the pull tab 100, as illustrated in FIG. 55, the battery 262 and contact 263 come together to contact one another and make electrical contact. As a result, the RF tag begins to function. Further, different actions associated with the use of the transfer and/or injector could be employed to make or break contact. For example, a previously inactive RF tag or chip could be activated by closing a contact between a battery and the chip or tag transmitter when one action is taken, such as when a vial is inserted into the transfer device, and deactivated by another action, such as by breaking such contact after use of injector.

Figure 46:
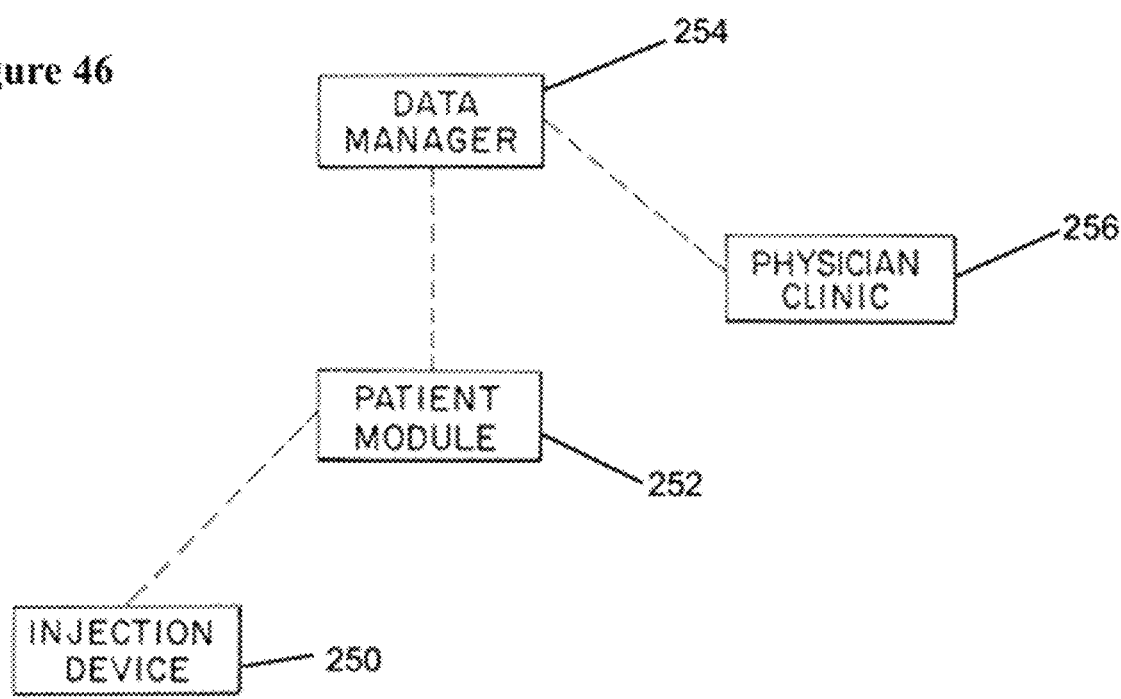
FIG. 46 shows a block diagram/flow chart, illustrating a system employing the present subject matter for monitoring patient compliance.

The RF tag or chip 211 may transmit or communicate data associated with the transfer or injector—in addition to use information. For example, the tag or chip may be configured, with memory storage capacity, to transmit the type of injector, lot number, fluid quantity administered, drug identification and other relevant information. FIG. 46 diagrammatically illustrates one system that may be employed with the present subject matter. As shown there, the RF tag or chip 250 may be of the active type, and when activated actively transmits the pertinent information to a local Patient Module 252 located within the vicinity of the patient and injector. For example, the Patient Module could be a wall-mounted or desktop device located in the patient's home for receiving the monitoring information transmitted by the RF tag or chip associated with the injector and/or transfer device. The Patient Module could also be a cellular telephone or the like.

The Patient Module could include a memory that maintains data such as patient identification and related information. The Patient Module, in turn, communicates in an appropriate manner, such WIFI, cellular communication, telephone, hard wire link or other, with a Data Manager 254, which could be any appropriate data network or Cloud storage arrangement for receiving and/or storing data received from the Patient Module indicating injector status and/or usage in association with the particular identifying patient information. The Data Manager would be accessible by medical personnel responsible for the monitoring of the patient's use of the injector and patient compliance with any prescribed injection regimen. The Data Manager could also be configured to automatically relay patient compliance information to the appropriate medical personnel, such as a particular physician or clinic 256.

Other aspects of a compliance monitoring apparatus, system and method and use with an injector such as described herein are shown in FIGS. 49-58. As illustrated there, the system may include a wireless, e.g., Bluetooth, source, such as a battery powered sending unit such as a microchip, indicated at 262 in FIG. 59. The sending unit may be mounted in any suitable location, and can be associated with or attached to a part of the injector (an/or transfer device) in a manner so that it can be detached from the injector or transfer device at the time of disposal—allowing most of the injector or transfer device structure to be recycled, as electronic circuitry and electronic chips are typically not similarly recyclable.

In some embodiments, a contactor ring is provided in the top of the of the injector housing and is prevented from making contact with sensing leads (which are attached to the injector button) when a safety strip is installed. When the safety strip is removed, the contactor ring of the housing makes contact with the sensing leads of the button. Different sequences of the injection process may then be tracked based on the connection status between the contactor ring and the sensing leads (i.e. position of the contactor ring with respect to the sensing leads). Infrared sensors may also be embedded in the injector to optically track delivery progress, such as by, for example, monitoring of the position of, or amount of injectable fluid in, expandable member of the injector.

Referring to FIGS. 52 and 53, an embodiment of the RF tag or chip 211 includes the following components: Battery 262, Contact 263, Bluetooth Module with Microcontroller/Microprocessor 265, Button Sensors 267 and Antenna 269. The battery 262 provides for the stored energy to power the system. This can be a coin-cell battery or equivalent in the voltage range of 1.5-3V with a power output of 5-100 mAh. As explained previously, the contact 263 provides the electrical connection between the battery 262 and the RF tag or chip 211. The contact 263 is configured to interact with the pull tab 100 to allow for no electrical contact until the time of use when the user removes the pull tab 100. The Bluetooth module 265 has an integrated microcontroller/microprocessor. An example of a suitable Bluetooth module is Dialog Semiconductor Part number DA14580-01UNA. In alternative embodiments, the Bluetooth module may be separate from the microcontroller/microprocessor.

Figure 56:
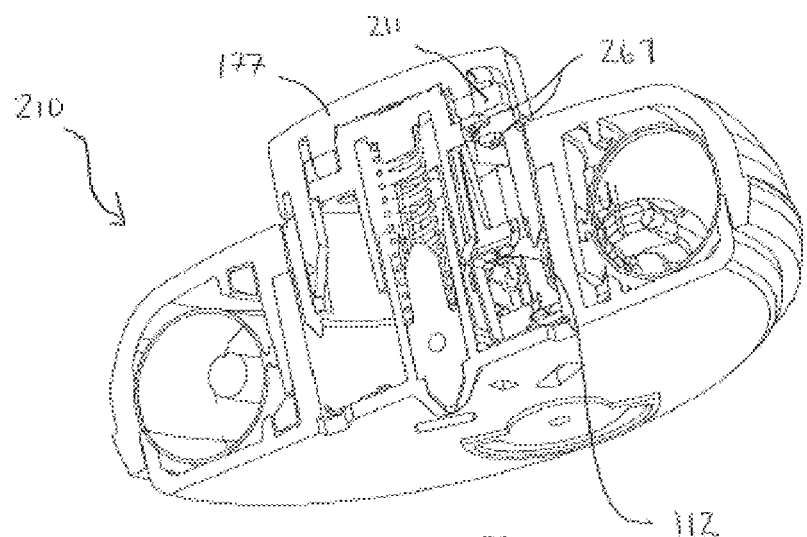
FIG. 56 shows a cross-sectional view of the injector showing the push button in the raised, extended, or up position.
Figure 57:
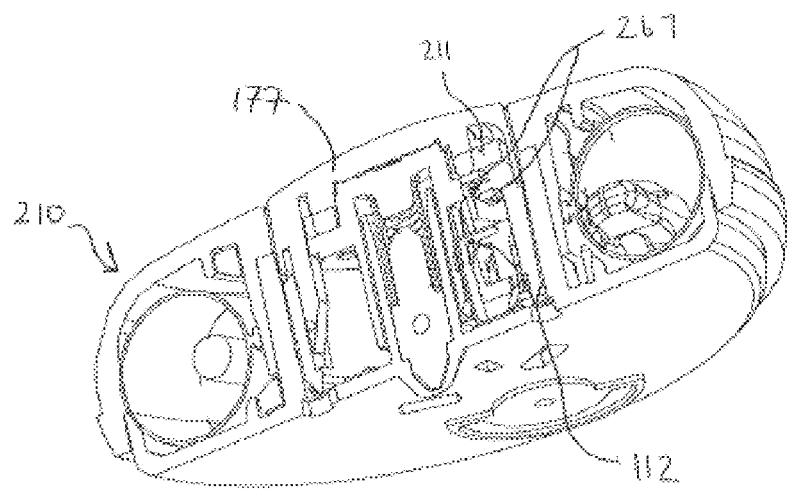
FIG. 57 shows a cross-sectional view of the injector showing the push button in the lowered, retracted or down position.

The button position sensing system in an embodiment of the device is illustrated in FIGS. 56 and 57. The sensing system can use an infrared emitter and receiver sensor combination 267. The RF chip 211 is mounted to an underside surface of the device button 177 with the sensors 267 facing downwards. A reflecting member 112 is mounted to the bottom of the injector in a fixed fashion. When the device button is actuated so as to move from the up, raised or extended position illustrated in FIG. 56 to the down, lowered or retracted positioned illustrated in FIG. 57, the sensors 267 detect the decrease in distance from reflecting member 112. Conversely, when the button is released after delivery of the drug so that it moves from the position of FIG. 57 to the position of FIG. 56, the sensors 267 detect the increase in distance from reflecting member 112. The sensors 267 transmit this button position information to the microcontroller/microprocessor module 265.

Figure 58:
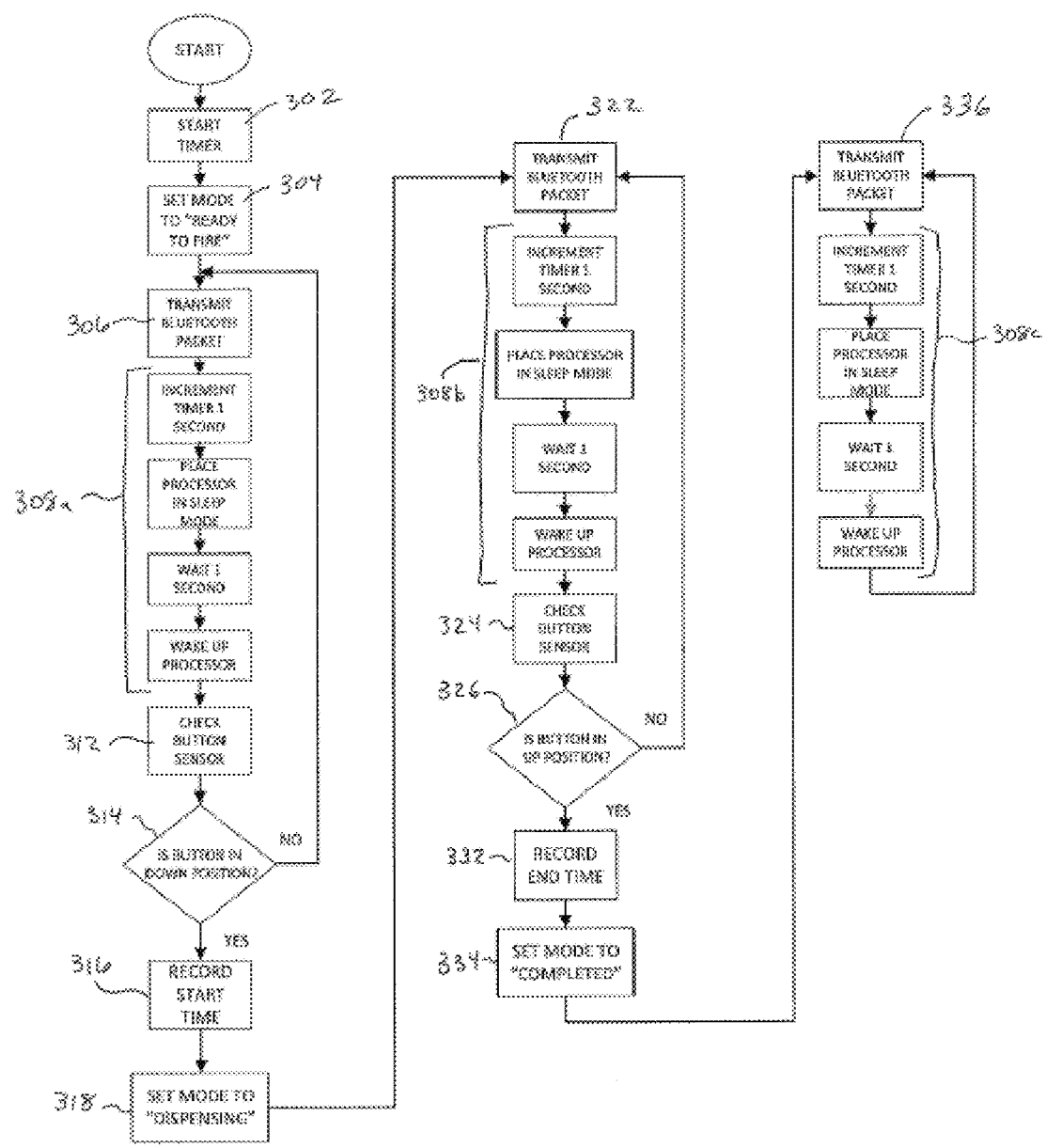
FIG. 58 shows a flow chart showing processing performed by a microcontroller/microprocessor in an embodiment of the injector of the disclosure.

The processing performed by the microcontroller/microprocessor module 265 in an embodiment of the device is presented in FIG. 58. A start timer, indicated at block 302, is initiated when the microcontroller/microprocessor is powered up, such as by removal of the safety tab 100 as described with reference to FIGS. 54 and 55 above. The mode or status of the device is then set to "Ready to Fire" (i.e. ready to dispense) as indicated by block 304 and a Bluetooth packet indicating this mode for the device is transmitted to a Bluetooth-enabled remote reader or receiver (such as 212 of FIGS. 44-45), which may be, as examples only, a smart phone or a computer system. The mode is displayed on the remote receiver to a user.

The processing of blocks 308a can then performed to conserve the battery life of the device and compute timing of the device.

The microcontroller/microprocessor then checks the position of the device button (177 in FIGS. 56 and 57), as indicated by block 312 using, for example, IR sensors as described above with reference to FIGS. 56 and 57. As indicated at 314, the above processing is repeated if the device button has not been pressed into the down position.

If the device button has been pressed down, a start time for the delivery of the injectable is recorded, as indicated by block 316, and the device mode is set to "Dispensing", as indicated by block 318. This mode is transmitted to the remote receiver, as indicated by block 322, where it is displayed to the user.

The processing of blocks 308b is then performed to conserve the battery life of the device and compute timing of the device by intermittently or alternately placing the processor in a low energy sleep mode and then awakening the processor at one second (or other suitable time) intervals.

The microcontroller/microprocessor then checks the position of the device button, as indicated by block 324. As indicated at 326, the above processing beginning with block 322 is repeated if the device button has not returned to the raised or up position. If the device button has moved into the up position, an end time for the delivery of the injectable is recorded, as indicated by block 332, and the device mode is set to "Completed", as indicated by block 334. This mode is transmitted to the remote receiver, as indicated by block 336, where it is displayed to the user.

The processing of blocks 308c is then performed to conserve the battery life of the device and compute timing of the device, after which the "Completed" status of the device is again transmitted to the remote receiver (block 336).

Embodiments of the disclosure may provide 'smart' connected devices that enable patients to self-administer high volume/viscosity drugs, enabling and promoting patient freedom and mobility. Embodiments may provide the user with a safe, simple, and discreet drug delivery experience.

Embodiments of the disclosure may provide a smart device system to provide three pieces of information about the operation of the drug delivery system: 1) When the device is powered on, 2) when the device has started delivery and 3) when the delivery has been completed. The user interaction in some embodiments can comprise opening the mobile application on their device, as described elsewhere herein, and the smart device will do the rest without requiring additional operations from the subject or user.

Embodiments of the disclosure may provide advantages such as: small board footprint—the entire electronics package fits inside the existing button and is less than ⅜-inch (9.5 mm) in diameter. This allows for easy removal of the electronics (button) for electronic disposal and recyclability.

Embodiments of the disclosure may include smart device technology in the transfer device. For example, the transfer device may include electronics to track the usage of the transfer device. The electronics in the transfer device could communicate directly with an external receiving device and/or to the electronics in the patch/injector. Transducers/sensors within the transfer device electronics could provide information including but not limited to environmental conditions, opening of the outer box or packaging, removal of the transfer device from the outer packaging, orientation of the transfer device (tilt sensing), the position of the device (e.g., using a global positioning system, or GPS) whether the transfer device is located on a flat surface, vial insertion, plunger release (venting), and/or removal of the injector from the transfer device. Electronics in the transfer device could determine if the correct vial has been inserted based electronics within the vial or reading of bar codes/QRG codes. Activation of the electronics could occur when the outer box or packaging is opened, when the transfer device is removed. Additional electronics could be added to vibrate or make a sound if the device is not placed on a table or at an angle. The electronics in conjunction with an external receiver could provide voice commands to aid the user in using the device or provide instruction if something is done incorrectly.

In certain embodiments of the disclosure, the injector may utilize Bluetooth communications to provide data to the user. Furthermore, embodiments may integrate Bluetooth Low Energy (BLE) into the device. BLE can be designed for low power, low cost applications that require lower data throughput rates than traditional Bluetooth connections such as audio streaming or hands-free phone connections.

There are two major types of connections defined in the Bluetooth standard: Standard (bonded) mode and Broadcast (also known as "beacon") mode. In standard or bonded connections, a host (smartphone with installed app) creates a saved connection with a peripheral (i.e., a smart device). In this scenario, through the pairing process, both the host and the peripheral share data to create a permanent connection that allows sharing between only one host and one peripheral. This method has the advantage of a secure connection allowing the exchange of encrypted information that cannot be decoded without the encryption key.

In broadcast mode (also called a "beacon"), the peripheral sends out data at regular intervals that can be read by any nearby host. In this scenario, the peripheral only broadcasts data; data is never received. There are several advantages to this mode, e.g., reduced power consumption. In some instances, further power savings can be achieved through lower power 'sleep' mode, waking up only when new data needs to be broadcast;

Additionally, as the peripheral can be configured to be a transmit-only device, enhanced security is provided as the hardware cannot be 'hijacked' or loaded with malicious software. This reduces or eliminates the risk of unauthorized remote control of the device. The software is loaded onto the device in the factory, preventing unauthorized alteration once deployed.

In some instances, installation of an application, as described elsewhere herein, may be used for securing data privacy. For instance, without proper application installation, the data can simply consist of an unusable list of binary numbers, lacking any text or other readable identifiers. Because of this, the lack of an encrypted connection does not expose any sensitive user information. The data may also exclude patient information—such as names or identification numbers—which could be associated with a specific individual (thereby following HIPAA Compliance).

An important attribute of the connected healthcare implementation within embodiments of the disclosure may be that it does not affect the essential performance functions of the drug delivery device. In some embodiments, this feature of the device only reports the status of the device and in no way alters the function of the drug delivery device. Even in the event of a critical failure of the Bluetooth components, such as the battery, some embodiments of the device will complete the delivery of the drug and provide the user with visual feedback as to the device status.

Utilizing the Bluetooth Low Energy broadcast mode and through an electronic chip in the button of the device, some embodiments of the disclosure can deliver real-time device performance information in a small, low cost, convenient package.

Injector with Patch

In an aspect, the present disclosure provides a system for measuring a plurality of health or physiological parameters from a subject. The system may comprise a patch comprising a first housing having a plurality of sensors configured to (i) measure the plurality of health or physiological parameters from the subject when the patch is secured to a body of the subject, and (ii) provide one or more outputs corresponding to the plurality of health or physiological parameters from the subject. The first housing may comprise an opening. The system may also include an injector having a second housing comprising a cannula in fluid communication with a fluid flow path. The second housing may be coupled to the first housing such that the cannula is directed through the opening and in contact with a body of the subject when the patch is secured to the body. The injector may be configured to (i) direct a substance from a reservoir to the fluid flow path in fluid communication with the reservoir, and (ii) direct the substance from the fluid flow path into the subject through the cannula.

The cannula may be configured to extend towards or retract away from the body of the subject. In some examples, the cannula extends towards the body of the subject to deliver the substance into the body of the subject (e.g., across a skin of the subject). Subsequent to delivery of the substance, the cannula may retract away from the body of the subject. The cannula may be connected to the reservoir via a fluid flow path. The cannula may extend to and/or retract from the body using a variety of mechanisms, e.g., mechanical, electrical, etc. The means for cannula extension and retraction may comprise pumps, springs, gears, diaphragms, screws, or other means to move the cannula, or variations or combinations thereof.

The injector may be detachable from the patch. The patch may comprise a first housing, and the injector may comprise a second housing, and the first and second housing may be removably coupled. In one example, the first housing of the patch may be mechanically coupled to the second housing of the injector using one or more fastening mechanisms. In some cases, the first housing and/or the second housing may comprise magnets that allow for removable coupling, as described elsewhere herein. In another example, the first housing and the second housing may be adhered, e.g., using adhesive tape. The adhesive force of the first housing and the second housing may be modulated based on desired properties. For example, it may be desirable to maintain the patch on the body of the subject while removing the injector. In such examples, an adhesive layer can be added to the patch that may facilitate securing of the patch to the body of the subject. This body-adhering adhesive layer may have a stronger adhesive force between the patch and the body of the subject than the adhesive force between the patch and injector. In yet another example, the first housing and the second housing may be mechanically coupled, e.g., using interlocking geometries of the first housing and the second housing. For example, the first housing may comprise threads (e.g., screw threads, internal threads, etc.) and the second housing may comprise complementary threads that may engage with the threads of the first housing. In conjunction or alternatively, the first housing and/or the second housing may comprise snap-fit joints (e.g., cantilever snap fits, annular snap fits, etc.) that allow for interlocking of the first housing to the second housing. Alternatively, or in conjunction, the first housing and/or the second housing may comprise components that allow for interference fits, force fits, shrink fits, location fits, etc. Other examples of fastening mechanisms may include, in non-limiting examples, form-fitting pairs, hooks and loops, latches, threads, screws, staples, clips, clamps, prongs, rings, brads, rubber bands, rivets, grommets, pins, ties, snaps, Velcro, adhesives (e.g., glue), tapes, vacuum, seals, a combination thereof, or any other types of fastening mechanisms. Alternatively, the injector may be permanently attached to the patch. For example, the first housing may be connected to the second housing or may be monolithically built into the second housing, or vice-versa.

In some instances, the patch and the injector can be fastened to each other via complementary fastening units. For example, the patch and the injector, or the housing of the patch and the housing of the injector, can complete a form-fitting pair. The patch can comprise a form-fitting male component and the injector can comprise a form-fitting female component, or vice versa. In some instances, an outer diameter of a protrusion-type fastening unit of the patch can be substantially equal to an inner diameter of a depression-type fastening unit of the injector, or vice versa, to form an interference fit. Alternatively, or in addition, the patch and the injector can comprise other types of complementary units or structures (e.g., hook and loop, latches, snap-ons, buttons, nuts and bolts, magnets, etc.) that can be fastened together. Alternatively, or in addition, the patch and the injector can be fastened using other fastening mechanisms, such as but not limited to staples, clips, clamps, prongs, rings, brads, rubber bands, rivets, grommets, pins, ties, snaps, Velcro, adhesives (e.g., glue), magnets or magnetic fields, tapes, a combination thereof, or any other types of fastening mechanisms.

In some instances, the patch and the injector can be fastened to each other via an intermediary structure. In some instances, the intermediary structure may be fastened to one or both of the patch and the injector through one or more of any of the fastening mechanisms described herein. The intermediary structure may comprise a solid material, semi-solid material, liquid material (e.g., a resin that is configured to solidify), or multiple material types. In some instances, the intermediary structure may undergo phase transitions (e.g., liquid to solid for an adhesive). For example, the intermediary structure may comprise a fluid adhesive that solidifies to achieve the fastening. In some instances, the intermediary structure may be capable of transforming from a first phase to a second phase, such as from liquid to solid or from solid to liquid, upon application of a stimulus (e.g., thermal change, pH change, pressure change, applied force, etc.) to achieve fastening or unfastening (or both). In some instances, the patch and/or the injector may comprise the intermediary structure. For example, the intermediary structure may be integral to the patch and/or the injector.

The fastening between the patch and the injector can be temporary, such as to allow for subsequent fastening and unfastening of the patch and injector without damage (e.g., plastic deformation, shear deformation, wear, compression deformation, etc.) to the patch or injector. Alternatively, the fastening can be permanent, such as to allow for subsequent unfastening of the two patches from the injector. In some cases, it may be desirable to deform either the patch or injector, and either the patch or injector may temporarily or permanently be deformed (e.g., stretched, compressed, etc.) and/or disfigured (e.g., bent, wrinkled, folded, creased, etc.) or otherwise manipulated when fastened to the injector or patch. The opening may comprise a pierce-able membrane. The pierce-able membrane may be pierced by the cannula to generate the opening. The pierce-able membrane may be formed of a polymeric material, or the pierce-able membrane may be formed of multiple polymeric materials. The polymeric materials may be naturally occurring or may be synthetic. Non-limiting examples of polymeric materials include poly vinyl chloride (PVC), polyethylene, polyurethane. In some cases, the pierce-able membrane may further comprise an adhesive layer (e.g., acrylate, methacrylate, epoxy diacrylate, or other vinyl resins, etc.). In some cases, the pierce-able membrane may comprise a self-healing polymer or elastomeric material, such that the opening that is introduced by the cannula may be closed, e.g., after cannula retraction. In such cases, the pierce-able membrane may include an opening, e.g., hole or slit that is configured to form a seal in the absence of the cannula directed through the opening. In some examples, the pierce-able membrane may include an opening that is not configured to seal in the absence of the cannula directed through the opening. Alternatively, the opening may not comprise a pierce-able membrane and the opening may be configured to be in direct line of sight with the body of the subject. The opening may be any suitable shape, e.g., a slit, triangular, square, rectangular, rhombus, pentagonal, hexagonal, heptagonal, octagonal, polygonal, ellipsoid, annular, circular, etc. In some cases, the pierce-able membrane comprises an absorbent material, e.g., cotton, rayon, nylon, a polymer, a polymer blend, etc. In such cases, the pierceable membrane may be used as a bandage and can collect bodily fluids (e.g., sweat, blood, etc.) from the body of the subject. In some instances, the pierceable membrane may comprise an oxygen-permeable material, which may allow for exposure of the body of the subject, or portion thereof, to the ambient air. In some cases, the pierceable membrane may comprise a medicament (e.g., analgesic or medicament for treating pain).

The reservoir may be secured to the injector. In some cases, the reservoir is removable from the injector. For example, the reservoir may comprise a container or be a part of a container. The reservoir container may be removably coupled to the injector (e.g., attach and detach from the housing of the injector). The housing may contain fasteners to secure the reservoir. Alternatively, the geometry of the injector may be designed to fit the reservoir or reservoir container. In other cases, the reservoir may be part of the injector (i.e., not removable). In one example, a medicament reservoir may be provided in the housing and may be in fluid communication with the injection cannula. For example, the injection cannula may be moveable within the housing between a pre-dispense position and a dispense position in fluid communication with the reservoir. The reservoir may be configured to contain a formulation having the substance.

The substance may comprise a medicament. The medicament may be a solution or a mixture. The medicament may be used for treating diseases in a range of therapeutics areas including but not limited to cardiovascular, musculoskeletal, gastrointestinal, dermatology, immunology, ophthalmology, hematology, neuroscience, oncology, endocrinology/metabolic and respiratory. The medicament may be used to treat discomfort or pain of the subject. For instance, the medicament may comprise an analgesic, non-steroidal inflammatory drug (NSAID), or other pain-reducing, pain-alleviating, or other pain management substance.

The housing of the patch and/or the housing of the injector may comprise one or more polymer or plastic materials. Non-limiting examples of polymers include polyamides, polycarbonate, polyester, polyethylene, polypropylene, polystyrene, polyurethane, polyvinyl chloride, polyvinylidene chloride, acrylonitrile butadiene styrene, polymethyl methacrylate, polytetrafluoroethylene, polyimide, polylactic acid, phenolics, polyetheretherketone, or derivatives thereof (e.g., highly cross-linked, high density, etc.). The housing of the patch and/or the housing of the injector may comprise a single polymer type (e.g., a homopolymer) or more than one polymer type (e.g., a copolymer) and comprise a random or arranged organization of monomers. For example, a polymer may be a block polymer, an alternating copolymer, periodic copolymer, statistical copolymer, stereoblock copolymer, gradient copolymers, branched copolymers, graft copolymers, etc.

A sensor and/or transducer may comprise one or more sensors or transducers that allows for measuring or monitoring a health or physiological parameter or a plurality of health or physiological parameters or allow for indication of device function to the subject. Alternatively or in conjunction, one or more sensors may allow for measuring of patch or injector parameters. Non-limiting examples of patch or injector parameters include determination of whether the patch is secured (e.g., to a body of the subject), whether the patch or injector is in communication with the communication interface, whether the cannula is in fluid communication with the reservoir, occlusion of the cannula, whether the patch and injector are properly coupled, flow rate of the substance through the cannula, etc. A sensor of the plurality of input transducer/sensors may be selected from the group consisting of a conductivity sensor, impedance sensor, capacitance sensor, charge sensor, humidity and/or moisture sensor, temperature sensor, heart rate sensor, interstitial pressure sensor, resistance sensor, distension sensor, acoustic sensor, vibration sensor, blood pressure sensor, optical sensors (e.g., color sensor, light sensor, wavelength sensor), chemical sensor, movement and/or activity sensor, and a substance-tracking sensor. A sensor of the plurality of output transducers may be selected from the group consisting of haptic(vibration) transducers, audio transducers or visual transducers. These sensors may be used to detect, in non-limiting examples, the environmental conditions in which the subject is using the injector, the subject's body temperature, heart rate, blood pressure, interstitial pressure, tissue density, skin distension, bleeding (e.g., internal or external), delivery of the medicament, dosage of the medicament to deliver and/or delivered to the subject, sweat quantity of the subject, and/or a plurality of analyte measurements from the subject (e.g., blood glucose, blood oxygen, etc.). One or more measurements may be measured or monitored prior to, contemporaneously, or following securing of the patch. For example, the patch may be configured to measure one or more health or physiological parameters prior to injection to establish a baseline and/or calibration measurement of the one or more health or physiological parameters. The patch may be secured to the body of the subject separately from the injector. For example, the patch may be secured to the body of the subject and one or more measurements may be collected. Subsequent attachment of the injector (e.g., to the patch and/or the body of the user) may then allow for directing a substance to the subject.

The transducer may comprise any useful components, e.g., a solenoid, motor, or micro-electro-mechanical systems (MEMS) actuator. In such cases, the housing of the injector or patch may comprise electrically conductive contacts providing both mechanical attachment and electrical contact of the transducers or sensors, e.g., in an electronic subsystem housed in the injector.

The patch and/or injector may comprise a communication interface that allows for transmitting and/or receiving data corresponding to the plurality of health or physiological parameters of the subject and/or parameters of the patch or injector. The data may be transmitted to an electronic device in communication with the communication interface. The communication interface may be a wireless communication interface, a Wi-Fi interface, a near-field communication interface, or a Bluetooth interface, as described herein. The electronic device may be a device that may communicate with the communication interface, e.g., a mobile device (e.g., smart phone, tablet, laptop, etc.). Alternatively, the communication interface may be a wired communication interface. In some examples, the patch and/or injector may comprise a port for communication and/or power supply (e.g., universal serial bus (USB), USB-type C, etc.) for connection to the electronic device. The patch and/or injector may include an RFID tag that allows for information to be transferred to and optionally, recorded by the injector and/or patch including but not limited to information about the drug. This may allow data transmitted about the injection to include information about the device and the drug.

In some cases, the patch, injector, and/or electronic device may comprise methods for data processing, data storage, and/or one or more feedback loops. In one such example, the patch may monitor one or more physiological parameters of the subject after injection to produce data on the one or more physiological parameters of the subject. The data may be transmitted through the communication interface to the electronic device (e.g., mobile device). In some cases, the mobile device may comprise a method for processing the data and/or storing data (e.g., in computer readable memory). Examples of processing include measurement of a concentration of an analyte, identification of an analyte, comparing the concentration of an analyte to a standard, calibration of the measurement, summaries of information collected, statistics calculation, trend determination, etc. The processed data may subsequently be used to regulate, e.g., in a feedback loop, to regulate one or more parameters of the patch or injector. The processed data may also be sent directly to a third party for further evaluation. For example, a measurement of the physiologic parameter may measure the concentration of an analyte or a substance (e.g., a drug or medicament). The data may be transmitted to the electronic device, which may further process the data (e.g., calibrate the concentration, compare to a standard, determination if a dosage change is required etc.). Accordingly, the processed data may be used to change a device parameter, e.g., dosage of the substance to be administered, flow rate of dispensing of the substance, etc. The data, processed data, or other signal may then be relayed back to the patch or injector, such that the subsequent injection of the injector is modulated (e.g., the next dosage is higher or lower). In another example, a measurement of the physiologic parameter may measure patient bleeding (e.g., colorimetric, measurement of heme iron of blood, etc.). Detection of bleeding or substance leakage from the site may be used to modulate (e.g., in a feedback loop) the subsequent administration rate or injection. In such examples, presence of patient bleeding may allow for subsequent injections to be delayed, or to change a parameter of the cannula extension toward the body of the subject (e.g., force of injection, speed of injection, etc). In some cases, an electronic device may not be required, and the patch may be able to communicate with the injector directly or through a communication interface. In such cases, the patch and/or injector may measure a device and/or physiological parameter of the subject and subsequently use the measurement to regulate a parameter of the injector or patch. In one non-limiting example, the measurement of the parameter (e.g., blood glucose of the patient) may regulate the dosage of a subsequent injection of the injector.

In another example, the patch may monitor one or more parameters of the patch and/or injector to produce data on the one or more parameters of the injector and/or patch. The data may be transmitted through the communication interface to the electronic device (e.g., mobile device). In some cases, the mobile device may comprise a method for processing the data. Examples of processing include determination if device is properly secured (e.g., if the adhesion force of the patch to the body of the subject is above or below a threshold value), whether the patch is properly connected to the injector, etc. The processed data may subsequently be used to regulate, e.g., in a feedback loop, one or more parameters of the patch or injector. For example, a measurement of the adhesion force of the patch to the body of the subject may be conducted. The data may be transmitted to the electronic device, which may further process the data (e.g., determine insufficient adhesion force). Accordingly, the processed data may be used to change a device parameter, e.g., activation a notification to the subject or other user, as described herein. The data, processed data, or other signal may then be relayed back to the patch or injector, such that a parameter of the patch or injector is adjusted or requires adjustment before proceeding to inject again (e.g., administer another dosage of the substance). In some cases, an electronic device may not be required, and the patch may be able to communicate with the injector directly or through a communication interface. In such cases, the patch and/or injector may measure a parameter of the patch and/or injector and subsequently use the measurement to regulate that parameter or a different parameter of the injector or patch. In one non-limiting example, the measurement of an insufficient adhesion force of the patch may, in a feedback loop, prevent subsequent injection of the injector until the patch is measured as sufficiently adhered to the body of the subject.

The patch and/or injector may also be in communication or be capable of communication with the subject or other user. In some cases, the communication with the subject or other user may comprise a feedback system or loop. Alternatively, or in conjunction, the patch or injector may be capable of notifying the subject or other user (e.g., physician, nurse, medical practitioner, clinician, etc.) on a device parameter, health or physiological parameter, or both. For example, the patch or injector may be capable of producing sounds (e.g., to give directions to the subject or other user), producing motion (e.g., vibration), or may comprise visual indicators such as a light (e.g., light-emitting diode), a screen or display (e.g., a liquid-crystal display (LCD), organic light-emitting diode, quantum dot display, or variations or derivatives thereof), or other visual indicator. Alternatively, or in conjunction, the patch or injector may comprise a user interface module. In such examples, the subject or other user may be able to interact with the patch and/or injector. In one of such examples, the patch or injector may comprise a screen or display that may produce a string of characters or sounds that may be used to prompt the subject or other user to respond to a command. In another example, the patch or injector may comprise a screen or display that may produce a string of characters or sounds that may be used to display an output or result, such as the results of the measurement of a physiological parameter. The subject or other user may then be able to input a response or a command, e.g., through a microphone, which may be in the housing of the patch and/or injector, or through a button on the housing of the patch or the injector with which the subject can interact. In some cases, the subject's input into the patch or injector may result in modulation of a parameter of the patch or injector. In some cases, the subject or other user may be able to input a parameter, e.g., pain, discomfort, etc., that may not be easily measurable or accessible from the patch or injector. These parameters may then be communicated, e.g., through a communication interface, to an external device (e.g., mobile device). In some cases, the patch and/or injector may comprise feedback systems such that the input from the subject or other user may modulate a parameter of the patch or injector. For example, input of a pain parameter may result in modulation of the flow rate of the substance through the cannula or the frequency of administered doses of the sub stance.

The patch and/or injector may also be configured to communicate with a remote system. In some examples, the patch and/or injector may measure one or more physiological parameters of the subject or one or more parameters of the patch and/or injector to produce data on the one or more physiological parameters of the subject or the one or more parameters of the patch and/or injector. The data may be transmitted to a remote server, a distributed computing network (e.g., for cloud computing). Processing of the data may then occur separately from the patch and/or injector. In some cases, the processed data may then be transmitted to an electronic device (e.g., mobile device). In other cases, the processed data may then be transmitted to the patch and/or injector, for modulation of a parameter of the patch and/or injector. Transmission of data to a remote server and/or to an electronic device may allow for the subject to monitor the one or more physiological parameters, and/or may additionally or alternatively allow for physicians or caretakers to also monitor the one or more physiological parameters of the subject.

In another aspect, provided herein is a method for measuring a plurality of health or physiological parameters from a subject. The method may comprise (a) providing: (i) a patch comprising a first housing having a plurality of sensors and comprising an opening, and (ii) an injector having a second housing comprising a cannula in fluid communication with a fluid flow path. The second housing may be coupled to the first housing of the patch, and the injector may comprise a reservoir comprising a substance and a fluid flow path in fluid communication with the reservoir. The method may further comprise (b) securing the patch to a body of the subject; (c) when the patch is secured to the body of the subject, directing the cannula through the opening to (i) direct the substance from the reservoir to the fluid flow path, and (ii) direct the substance from the fluid flow path into the subject through the cannula; and (d) using the plurality of sensors to (i) measure the plurality of health or physiological parameters from the subject, and (ii) provide one or more outputs corresponding to the plurality of health or physiological parameters from the subject.

Using embodiments of the disclosure, a person with any number of physical and/or mental conditions treatable with drugs administered with an injector, such as the devices described above, can be monitored to ensure that the combination therapy (medicament and injector) is safe and efficacious. Data collected during monitoring of the patient and injector attributes can be used by patients, caregivers, providers, payers, drug and device manufacturers to provide feedback to any of the aforementioned parties including confirmation of claims/outcomes and allowing for manual and/or automatic intervention by the patient and/or device to improve the safety and effectiveness of the therapy.

Figure 59:
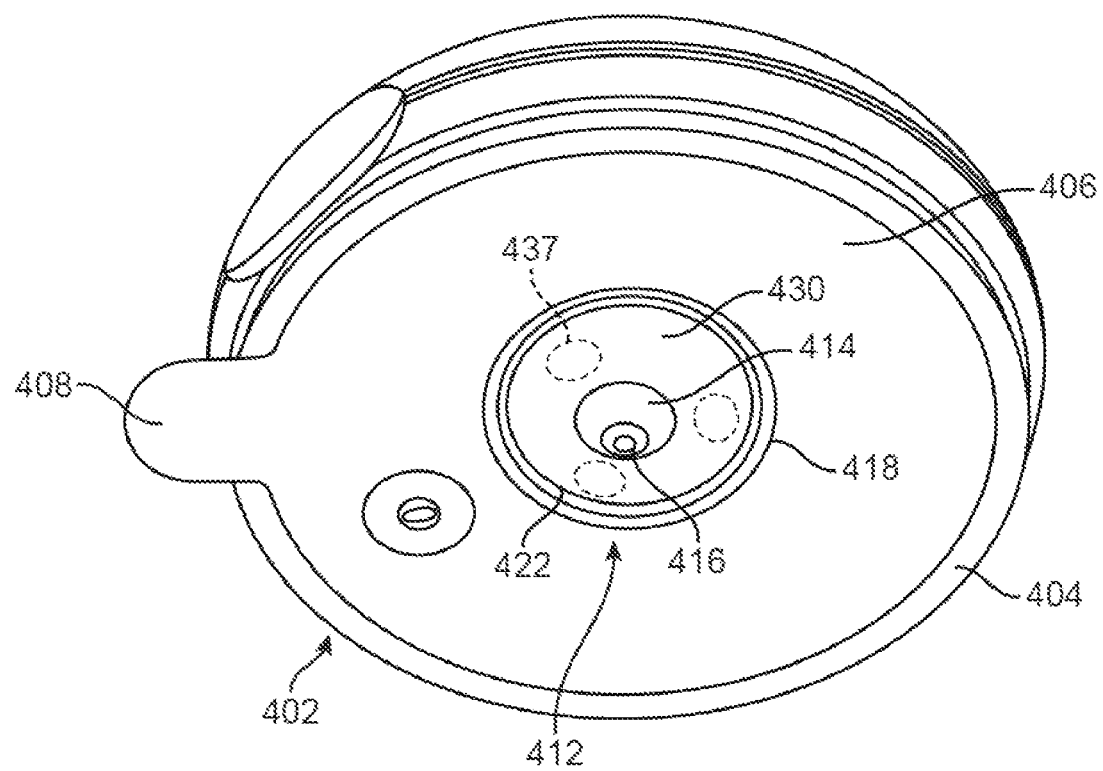
FIG. 59 shows bottom perspective view of an injector with detachable patch in an embodiment of the disclosure.
Figure 60:
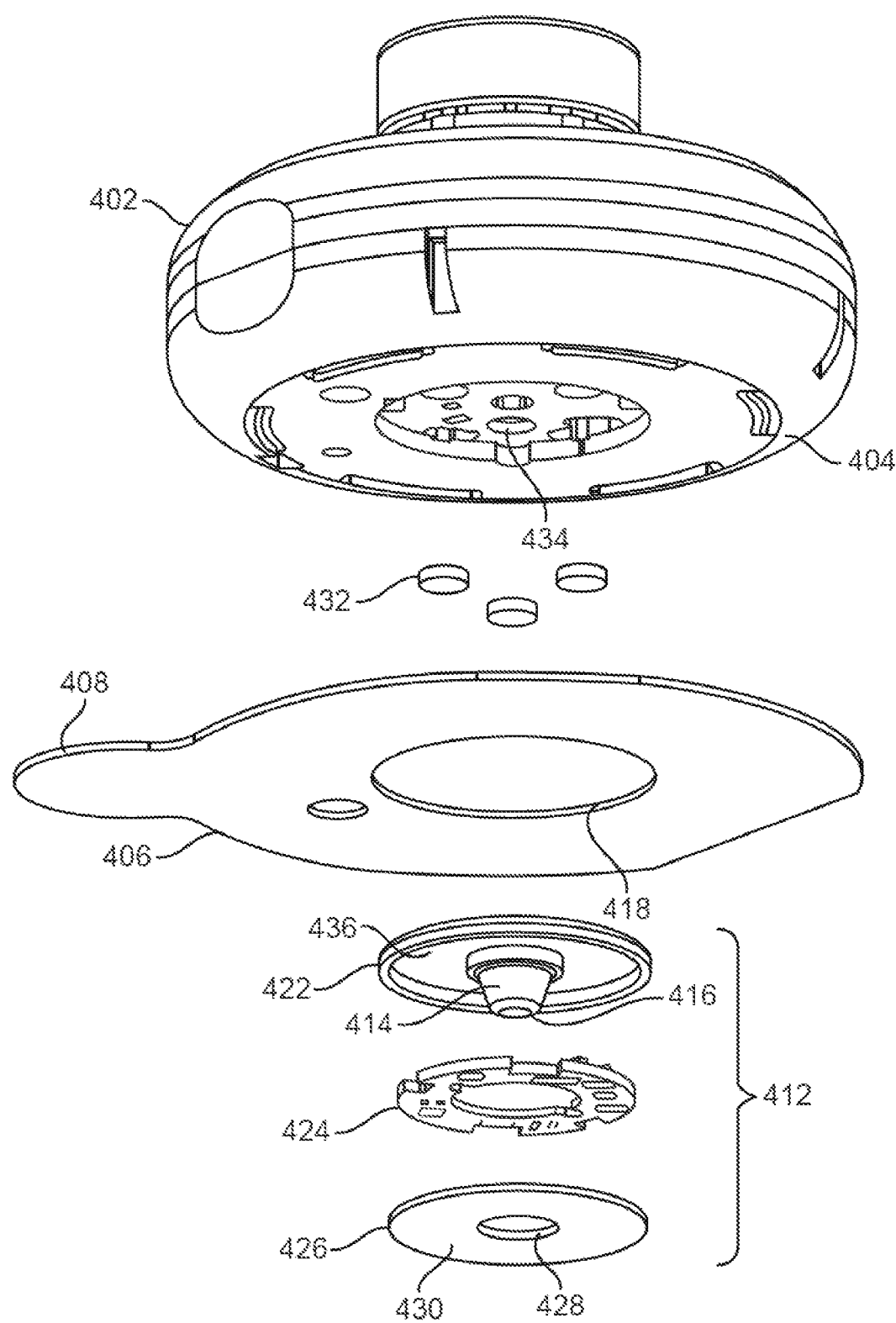
FIG. 60 shows an exploded view of the injector and patch of FIG. 59.

In one embodiment, illustrated in FIGS. 59 and 60, an injector of the type described above is indicated in general at 402. The device includes a housing including a circular base 404. A ring-shaped skin attachment layer 406 is secured to the base of the injector with an adhesive and features a pull tab 408. The underside of the attachment layer (visible in FIGS. 59 and 60) is provided with an adhesive that provides a lower holding force than the adhesive securing the attachment layer 406 to the injector. As a result, the injector 404 may be removed from the body (e.g., skin) of a subject by pulling up on tab 408 away from the skin of a subject.

In addition to the skin attachment layer 406, a patch, indicated in general at 412 in FIG. 59, and as in an exploded view of FIG. 60, is attached to the bottom of the injector by a magnetic fastening arrangement as will be explained in greater detail below. As an alternative to the magnetic attachment, the patch could be attached to the injector with adhesive or by other mechanical means.

While the patch and the skin attachment layer are illustrated as having circular profiles, alternative shapes may be used.

A generally conical skin boundary displacement extension 414 extends from the bottom of the patch 412 and, as described previously, compresses the skin to help reduce tissue deflection or "tenting" upon cannula insertion. The extension 414 features a central orifice 416 that aligns with the dispense port of the injector.

In an alternative embodiment, as described in embodiments presented above, the skin boundary displacement extension may be part of, and extend from, the base 404 of the injector itself. In such an embodiment, a central hole may be provided in the center of the patch, with the hole being smaller than the diameter of the base of the extension. When the injector is positioned with the skin attachment layer securing the device against the skin, the extension expands the hole in the patch, and provides a path for the injector cannula or cannula to enter the skin when the device is activated or "fired" in the manner described above. The cannula may not pass directly through the material and provide for the opportunity to clog the cannula or inject foreign bandage material into the skin from the cannula, see FIG. 16B. The expanded central hole of the patch closes to its original smaller size when the injector is removed from the skin. An absorbent material may be optionally deposited around the central hole of the patch to soak up any blood or leakage. In this way, the patch acts as a 'band aid' after the injection.

As in FIGS. 59 and 60, the skin attachment layer 406 features a central opening 418 that is sized to receive the patch 412. While the embodiment of FIGS. 59 and 60 illustrates the patch 412 as being separate from the skin attachment layer 406, in alternative embodiments, the patch may be circumferentially joined to the skin attachment layer by a perforation arrangement. As yet another alternative, the patch 412 may be fastened to the skin attachment layer via tabs circumferentially spaced about the patch.

As illustrated in FIG. 60, the patch 412 includes a sensor 422, a printed circuit board (PCB) chip 424 and a sensor adhesive layer 426. The PCB chip 424 and the sensor adhesive layer 426 are secured to the sensor 422 by adhesive or other fastening mechanisms. The sensor adhesive layer 426 includes a central window 428 through which, after assembly, the extension 414 protrudes, as illustrated in FIG. 59. The downward facing surface 430 of the sensor adhesive layer 426 is provided with an adhesive for securing the patch to the skin of a user.

The injector 402 and the patch 412 are configured so that the patch is applied to the body (e.g., skin, digits) of a subject (e.g., user) as the injector is attached. Furthermore, the patch 212 remains after the injector 402 is removed. More specifically, as illustrated in FIG. 60, a number of permanent magnets 432 are positioned and secured within the housing of the injector 402. As examples only, the magnets may be secured within corresponding recesses 434 formed within the injector housing by adhesive, interference fit or other attachment arrangements, as described elsewhere herein. The top side of the sensor 422 features a metallic disk portion 436 (FIGS. 59 and 60) so that the patch is secured to the bottom of the injector via magnetic attraction. The adhesive on surface 430 of the sensor adhesive layer 426 provides a holding force with the user's skin that is greater than the magnetic force holding the patch to the injector. As an alternative to disk portion 436 being metallic, the disk portion may be provided with metallic portions, illustrated in phantom at 437 of FIG. 59, that correspond to and attract the magnets of the injector. In an alternative embodiment, the metallic portion(s) of the patch may be provided with other shapes. A single ring-shaped metallic portion could also be used.

The use of magnets to secure the patch to the injector offers the advantage of no exposed residual adhesive on the patch as it remains on the patient. In addition, the magnets may be located precisely on the injector, and corresponding metallic portions located on the patch, so that we'll be able to control the amount and where the force is that is 'pulling' on the patch when the injector is removed. As an alternative to metallic portions on the injector, magnets may be used. In an alternative embodiment, the magnets may be located on the patch and the corresponding metallic portions may be located on the injector.

In an alternative embodiment, the patch 412 may be secured to the bottom of the injector by an adhesive (such as on the top side of sensor 422) that has less holding force than the skin-engaging adhesive on surface 430 of the sensor adhesive layer 426.

In another alternative embodiment, the patch 412 may be secured to the bottom of the injector using mechanical features built into either the patch, the injector or both with less holding force than the skin-engaging adhesive on surface 430 of the sensor adhesive layer 426. In such an embodiment, the skin attachment layer 406 of FIGS. 59 and 60 may be eliminated so that the injector is held to the patient only via the connection between the injector housing and the patch. In such an embodiment, both the injector and the patch are secured to the patient solely by the sensor adhesive layer. Additional connections between the housing of the injector and the sensor adhesive layer 426 could also exist (in addition to the connection of the injector to the sensor adhesive layer through the patch, as described elsewhere herein).

Figure 61:
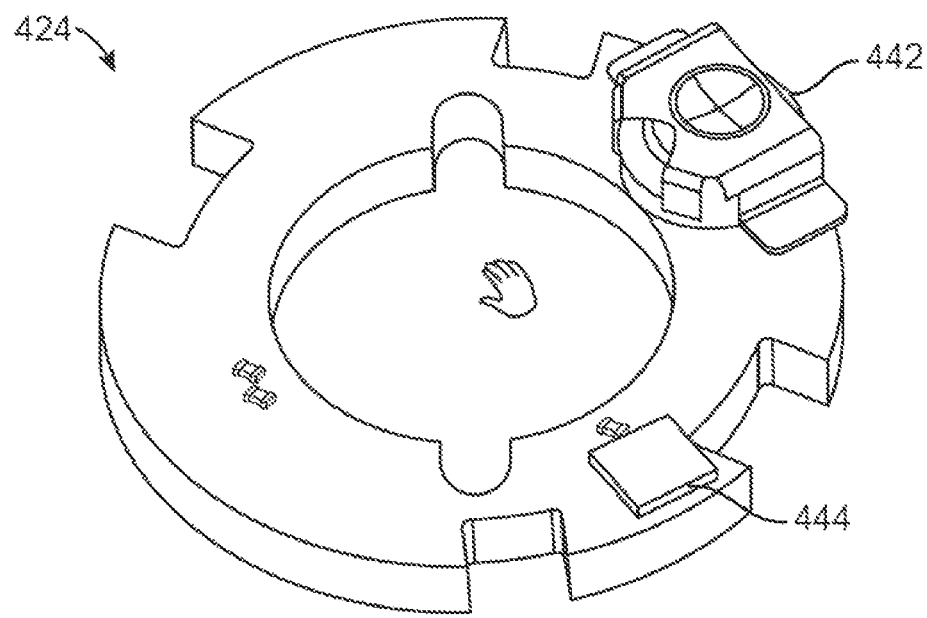
FIG. 61 shows a top side perspective view of the printed circuit board (PCB) chip of the patch of FIG. 60.
Figure 62:
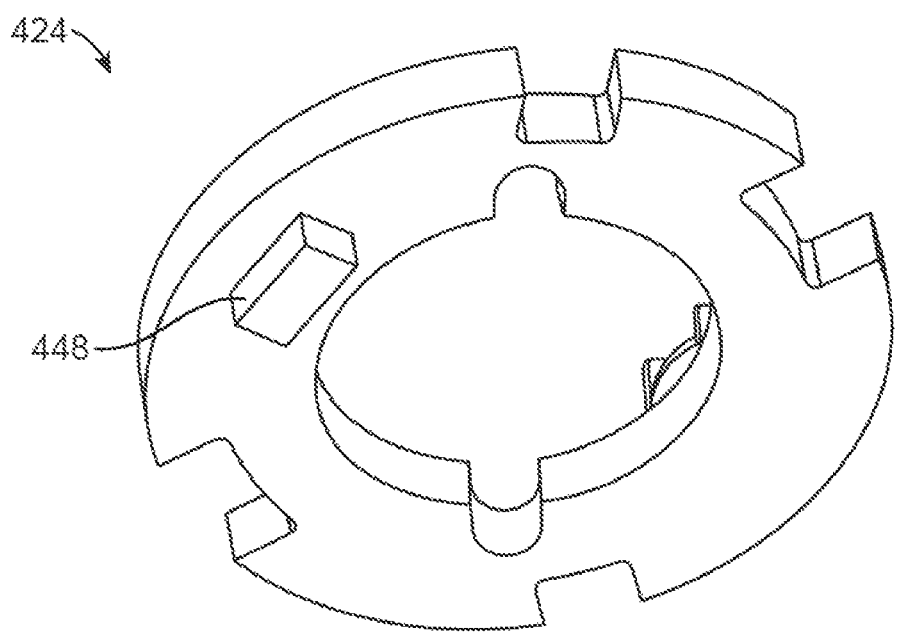
FIG. 62 shows a bottom side perspective view of the PCB chip of the patch of FIG. 60.

As illustrated in FIGS. 61 and 62, the PCB chip 424 features circuitry including a Bluetooth module with microcontroller/microprocessor 444 that is connected to a battery 442 and antenna 448. In addition, the Bluetooth module 444 is attached to sensor 422. The battery 442 provides for the stored energy to power the system. The Bluetooth module 444 has an integrated microcontroller/microprocessor. An example of a suitable Bluetooth module is Dialog Semiconductor Part number DA14580-01UNA. In alternative embodiments, the Bluetooth module may be separate from the microcontroller/microprocessor. In some embodiments, direct communication to the cloud may be used, such as, e.g., via cellular or other communication technologies.

Figure 63:
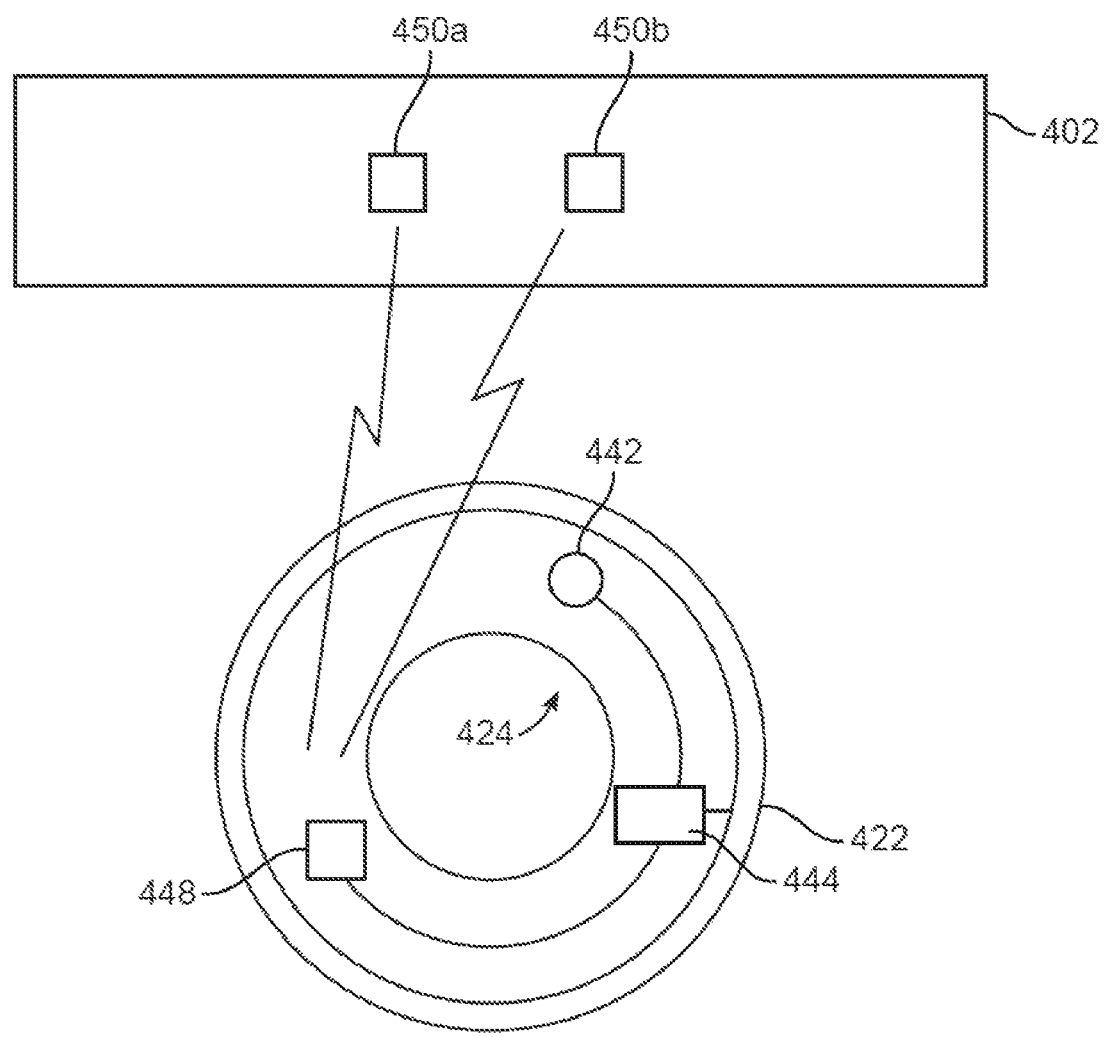
FIG. 63 shows a schematic of the injector and patch of FIGS. 59-63.

As illustrated in FIG. 63, the injector 402 is provided with one or more sensors 450a and 450b that communicate with the Bluetooth module 444 via Bluetooth. The sensors 450a and 450b may include transmitters and may receive power from a battery also positioned within the injector housing. Alternatively, each sensor may have its own battery. Sensors 450a and 450b may also be passive sensors that do not require battery power. The sensors 450a and 450b may be chosen to provide a variety of alternative functions as explained in greater detail below.

In alternative embodiments, communication between the sensors 450a and 450b of the injector and the module 444 of the PCB chip 424 of the patch may be accomplished by alternative wireless communication arrangements know in the art. In further alternative embodiments, the sensors 450a and 450b may communicate with the module 444 of the PCB chip 424 via wire connection(s) that automatically disconnect when the injector is removed from the patch and patient.

Of course the number of sensors 436, 450a and 450b may be varied from what is illustrated in FIGS. 61-63.

The Bluetooth module 444 also enables the patch to transmit data collected from sensors 422, 450a and 450b to a remote receiver such as a personal data device (such as a smart phone), a computer system or network or the cloud. The remote receiver may collect the received data within, and build, a database.

In use, initially the injector features the patch attached (via the magnetic arrangement described above), as illustrated in FIG. 59. A protective backing sheet is removed from the skin attachment layer 406 so that the adhesive on the surface facing away from the injector is exposed. This backing sheet also removably covers the adhesive on surface 430 of the patch. The exposed adhesive surfaces of the injector skin attachment layer 406 and the sensor adhesive layer 426 are then pressed against the skin of a user so that the injector and the patch are attached thereto.

In the illustrated embodiment, the patch 412 has multiple functions. First it senses and transmits the state of the injector to a remote receiver (such as a personal data device, for example, a smart phone, a computer network or the cloud), i.e. has the injector been activated so that the injection is being given or has the injection been completed. The second thing is the patch transmits the state of the patient via data collected from the sensors to the remote receiver. This can be done before, during or after the injection and before, during or after attachment and or removal of the injector. For example, the temperature of the skin at the injection site and the skin 'color' may be detected via a simple temperature monitor combined with an LED/phototransistor circuit included in the sensor 422 for transmitting the tissue temperature and color during and after the injection. This feature can be useful during a clinical study, to alert the staff if there is an injection site reaction (ISR), and it could quantify the ISR based on temperature and tissue color. The third thing is the patch could interact directly injector based on data received from the injector and/or data received from the patient and/or data received from itself. The patch could interact with the injector as a control mechanism including adjustment of the flowrate (faster, slower or pause), vibrate for user notification and/or pain management, provide an audible sound to provide direction or notification to the user, visual indicators to indicate change, alerts, notifications or information to the user, or mechanical interactions to cause a change in state of the injector including but not limited to retraction of the button to stop the delivery in the instance of data from the patient (for example, pain) or data from the device (for example, premature removal or fall-off).

A heartrate sensor could also be included in sensors 422 to obtain a patient EKG signal if useful and/or a strain gage sensor may be provided to detect the skin pressure exerted by the extension 414 FIGS. 59 and 60. Patient mobility, position and location data may be collected by corresponding sensors (such as an accelerometer, GPS sensor or the like) incorporated in sensor 422. In addition, a couple of electrodes (included in sensor 422) in contact with the skin could detect skin impedance and detect leakage or detachment. Furthermore, the skin contact electrodes could detect a premature removal of the device, i.e. removal of the device before the device has completed its cycle.

Upon completion of an injection by the injector, the injector can be removed from the patient's skin by pulling tab 408 (FIGS. 59 and 60) away from the patient's skin. As this is done, the patch is decoupled from the injector allowing only the patch to be adhered to the patient. The detachable nature of the monitoring patch provides a physician or the like with the ability to monitor the patient continuously between injections.

Alternatively, the patch could be initially decoupled from the injector and placed on the patient to monitor before start of administration/injection of a drug or drugs. This could provide baseline data about the patient prior to the administration/injection.

Alternatively, the patch could be applied independently of the injector and placed on the patient to monitor baseline conditions (e.g., a baseline physiologic parameter) before the start of the administration/injection of drug or drugs. The injector could then be coupled to the patch prior to start of the injection.

Figure 64:
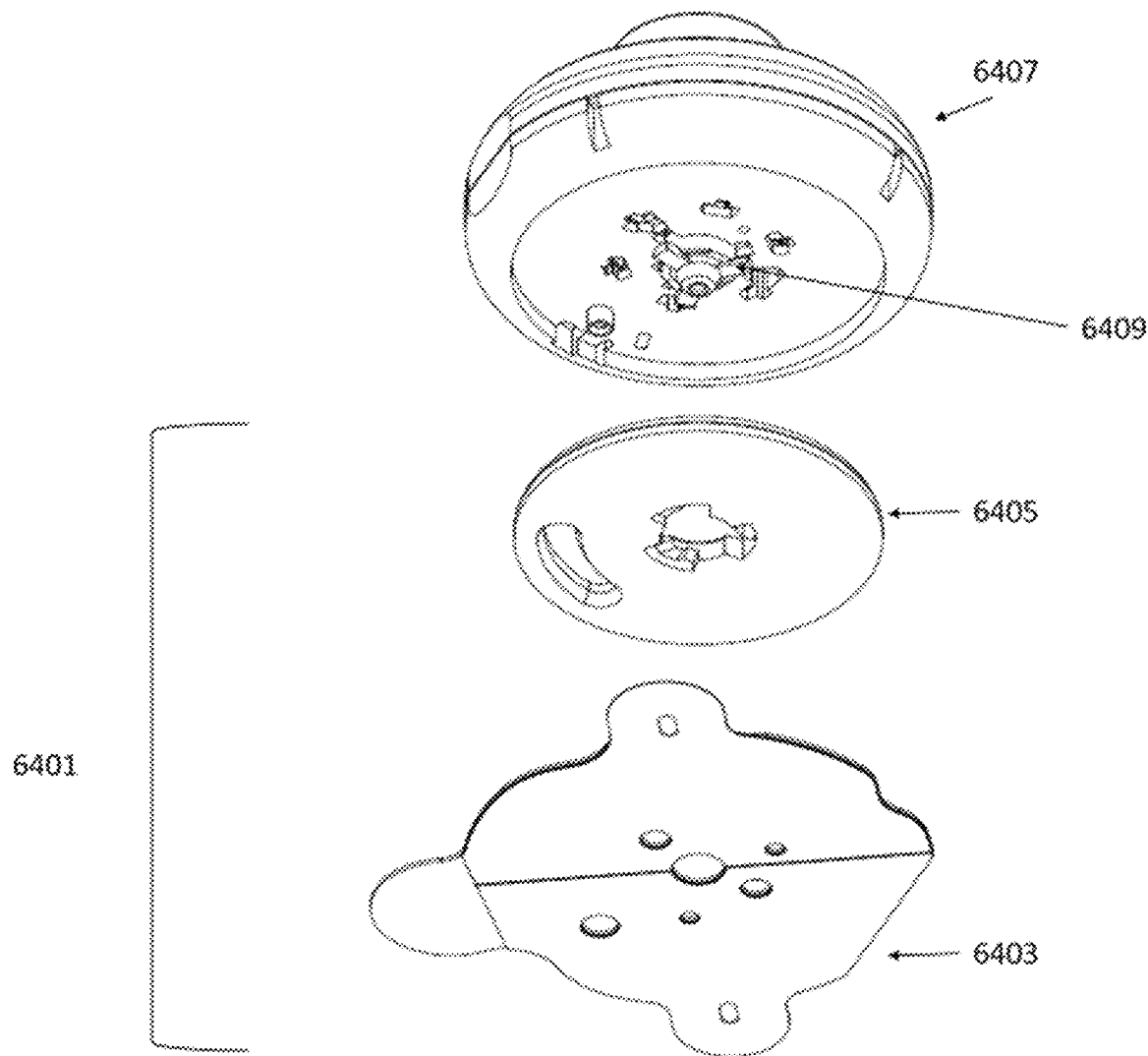
FIG. 64 shows a schematic of another example of an injector coupled to a patch.
Figure 65:
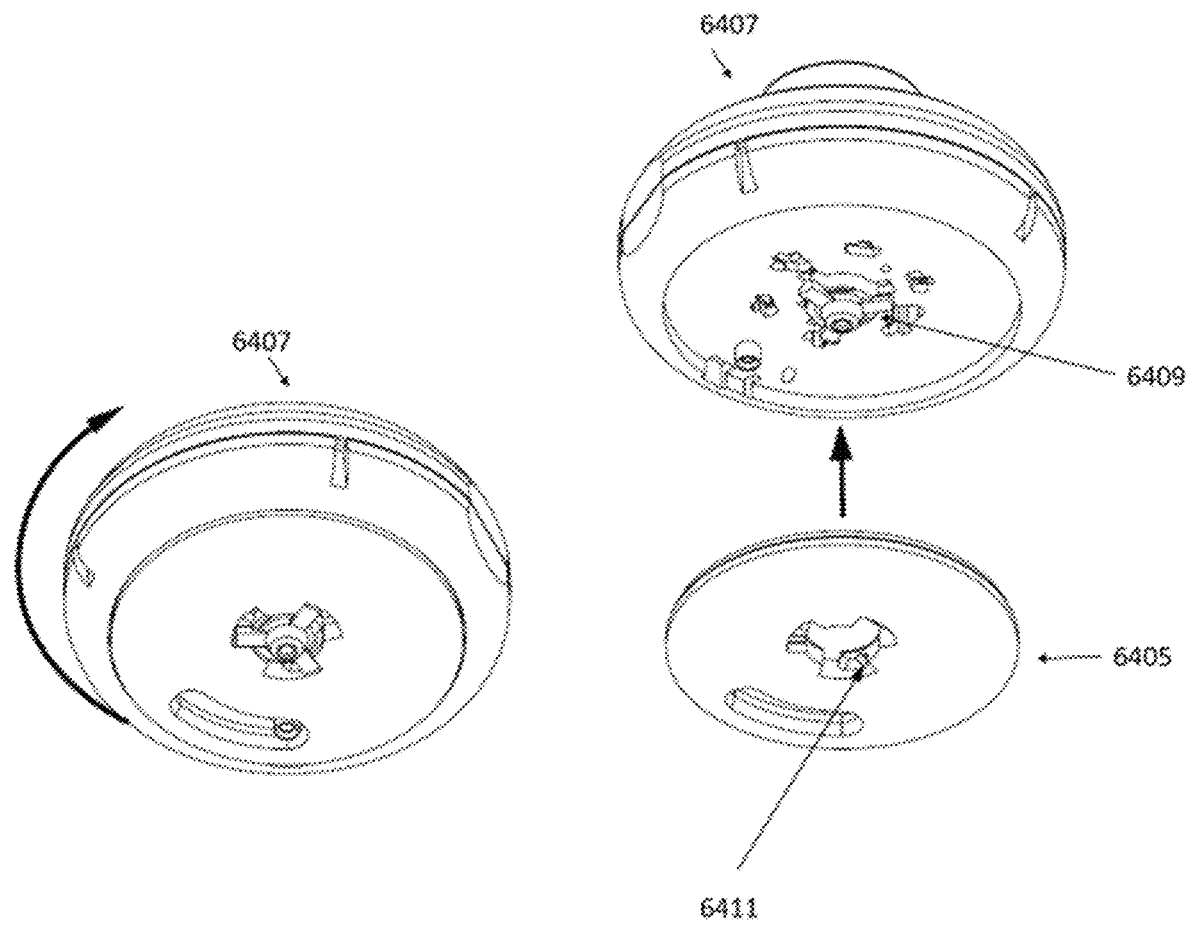
FIG. 65 shows another view of the patch and injector shown in FIG. 64.

FIGS. 64-65 illustrate exploded views of another embodiment of the patch and injector. The patch 6401 includes an adhesive layer 6403 and a sensor 6405, which may comprise the PCB chip. In this embodiment, and in further embodiments described below, the patch and/or injector may each include one or more sensors, as described in the previous embodiments. The sensor 6405 may adhere to the adhesive layer 6403, which may be used to secure the patch 6401 to the body of the subject. The injector 6407 and the patch 6401 can be configured so that the patch is applied to the body of the subject as the injector 6407 is attached. Alternatively, or in addition to, the injector 6407 and the patch 6401 may be coupled prior to securing the patch 6401 and injector 6407 to the body of the subject.

The patch 6401 may be coupled to the injector 6407 using an interlocking bayonet mechanism. For instance, the injector 6407 can comprise protruding elements 6409, which can interface with detents 6411 in the patch 6401. The detents 6411 may prevent free rotation of the patch 6401 and the protruding elements 6409 in a first configuration. Upon twisting of the patch 6401 or the injector 6407, the injector 6407 may be moved to a second configuration, in which the protrusions 6409 no longer couple to the detents 6411, and thus the injector 6407 can be decoupled or removed from the patch 6401 (e.g., after the patch is secured to the body of the subject and the medicament has been delivered).

Figure 66:
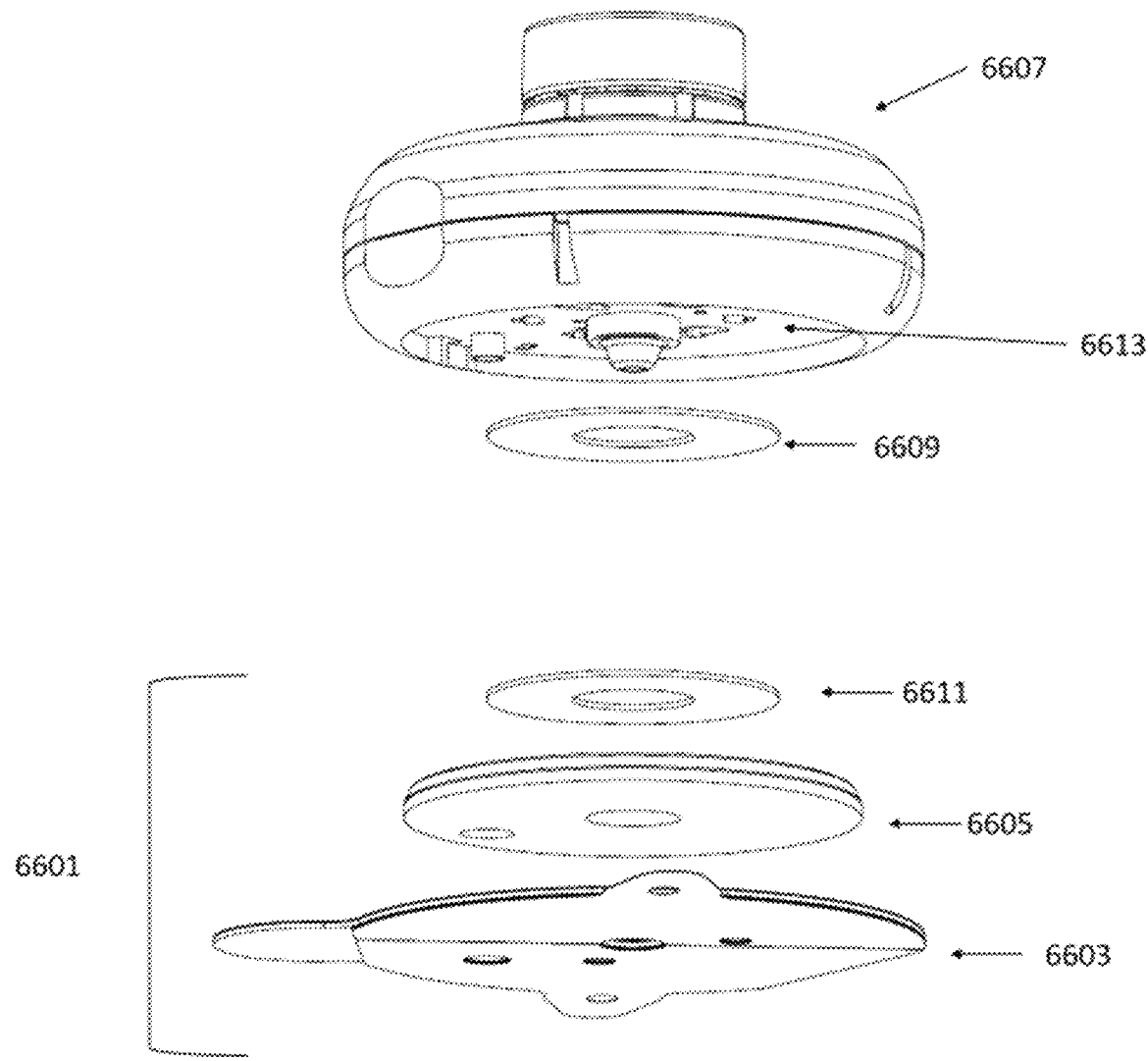
FIG. 66 shows a schematic of another example of an injector coupled to a patch.

FIG. 66 illustrates an exploded view of another embodiment of the patch and injector. The patch 6601 includes an adhesive layer 6603 and a sensor 6605, which may comprise the PCB chip. The sensor 6605 may adhere to the adhesive layer 6603, which may be used to secure the patch 6601 to the body of the subject. The injector 6607 and the patch 6601 can be configured so that the patch is applied to the body of the subject as the injector 6607 is attached. Alternatively, or in addition to, the injector 6607 and the patch 6601 may be coupled prior to securing the patch 6601 and injector 6607 to the body of the subject.

The patch 6601 may be coupled to the injector 6607 by coupling or mating parts 6609 and 6611. Part 6609 may be coupled to the injector 6607 (e.g., in a recess 6613) whereas part 6611 may be coupled to the patch 6601. Parts 6609 and 6611 may be magnets and may be secured to the recess 6613 of the injector 6607 and the patch 6601, respectively, via adhesive, interference fit, or other attachment arrangements. The adhesive layer 6603 can provide a holding force with the subject's body (e.g., skin) that is greater than the magnetic force holding the patch to the injector.

Figure 67:
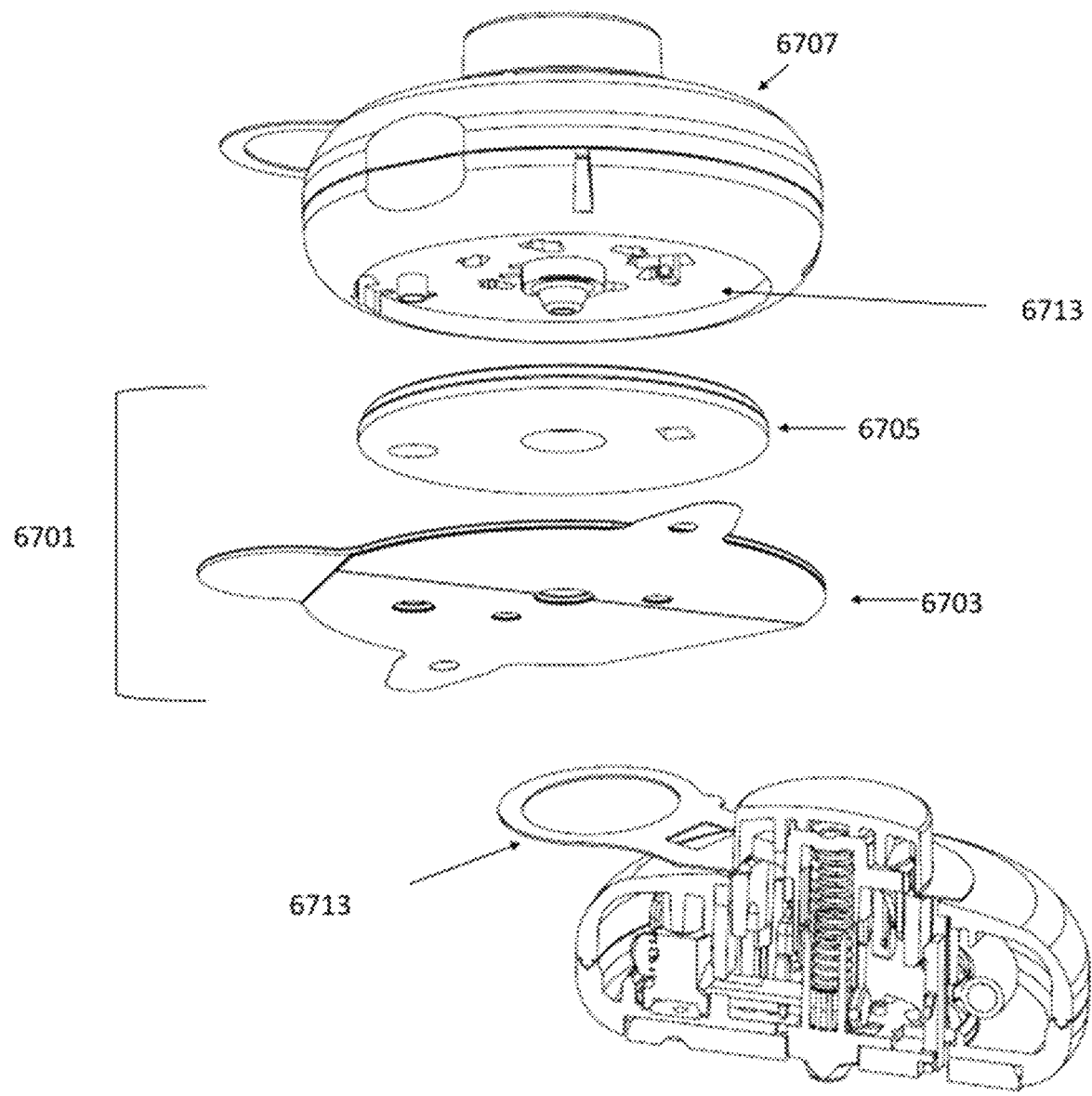
FIG. 67 shows a schematic of another example of an injector coupled to a patch.

FIG. 67 illustrates another embodiment of the patch and injector. The patch 6701 includes an adhesive layer 6703 and a sensor 6705, which may comprise the PCB chip. The sensor 6705 may adhere to the adhesive layer 6703, which may be used to secure the patch 6701 to the body of the subject. The injector 6707 and the patch 6701 can be configured so that the patch is applied to the body of the subject as the injector 6707 is attached. Alternatively, or in addition to, the injector 6707 and the patch 6701 may be coupled prior to securing the patch 6701 and injector 6707 to the body of the subject.

The patch 6701 may be coupled to the injector 6707. For instance, the sensor 6705 may be configured to couple to the injector 6707 by fitting into a recess 6713. The injector can comprise a safety tab or strip. The adhesive layer 6703 can provide a holding force with the subject's body (e.g., skin) that is greater than the magnetic force holding the patch to the injector.

Figure 68:
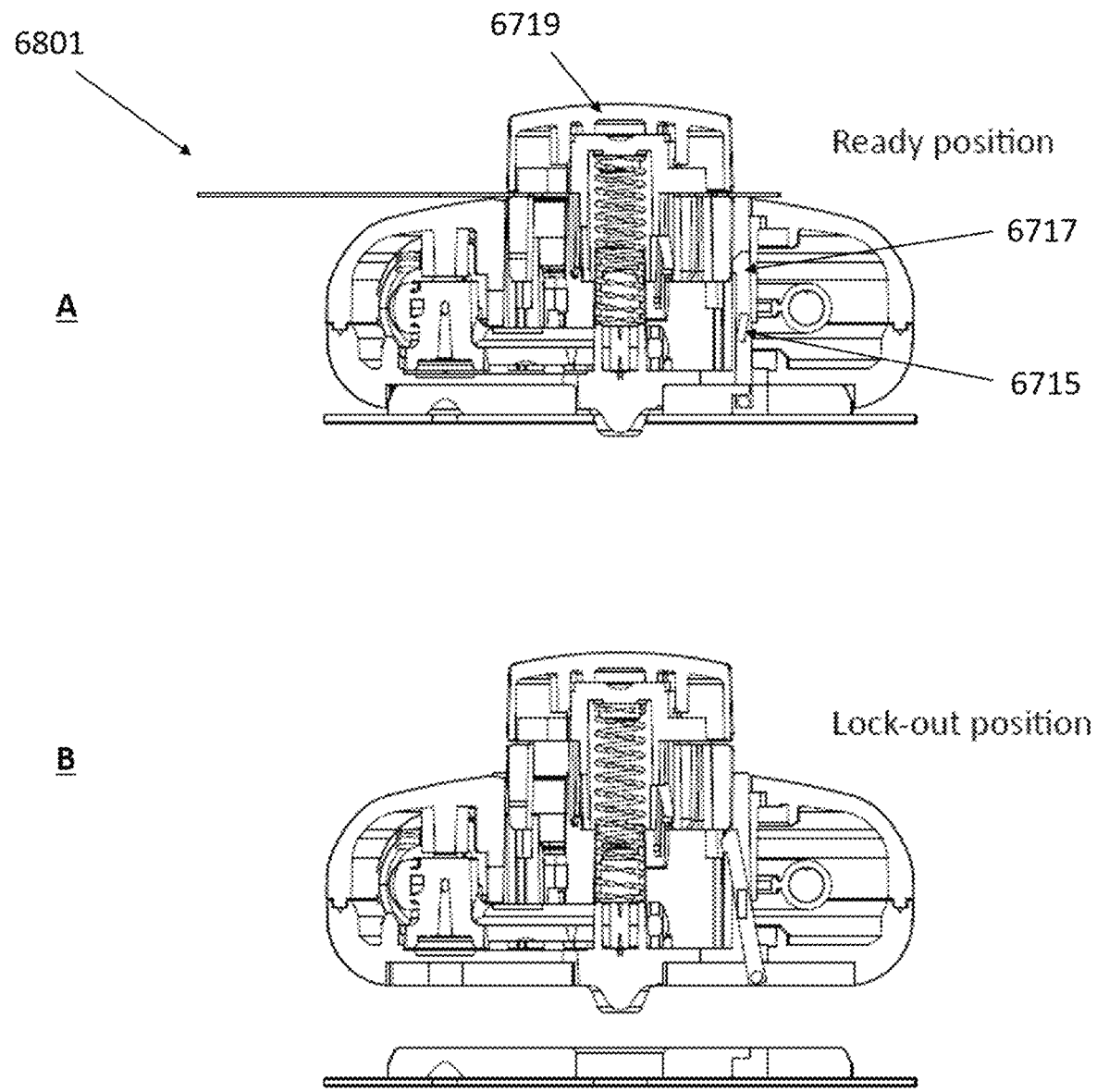
FIG. 68 shows a cross-sectional view of the patch and injector of FIG. 67.

FIG. 68 shows a cross-sectional view of the coupled injector and patch of FIG. 67. The injector can comprise a latch 6717 connected to a spring (e.g., torsion spring) 6715. In Panel A, the patch and injector may be in a first configuration ("Ready position"), where the device is locked, and the patch remains attached to the injector. The button 6719, which can be used to direct the cannula toward the subject when depressed, is in a start or ready position and ready for actuation. In panel B, the injector may be transformed (e.g., via rotation, removal of the safety tab 6801, or both), into a second configuration ("Lock-out position"). In the second configuration, the torsion spring may be released, thereby translating the latch 6717 to a different position. In such a configuration, the injector is removable from the patch, and the button 6719 may be in the raised position illustrated in panel B, preventing depression of the cannula out of the injector.

Figure 69:
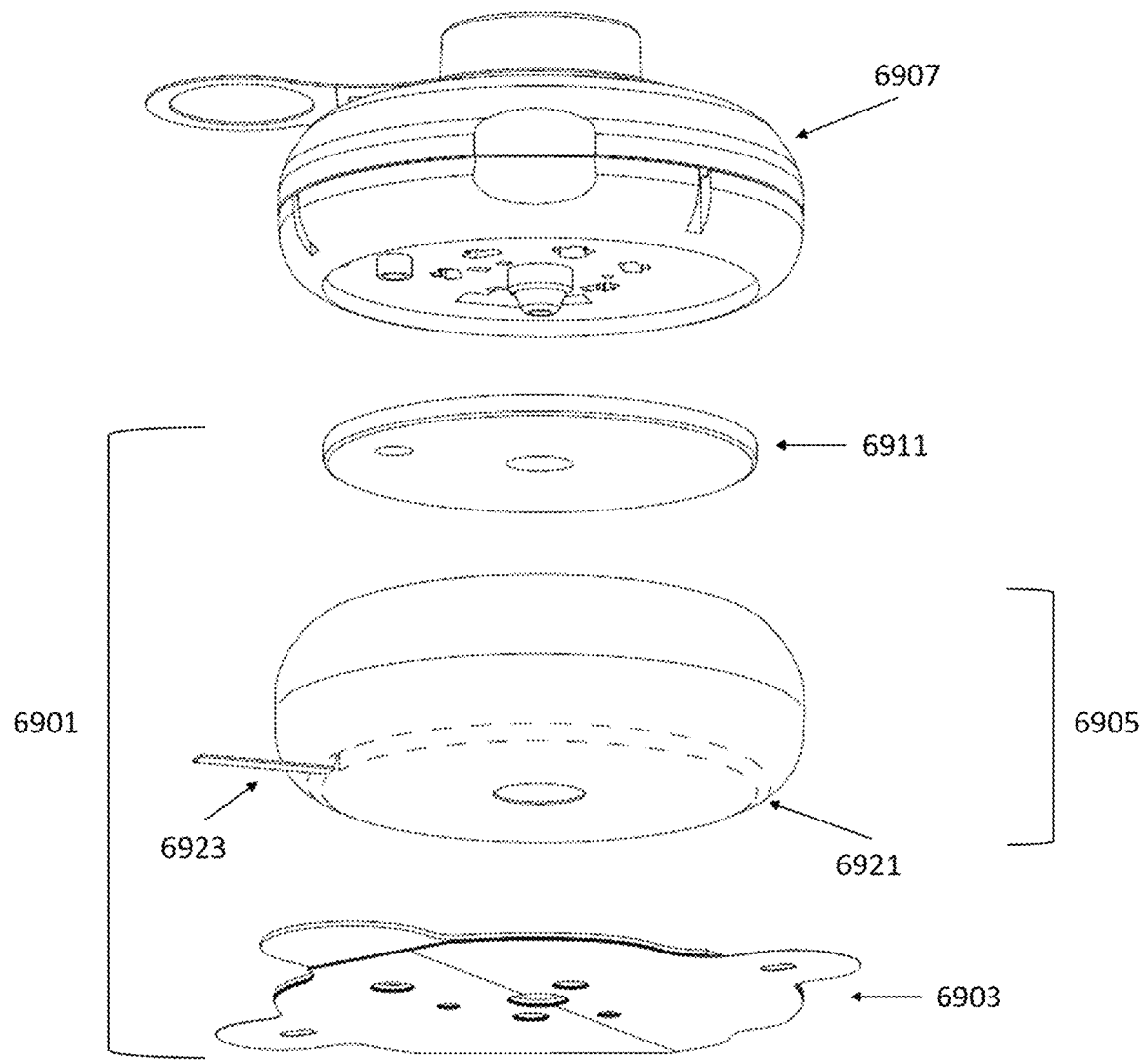
FIG. 69 shows a schematic of another example of an injector coupled to a patch.

FIG. 69 illustrates another embodiment of the patch and injector. The patch 6901 includes an adhesive layer 6903, a sensor 6905, which may comprise the PCB chip, and an attachment module 6911. The attachment module 6911 may comprise an adhesive or other fastening mechanism to adhere the patch 6901 to the injector 6907. The sensor 6905 may adhere to the adhesive layer 6903, which may be used to secure the patch 6901 to the body of the subject. The injector 6907 and the patch 6901 can be configured so that the patch is applied to the body of the subject as the injector 6907 is attached. Alternatively, or in addition to, the injector 6907 and the patch 6901 may be coupled prior to securing the patch 6901 and injector 6907 to the body of the subject. The patch 6901 may additionally comprise an external layer comprising perforations 6921. For instance, the external layer may comprise a plastic, polymer (e.g., thermosensitive polymer, e.g., shrink wrap), or other material. The external layer can be configured to be removed prior to use of the patch and injector. When the device is ready for use, the external layer may be removed by pulling on a pull tab 6923, which may remove the external layer via the perforations 6921, thereby allowing removal of the external layer.

Figure 70:
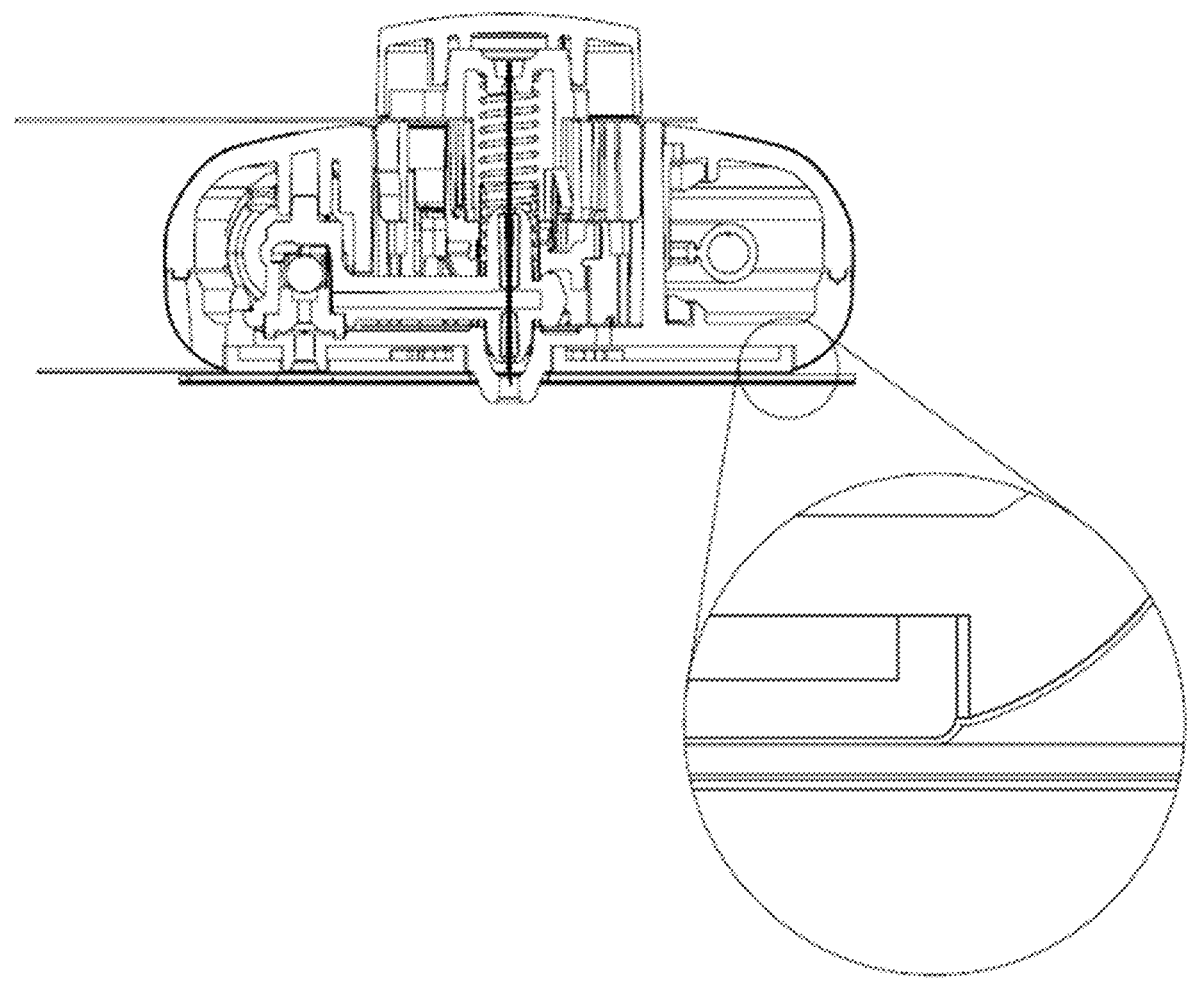
FIG. 70 shows a cross-sectional view of the patch and injector of FIG. 69.

FIG. 70 shows a cross-sectional view of the coupled injector and patch of FIG. 69. A dimension of the patch (e.g., the width or diameter) may be substantially similar as the diameter of the injector.

Figure 71:
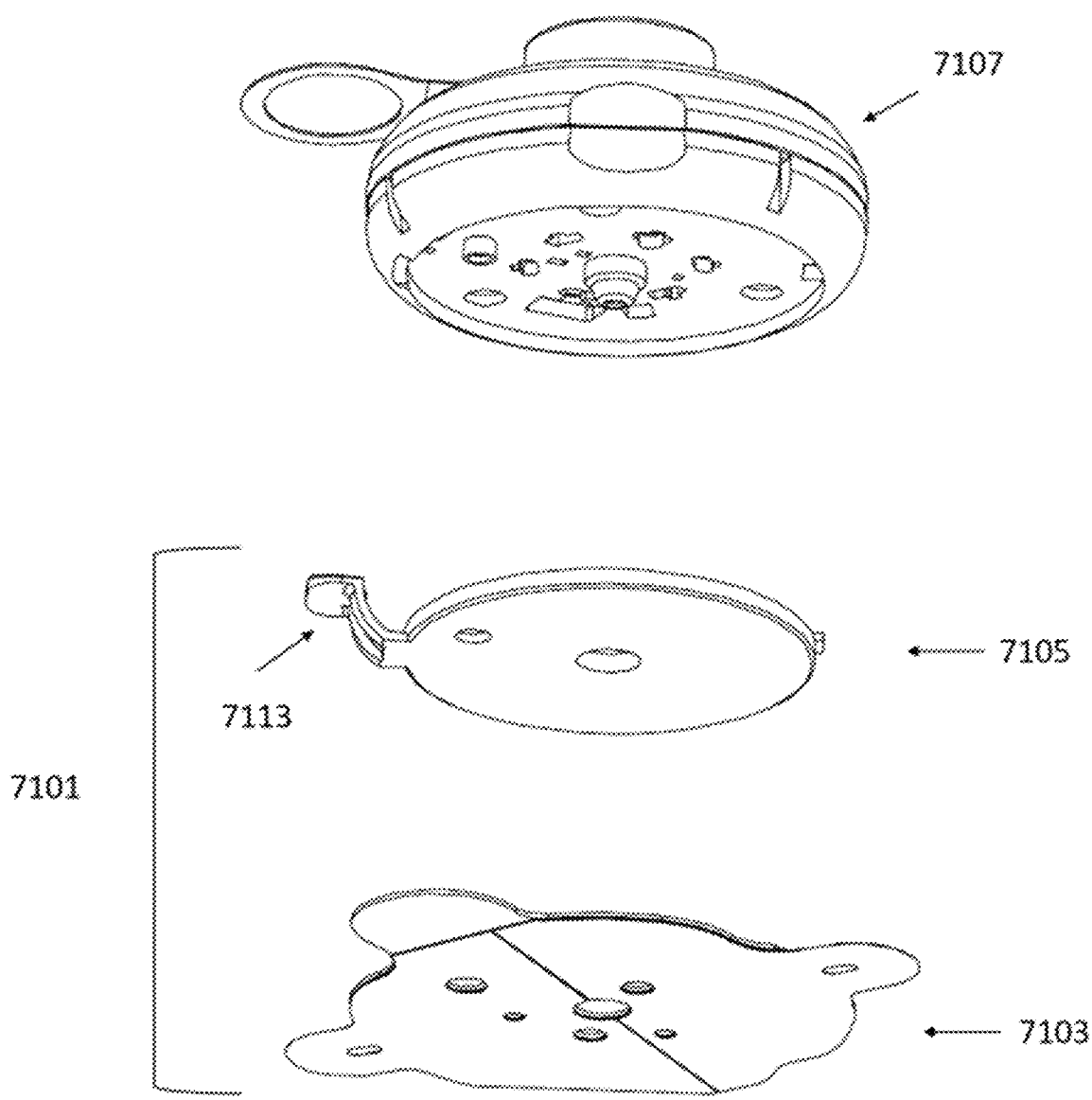
FIG. 71 shows a schematic of another example of an injector coupled to a patch.

FIG. 71 illustrates another embodiment of the patch and injector. The patch 7101 includes an adhesive layer 7103 and a sensor 7105, which may comprise the PCB chip. The sensor 7105 may adhere to the adhesive layer 7103, which may be used to secure the patch 7101 to the body of the subject. The injector 7107 and the patch 7101 can be configured so that the patch is applied to the body of the subject as the injector 7107 is attached. Alternatively, or in addition to, the injector 7107 and the patch 7101 may be coupled prior to securing the patch 7101 and injector 7107 to the body of the subject. The patch 7101 may be coupled to the injector 7107 via latch 7113. The latch 7113 may be coupled to the injector 7101 using a press-fit mechanism, and subsequent pushing or applying force to the latch 7113 can result in detachment of the patch 7101 from the injector 7107. Alternatively or in addition to, the latch 7113 may comprise a hook that can adhere to the housing of the injector 7107. The latch may then be actuated by pressing or applying a force on the latch 7113 and pulling the latch away from the housing of the injector 7107, which allows for detachment of the patch 7101 from the injector 7107.

Figure 72:
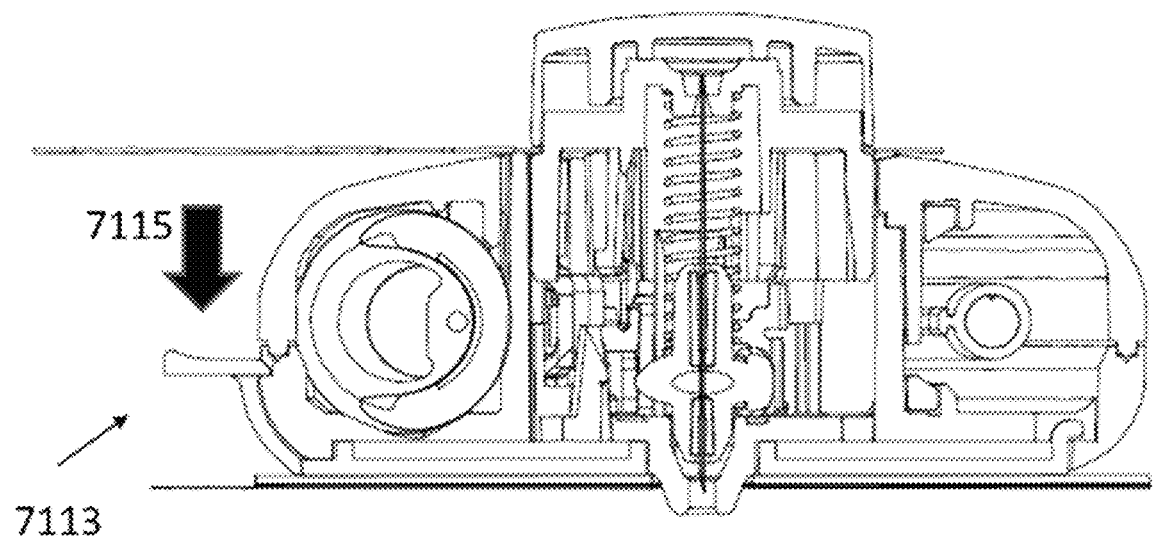
FIG. 72 shows a cross-sectional view of the patch and injector of FIG. 71.

FIG. 72 shows a cross-sectional view of the coupled injector and patch of FIG. 71. The latch 7113 comprises a hook to adhere to the housing of the injector. By applying a force 7115 on the latch, the hook can be released, thereby allowing decoupling or detachment of the patch from the injector.

Figure 73:
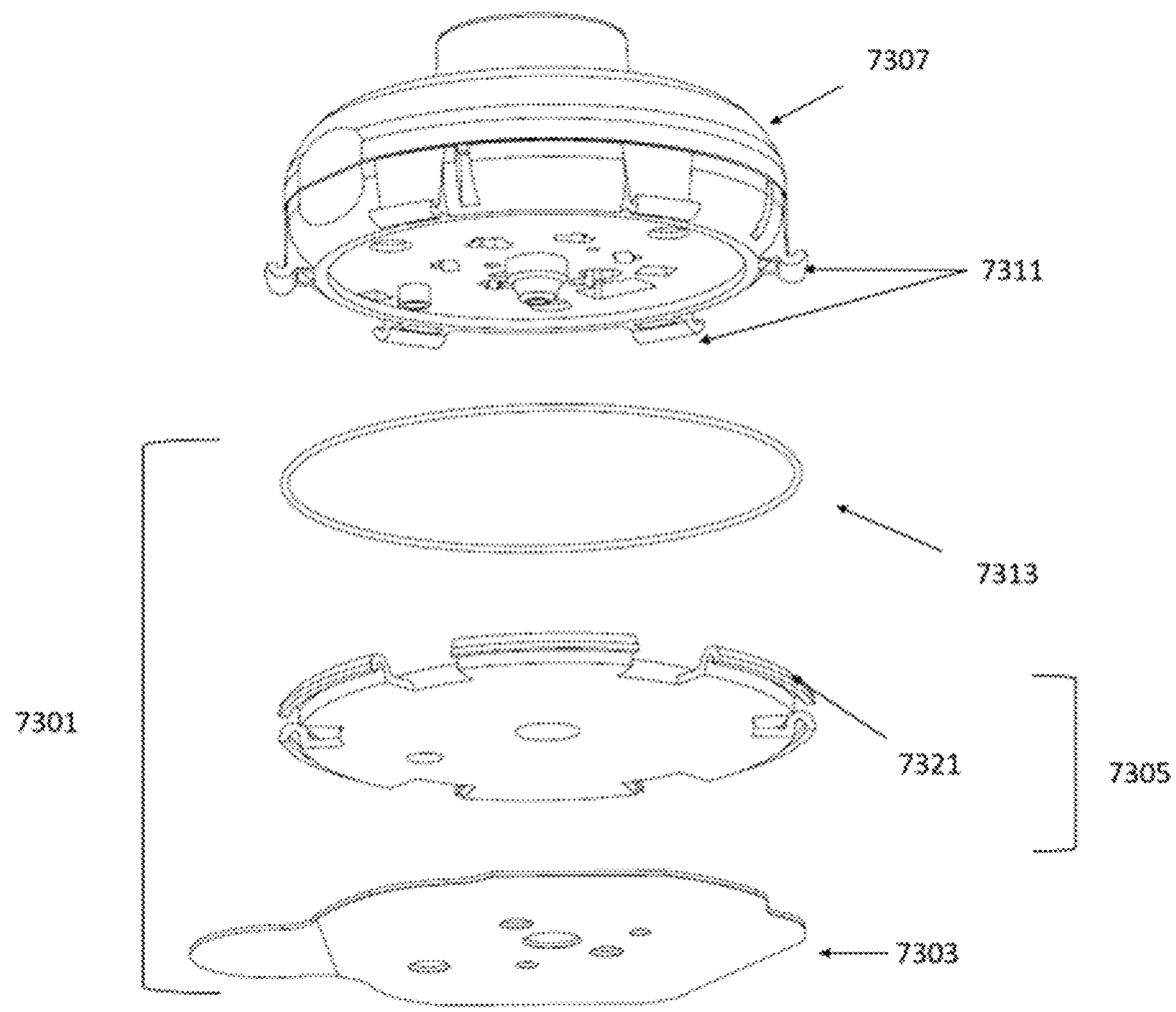
FIG. 73 shows a schematic of another example of an injector coupled to a patch.

FIG. 73 illustrates another embodiment of the patch and injector. The patch 7301 includes an adhesive layer 7303 and a sensor 7305, which may comprise the PCB chip. The sensor 7305 may adhere to the adhesive layer 7303, which may be used to secure the patch 7301 to the body of the subject. The injector 7307 and the patch 7301 can be configured so that the patch is applied to the body of the subject as the injector 7307 is attached. Alternatively, or in addition to, the injector 7307 and the patch 7301 may be coupled prior to securing the patch 7301 and injector 7307 to the body of the subject. The patch 7301 may be coupled to the injector 7307 via flanges 7311 and ring 7313. The ring 7313 may comprise a rubber or other elastomeric material. The ring 7313 can couple to the injector 7307 by fitting into the grooves of the flanges 7311 and 7321. The flanges 7311 may be complementary to the flanges 7321 of the patch 7301.

Figure 74:
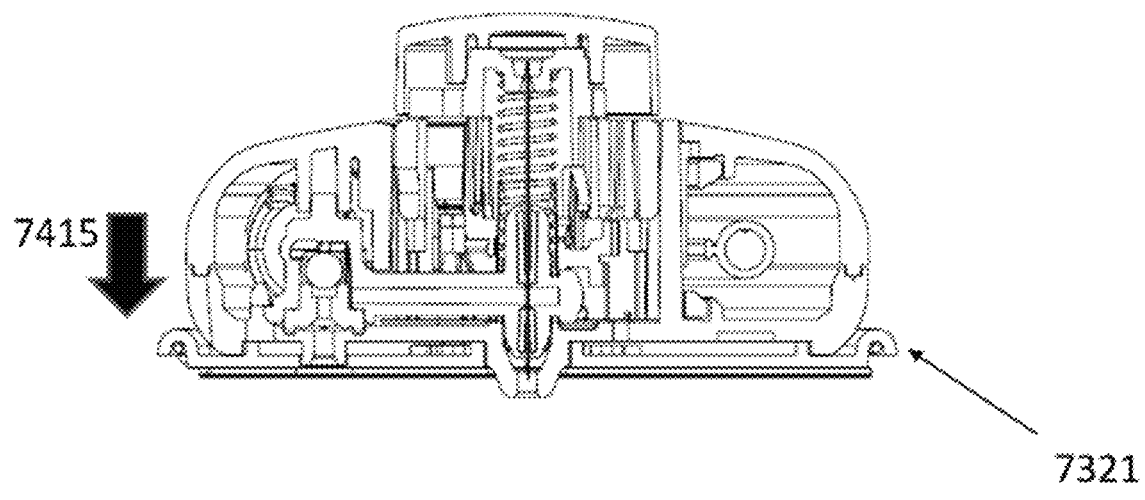
FIG. 74 shows a cross-sectional view of the patch and injector of FIG. 73.

FIG. 74 shows a cross-sectional view of the coupled injector and patch of FIG. 73. The flanges 7321 of the patch may fit complementarily to the flanges 7311 of the injector. By applying a force 7415 on the flanges 7321, the patch may be detached from the injector.

Figure 75:
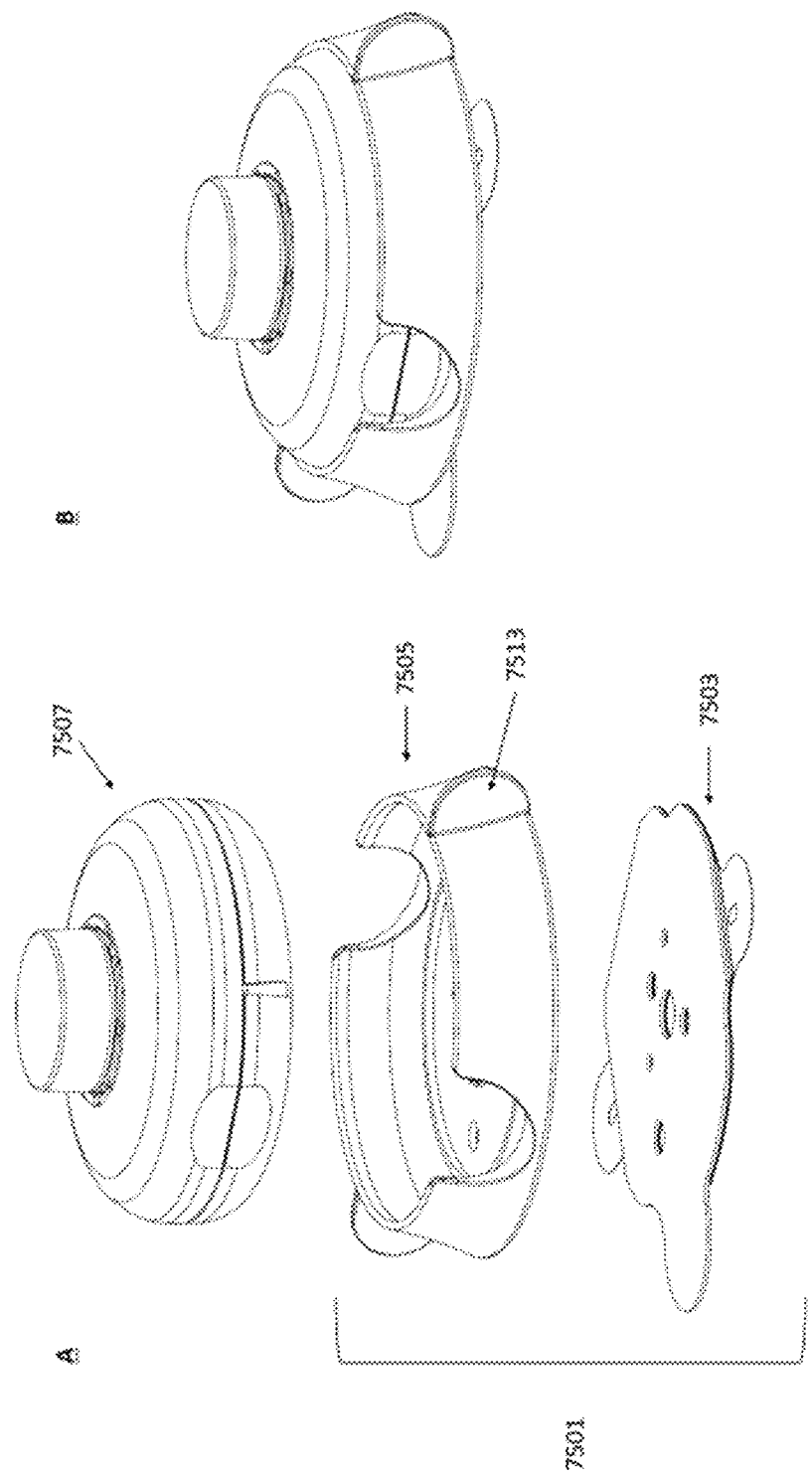
FIG. 75 shows a schematic of another example of an injector coupled to a patch.

FIG. 75 illustrates another embodiment of the patch and injector. As shown in Panel A, the patch 7501 includes an adhesive layer 7503 and a sensor 7505, which may comprise the PCB chip. The sensor 7505 may adhere to the adhesive layer 7503, which may be used to secure the patch 7501 to the body of the subject. The injector 7507 and the patch 7501 can be configured so that the patch is applied to the body of the subject as the injector 7507 is attached. Alternatively, or in addition to, the injector 7507 and the patch 7501 may be coupled prior to securing the patch 7501 and injector 7507 to the body of the subject, as shown in panel B. The housing of the patch 7501 and sensor 7505 may partially surround the housing of the injector 7507. The patch may also comprise winged features 7513. The features 7513 may allow for better grip of the subject, or for positioning the device.

Figure 76:
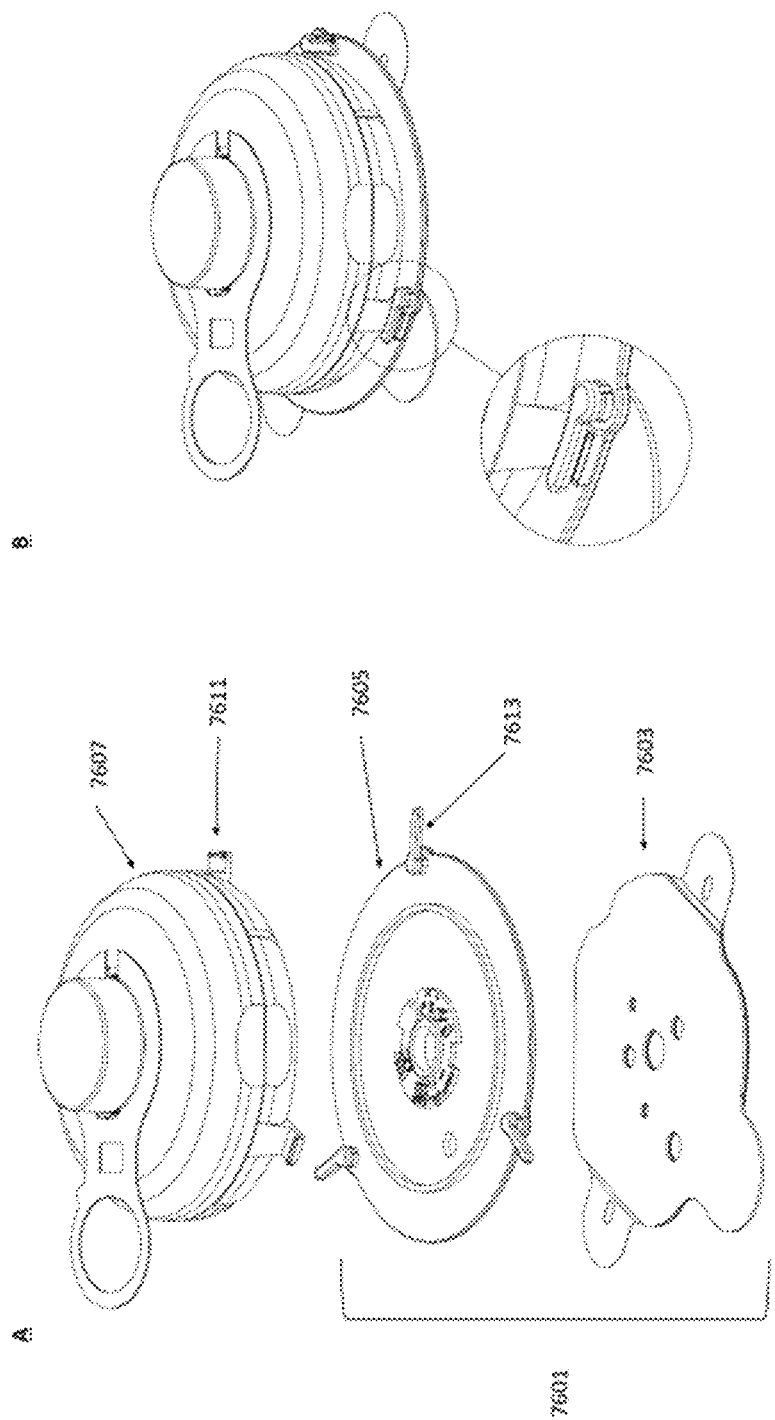
FIG. 76 shows a schematic of another example of an injector coupled to a patch.

FIG. 76 illustrates another embodiment of the patch and injector. In panel A, the patch 7601 includes an adhesive layer 7603 and a sensor 7605, which may comprise the PCB chip. The sensor 7605 may adhere to the adhesive layer 7603, which may be used to secure the patch 7601 to the body of the subject. The injector 7607 and the patch 7601 can be configured so that the patch is applied to the body of the subject as the injector 7607 is attached. Alternatively, or in addition to, the injector 7607 and the patch 7601 may be coupled prior to securing the patch 7601 and injector 7607 to the body of the subject, as shown in panel B. The patch 7601 may be coupled to the injector 7601 via a latch 7613, which may secure to a protrusion 7611 of the injector 7611. The latch may be rotatable, such that in certain configurations, the latch 7613 does not rest on the protrusion 7611, allowing decoupling of the patch 7601 from the injector 7607.

Figure 77:
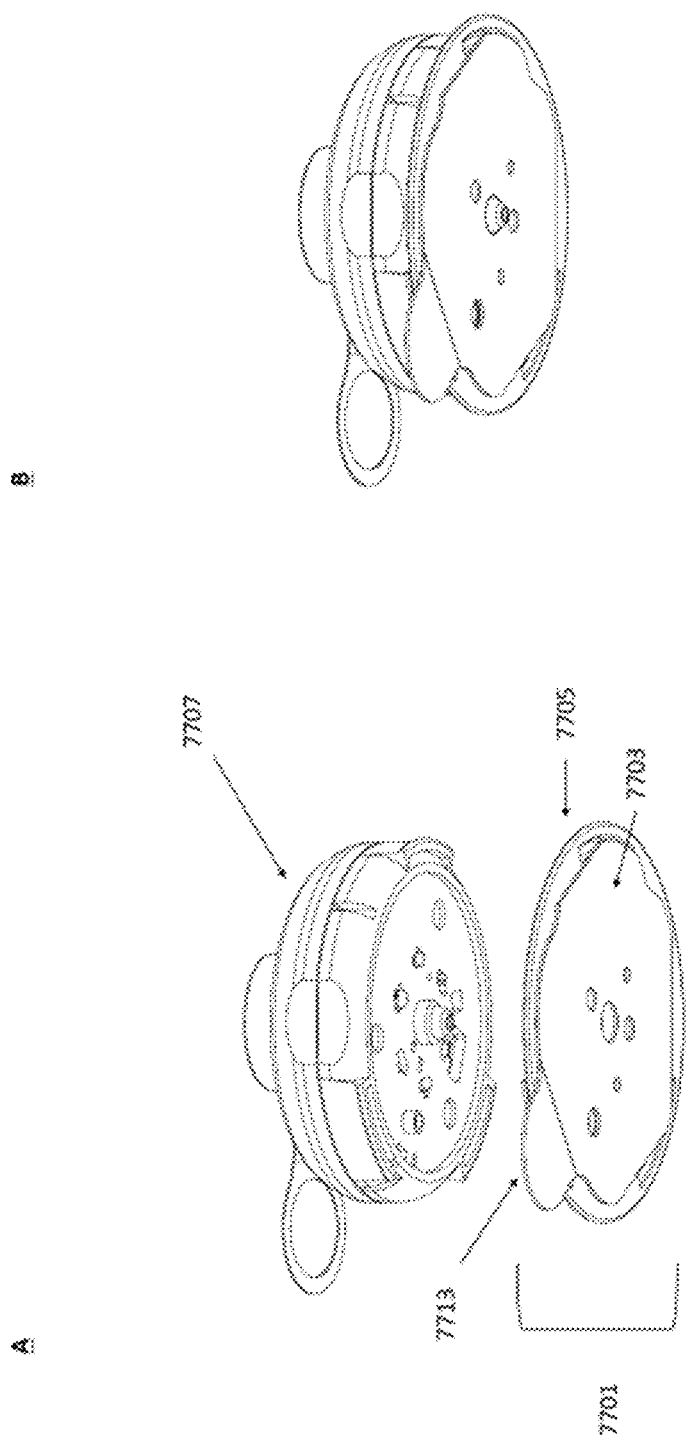
FIG. 77 shows a schematic of another example of an injector coupled to a patch.

FIG. 77 illustrates another embodiment of the patch and injector. In panel A, the patch 7701 includes an adhesive layer 7703 and a sensor 7705, which may comprise the PCB chip. The sensor 7705 may adhere to the adhesive layer 7703, which may be used to secure the patch 7701 to the body of the subject. The injector 7707 and the patch 7701 can be configured so that the patch is applied to the body of the subject as the injector 7707 is attached. Alternatively, or in addition to, the injector 7707 and the patch 7701 may be coupled prior to securing the patch 7701 and injector 7707 to the body of the subject, as shown in panel B. The patch 7701 may be coupled to the injector 7707 via an adhesive (e.g., at the interface between the patch 7701 and injector 7707). The patch may also comprise, e.g., on the adhesive layer 7703, a protruding feature 7713. The protruding feature may allow for decoupling of the patch 7701 from the injector 7707 when a subject presses or pulls on the feature 7713.

Figure 78:
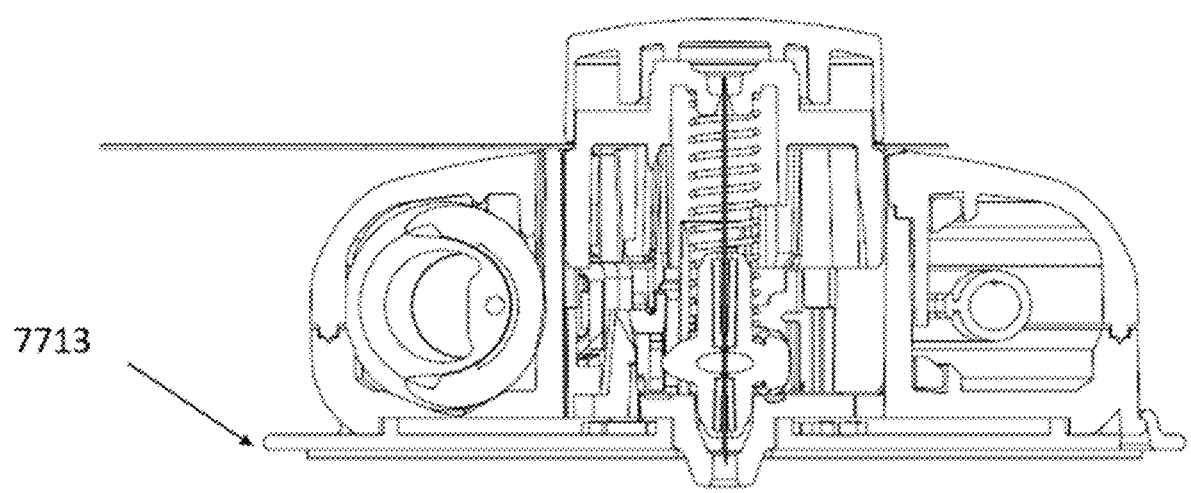
FIG. 78 shows a cross-sectional view of the patch and injector of FIG. 77.

FIG. 78 shows a cross-sectional view of the coupled injector and patch of FIG. 77. The protruding feature 7713 may be used to pry the patch from the injector.

Figure 79:
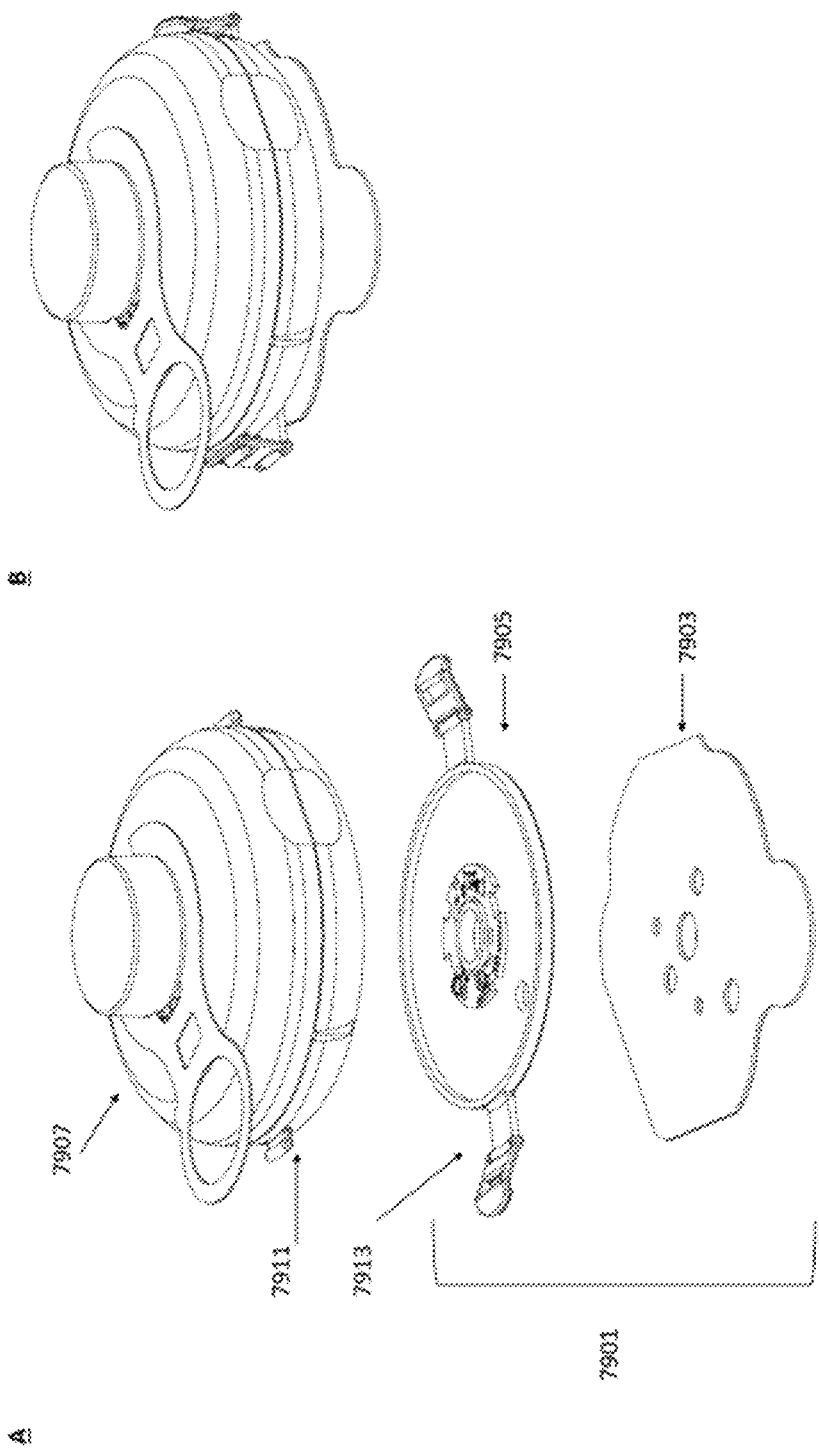
FIG. 79 shows a schematic of another example of an injector coupled to a patch.

FIG. 79 illustrates another embodiment of the patch and injector. In Panel A, the patch 7901 includes an adhesive layer 7903 and a sensor 7905, which may comprise the PCB chip. The sensor 7905 may adhere to the adhesive layer 7903, which may be used to secure the patch 7901 to the body of the subject. The injector 7907 and the patch 7901 can be configured so that the patch is applied to the body of the subject as the injector 7907 is attached. Alternatively, or in addition to, the injector 7907 and the patch 7901 may be coupled prior to securing the patch 7901 and injector 7907 to the body of the subject, as shown in panel B. The patch 7901 may be coupled to the injector 7907 via flanges 7913 on the patch and complementary protrusions 7911 on the injector 7907. The flange 7913 may latch or hook onto the protrusions 7911. The flange 7913 can be locked in a first configuration and in a second configuration, the flange 7913 may be released, such as to allow decoupling of the patch 7901 from the injector 7907.

Figure 80:
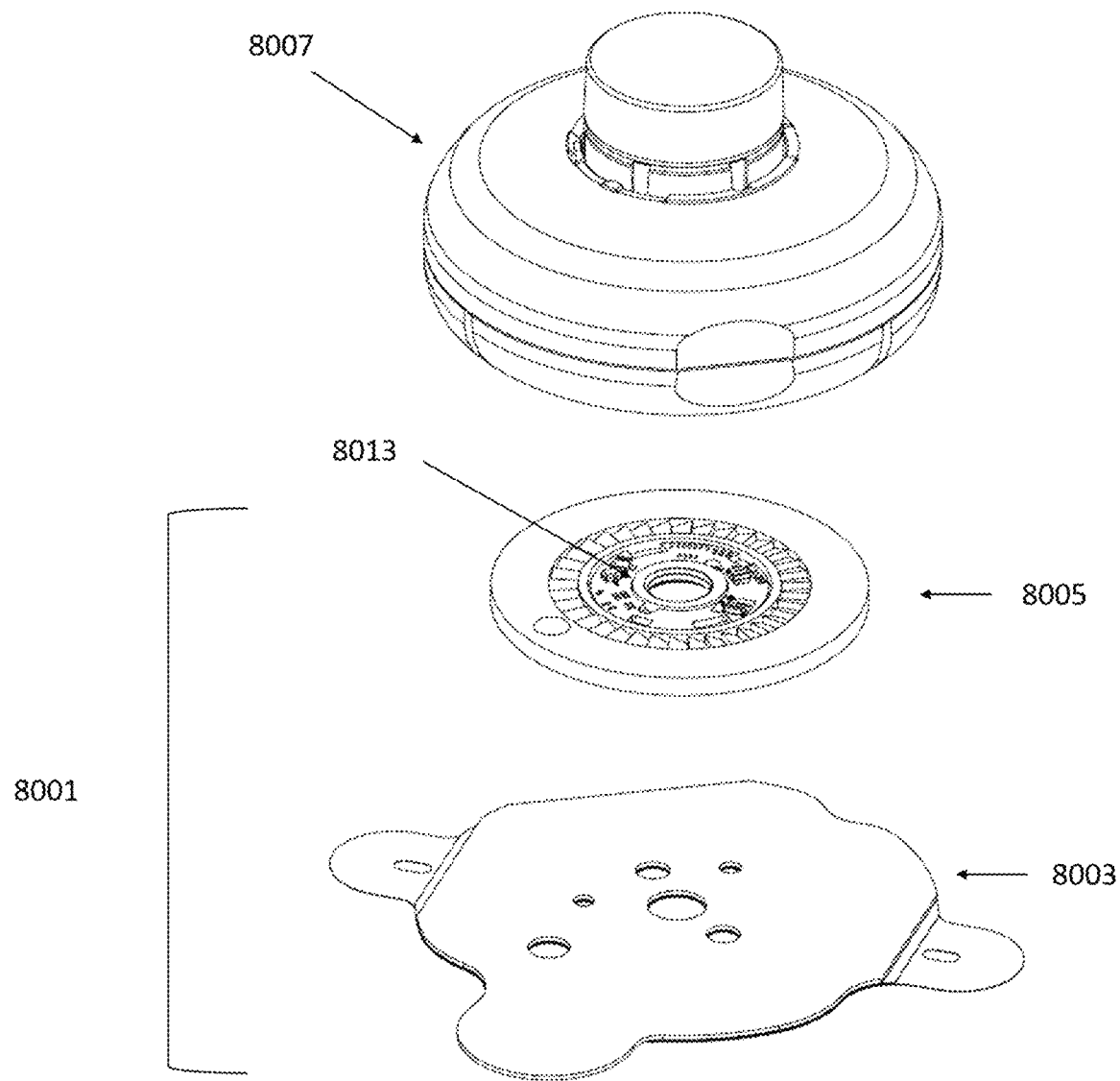
FIG. 80 shows a schematic of another example of an injector coupled to a patch.

FIG. 80 illustrates another embodiment of the patch and injector. The patch 8001 includes an adhesive layer 8003 and a sensor 8005, which may comprise the PCB chip. The sensor 8005 may adhere to the adhesive layer 8003, which may be used to secure the patch 8001 to the body of the subject. The injector 8007 and the patch 8001 can be configured so that the patch is applied to the body of the subject as the injector 8007 is attached. Alternatively, or in addition to, the injector 8007 and the patch 8001 may be coupled prior to securing the patch 8001 and injector 8007 to the body of the subject. The patch 8001 may be coupled to the injector 8007 via thread features 8013 on the patch 8001 and complementary threads (not shown) on the injector 8007. The thread features 8013 may screw onto the complementary threads of the injector 8007. Coupling and decoupling of the patch 8001 to the injector 8007 can occur by twisting the patch 8001 or injector 8007.

Figure 81:
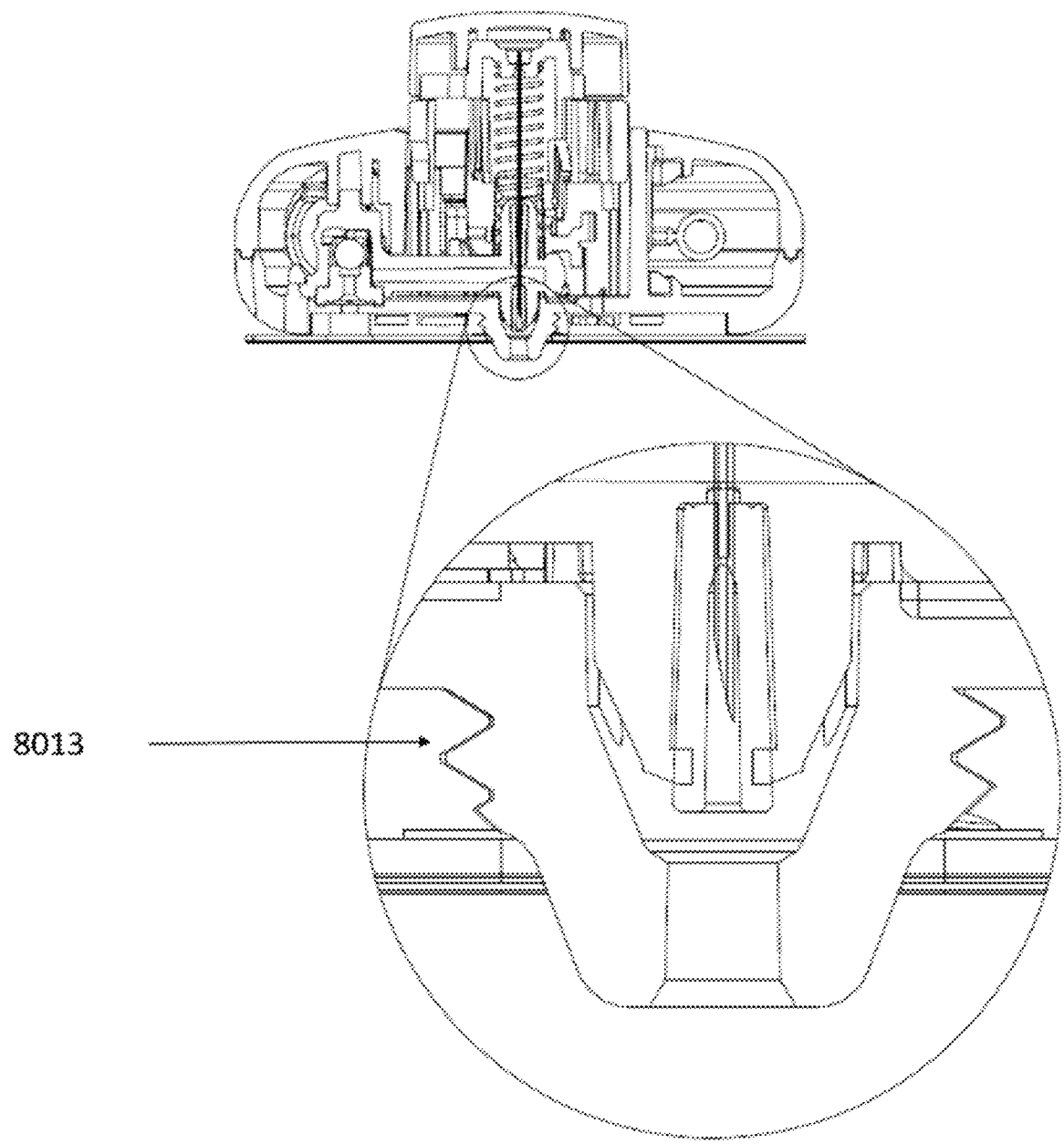
FIG. 81 shows a cross-sectional view of the patch and injector of FIG. 80.

FIG. 81 shows a cross-sectional view of the coupled injector and patch of FIG. 80. The threads 8013 of the patch may be complementary to threads of the injector. Upon twisting of the injector counterclockwise, the patch may be released from the injector.

Figure 82:
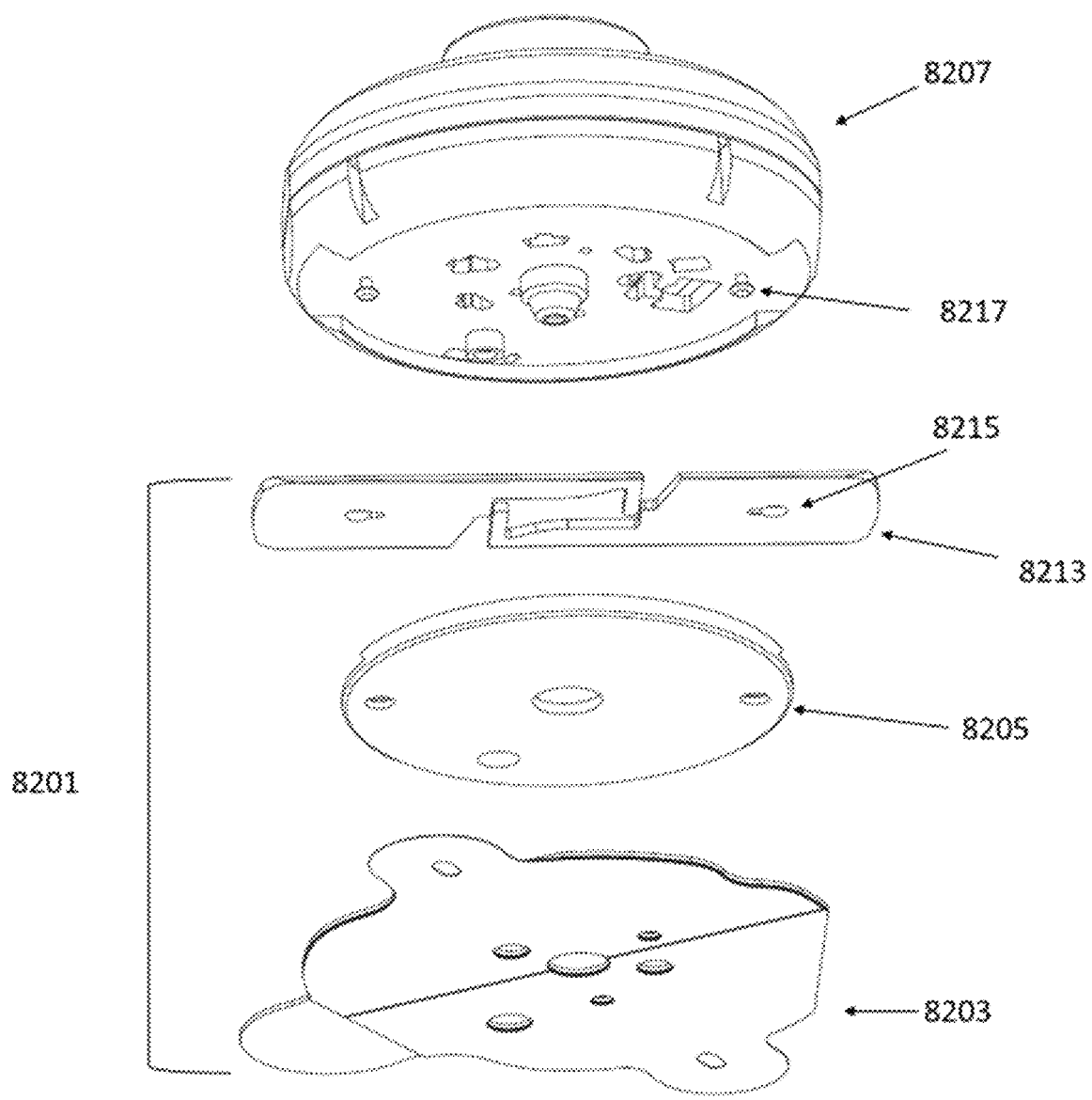
FIG. 82 shows a schematic of another example of an injector coupled to a patch.

FIG. 82 illustrates another embodiment of the patch and injector. The patch 8201 includes an adhesive layer 8203, a sensor 8205, which may comprise the PCB chip, and a deformable surface 8213. The sensor 8205 may adhere to the adhesive layer 8203, which may be used to secure the patch 8201 to the body of the subject. The injector 8207 and the patch 8201 can be configured so that the patch is applied to the body of the subject as the injector 8207 is attached. Alternatively, or in addition to, the injector 8207 and the patch 8201 may be coupled prior to securing the patch 8201 and injector 8207 to the body of the subject. The patch 8201 may be coupled to the injector 8207 via the deformable surface 8213. In a first configuration, the deformable surface 8213 may comprise gradated holes 8215 that can be used to secured screws or pins 8217 of the injector 8207 to the patch 8201. Upon pressing of the two ends of the deformable surface 8213 toward one another, the deformable surface may assume a second configuration, in which the gradated holes 8215 are large enough such that the screws or pins 8217 may detach from the deformable substrate 8213 of the patch 8201, thereby decoupling the patch 8201 from the injector 8207.

Figure 83:
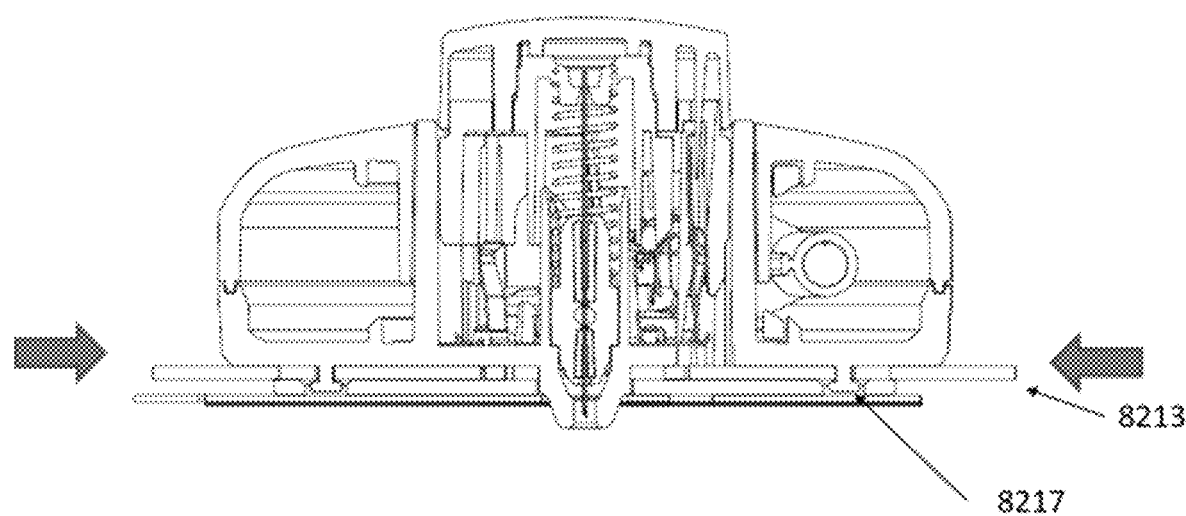
FIG. 83 shows a cross-sectional view of the patch and injector of FIG. 82.

FIG. 83 shows a cross-sectional view of the coupled injector and patch of FIG. 82. In this configuration, the deformable substrate 8213 is locked onto the injector. By pressing the ends of the deformable substrate 8213 together, the gradated holes are moved such that the pins 8217 of the injector may be lifted from the deformable substrate and patch, thereby decoupling the patch from the injector.

Figure 84:
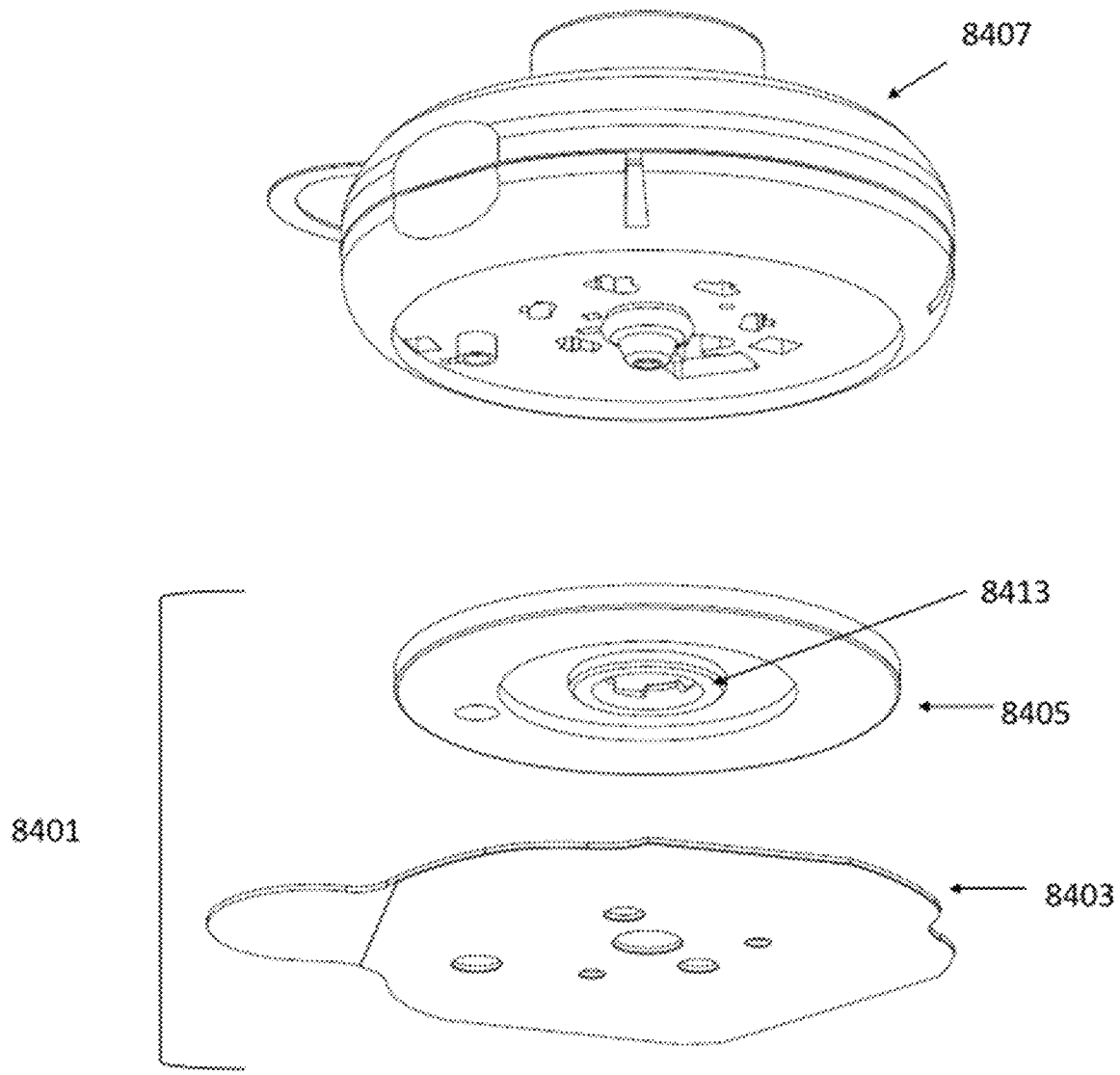
FIG. 84 shows a schematic of another example of an injector coupled to a patch.

FIG. 84 illustrates another embodiment of the patch and injector. The patch 8401 includes an adhesive layer 8403 and a sensor 8405, which may comprise the PCB chip. The sensor 8405 may adhere to the adhesive layer 8403, which may be used to secure the patch 8401 to the body of the subject. The injector 8407 and the patch 8401 can be configured so that the patch is applied to the body of the subject as the injector 8407 is attached. Alternatively, or in addition to, the injector 8407 and the patch 8401 may be coupled prior to securing the patch 8401 and injector 8407 to the body of the subject. The patch 8401 may be coupled to the injector 8407 via ridges 8413 on patch 8401, which may be used to secure the patch 8401 to the injector 8407 via a snap or press fit. The injector 8407 may additionally comprise complementary features that can secure to the ridges 8413. Decoupling of the patch 8401 to the injector 8407 can occur by twisting the patch 8401 or injector 8407 or by pulling apart the patch 8401 from the injector 8407.

Figure 85:
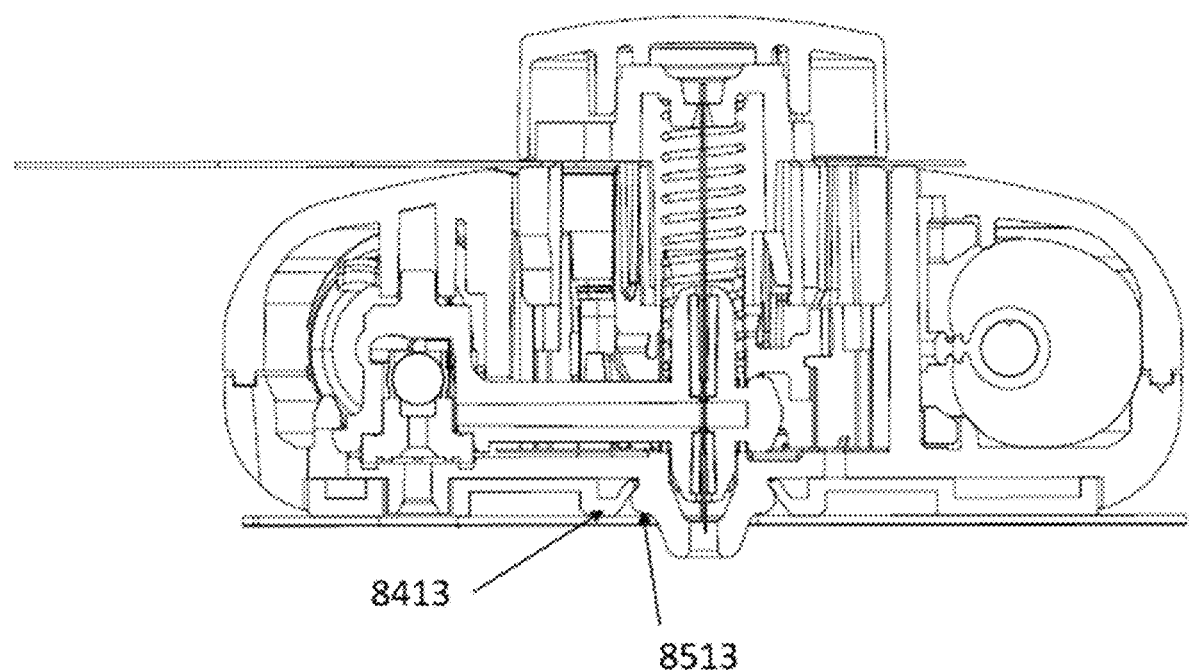
FIG. 85 shows a cross-sectional view of the patch and injector of FIG. 84.

FIG. 85 shows a cross-sectional view of the coupled injector and patch of FIG. 84. The ridges 8413 of the patch may be configured to couple to complementary features 8513 (e.g., bumps, ridges, cavities) of the injector. Decoupling of the patch and injector may occur by applying sufficient force to pry apart the ridges 8413 and complementary features 8513.

FIG. 86 illustrates another embodiment of the patch and injector. The patch 8601 includes an adhesive layer 8603 and a sensor 8605, which may comprise the PCB chip. The sensor 8605 may adhere to the adhesive layer 8603, which may be used to secure the patch 8601 to the body of the subject. The injector 8607 and the patch 8601 can be configured so that the patch is applied to the body of the subject as the injector 8607 is attached. Alternatively, or in addition to, the injector 8607 and the patch 8601 may be coupled prior to securing the patch 8601 and injector 8607 to the body of the subject. The patch 8601 may be coupled to the injector 8607 by coupling or mating parts 8609 and 8611. Part 8609 may be coupled to the injector 8607 (e.g., in a recess 8613) whereas part 8611 may be coupled to the patch 8601. Parts 8609 and 8611 may comprise magnets and may be secured to the recess 8613 of the injector 8607 and the patch 8601 via adhesive, interference fit, or other attachment arrangements.

Figure 87:
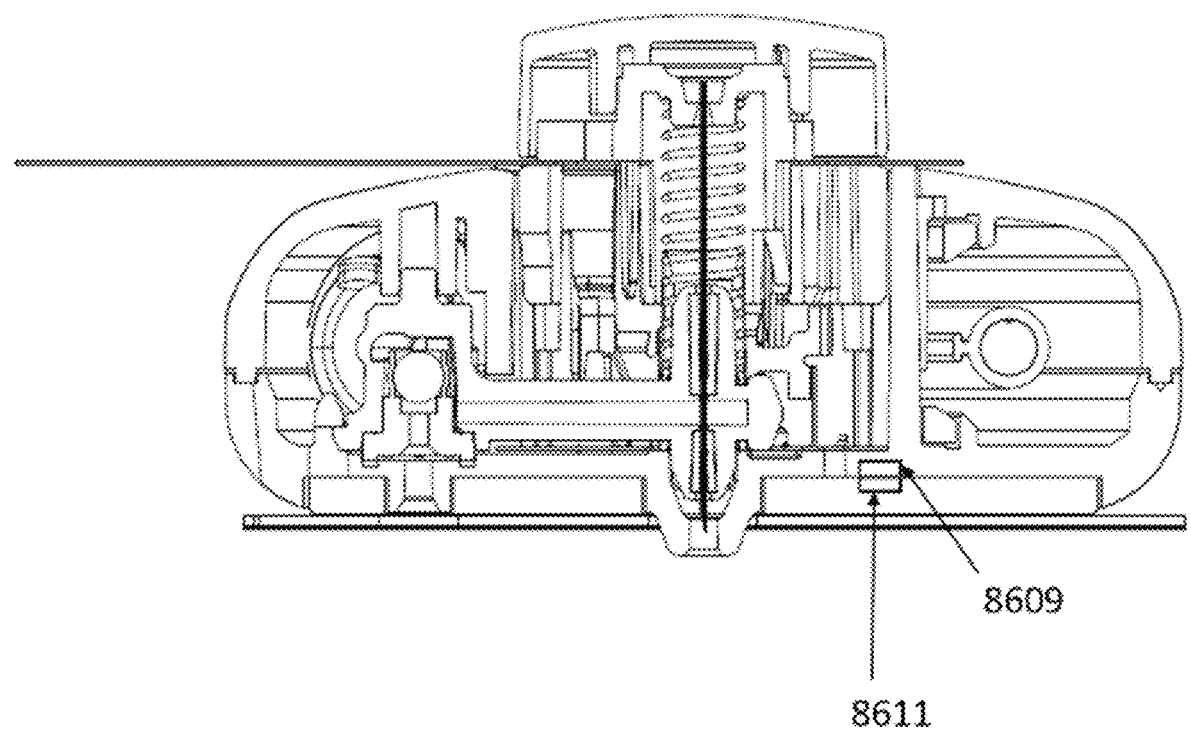
FIG. 87 shows a cross-sectional view of the patch and injector of FIG. 86.

FIG. 87 shows a cross-sectional view of the coupled injector and patch of FIG. 86. The magnets 8611 of the patch may be configured to couple to magnets 8609 of the injector. Decoupling of the patch and injector may occur by applying sufficient separate the magnets of the patch from the magnets of the injector.

In some instances, it may be useful to have both the patch and the injector secured to the body of the subject. In such cases, the injector may additionally comprise features that may be configured to couple the housing of the injector to the body of the subject. For example, the injector may comprise an adhesive layer. The adhesive layer of the injector may be separate from the mechanism used to secure the patch to the body of the subject.

Figure 88:
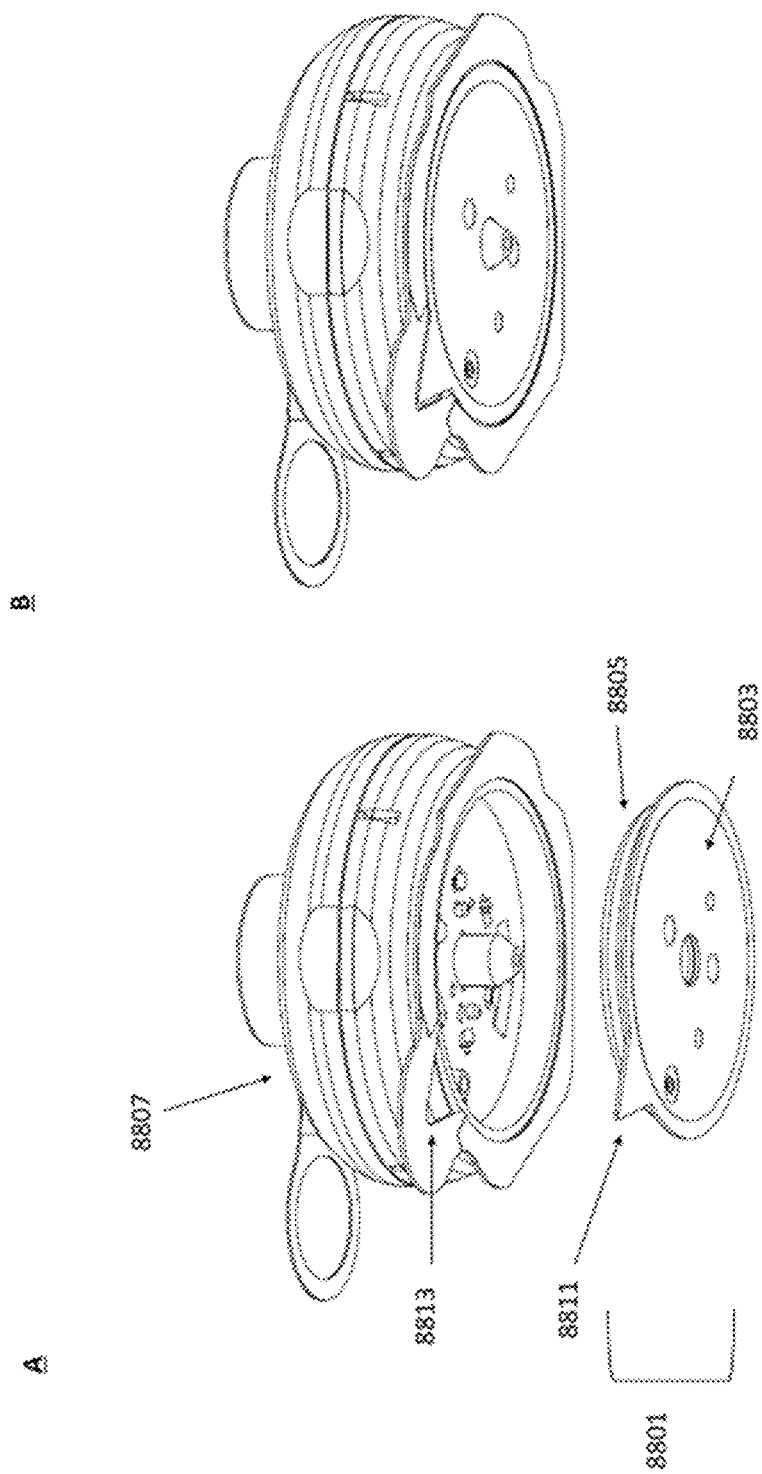
FIG. 88 shows a schematic of another example of an injector coupled to a patch.

FIG. 88 illustrates another embodiment of the patch and injector, where both the patch and injector are configured to couple to the body of the subject. In Panel A the patch 8801 includes an adhesive layer 8803 and a sensor 8805, which may comprise the PCB chip. The sensor 8805 may adhere to the adhesive layer 8803, which may be used to secure the patch 8801 to the body of the subject. The patch 8801 can be configured so that the patch 8801 is applied to the body of the subject, which may be secured separately from the injector 8807, which can also comprise an adhesive layer 8813. Alternatively, or in addition to, the injector 8807 and the patch 8801 may be coupled prior to securing the patch 8801 and injector 8807 to the body of the subject, as shown in Panel B. The patch 8801 may be coupled to the injector 8807 by coupling or mating parts, as described elsewhere herein. The adhesive layer 8803 of the patch 8801 may comprise a feature 8811, which may allow for separation of the adhesive layer 8803 of the patch 8801 from the adhesive layer 8813 of the injector 8807. In such an example, the patch 8801 may be secured to the body of the subject and may not be removable from the subject until the injector 8807 has been removed. In some instances, the attachment or adhesive force of the patch adhesive layer 8803 to the body (e.g., skin) of the subject may be greater than the attachment or adhesive force of the injector 8807 to the body (e.g., skin) of the subject. In some instances, the attachment or adhesive force of the patch adhesive layer 8803 to the body of the subject may be greater than the attachment or adhesive force of the patch 8801 coupled to the injector 8807.

Figure 89:
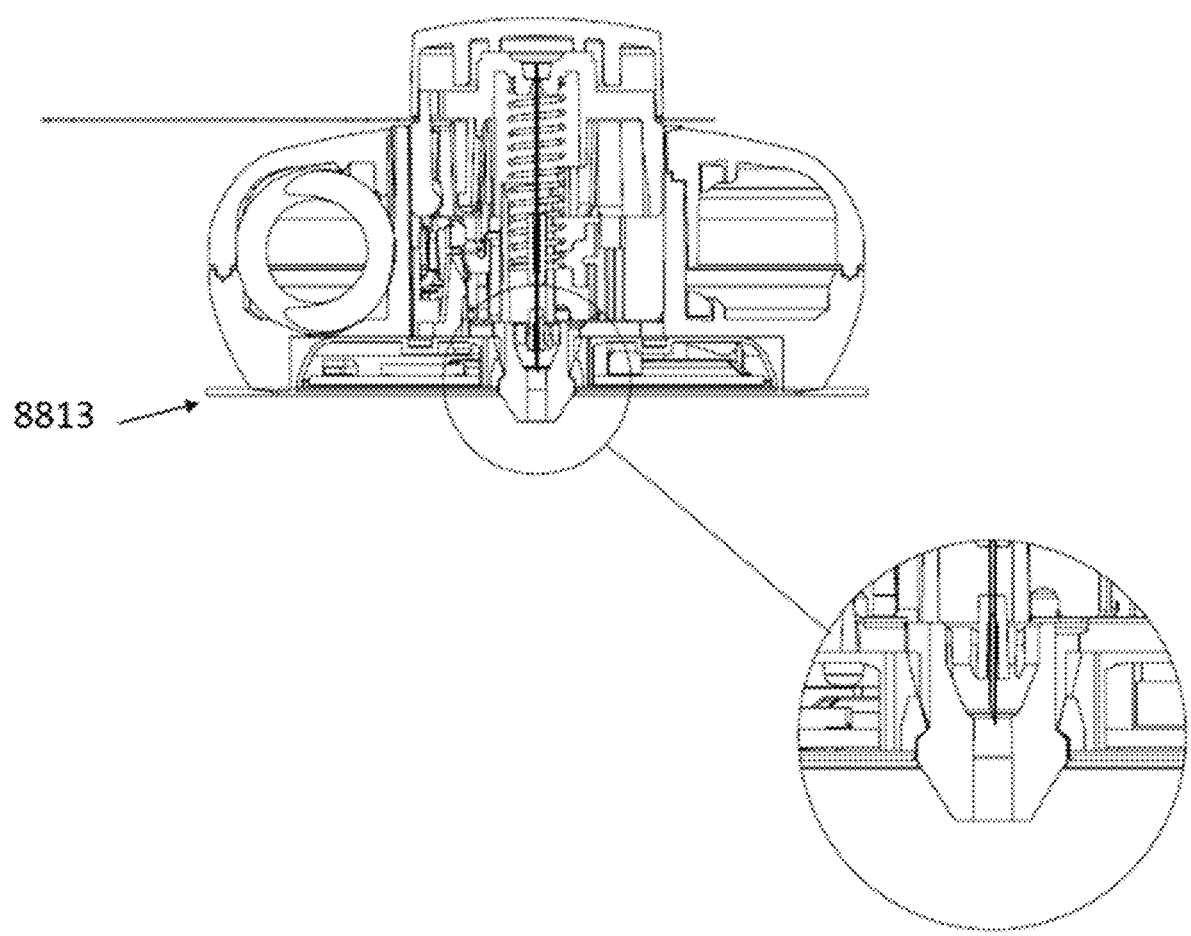
FIG. 89 shows a cross-sectional view of the patch and injector of FIG. 88.

FIG. 89 shows a cross-sectional view of the coupled injector and patch of FIG. 88. Both the patch and the injector may comprise an adhesive layer. The adhesive layer 8813 of the injector may be configured to secure the injector to the body of the subject.

In some cases, the patch or an opening of the patch may comprise a pierce-able membrane. The pierceable membrane may comprise an opening (e.g., slit, hole) through which the cannula of the injector may pass when the cannula is directed from the injector to the body of the subject. In some instances, the pierce-able membrane may adhere or otherwise be secured to the body of the subject. In such cases, the pierce-able membrane may comprise an absorbent material, e.g., to absorb bodily fluids (e.g., blood, sweat, etc.) from the subject. It will be appreciated that any of the above-described embodiments may comprise a patch comprising sensors (e.g., on the PCB chip), and alternatively or in addition to, the patch may comprise the pierce-able membrane, which may comprise an absorbent material.

Figure 90:
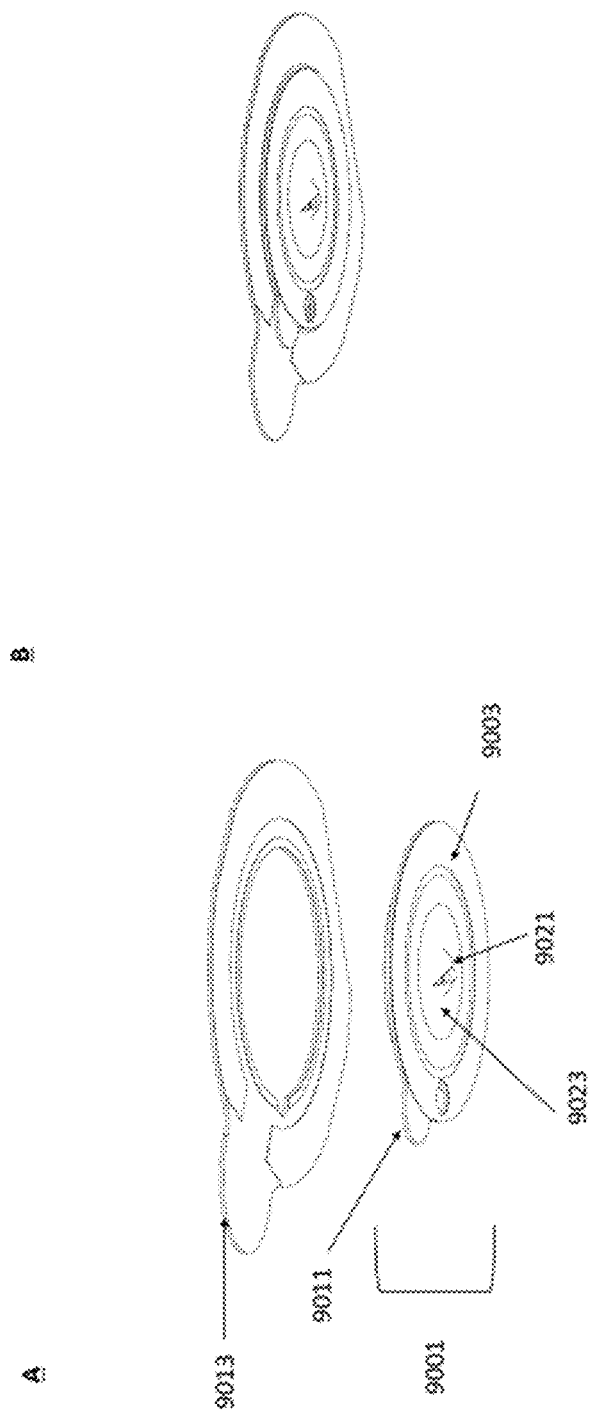
FIG. 90 shows a schematic of an example patch with a pierceable membrane configured to couple to an injector.
Figure 91:
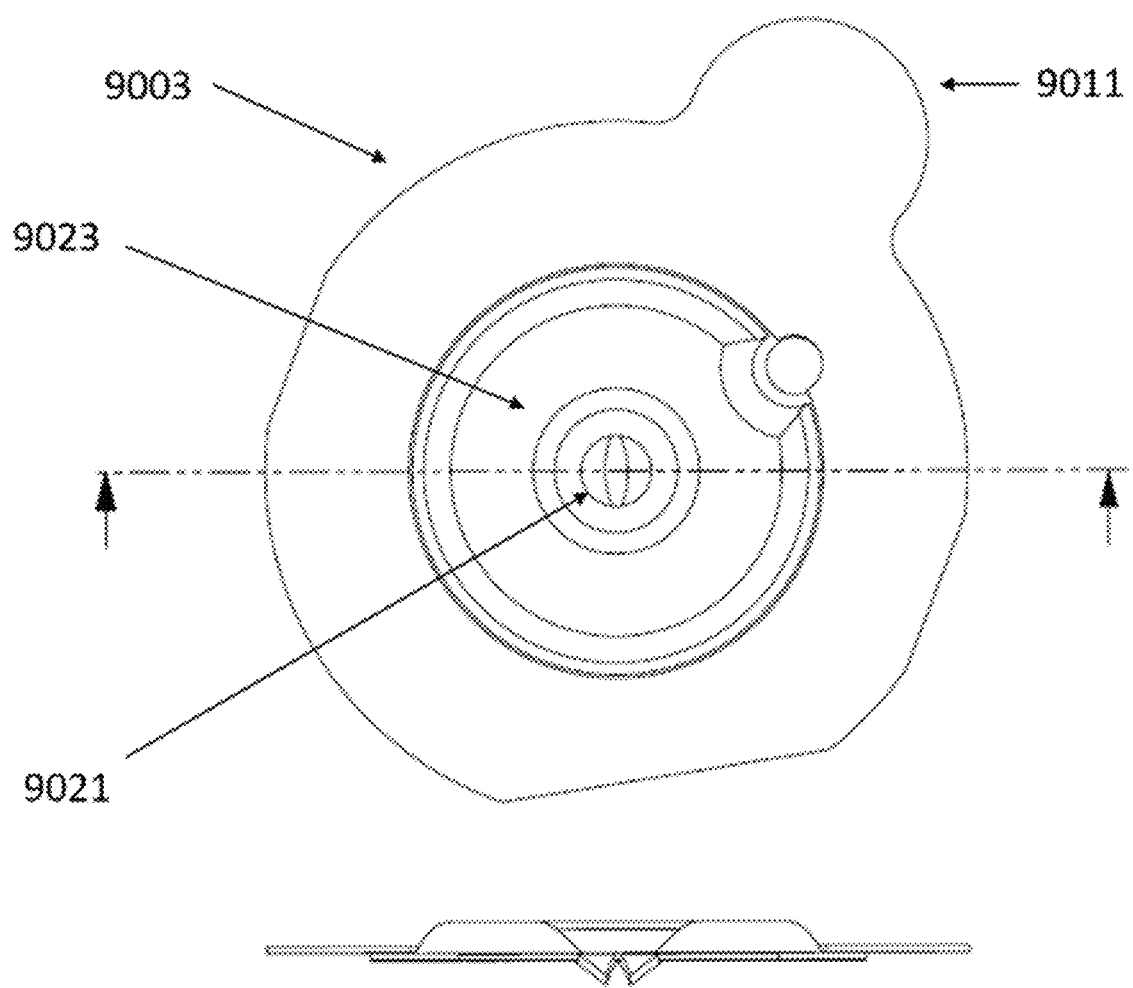
FIG. 91 shows another view of the patch from FIG. 90.

FIG. 90 shows an example patch, or portion thereof, comprising a pierceable membrane coupled to an adhesive layer of an injector. In Panel A the patch 9001 includes an adhesive layer 9003. The patch may also comprise a sensor (not shown) that may adhere to the adhesive layer 9003. The adhesive layer 9003 may be used to secure the patch 9001 to the body of the subject. The patch 9001 can be configured so that the patch 9001 is applied to the body of the subject, which may be secured separately from the injector 9007, which can also comprise an adhesive layer 9013. Alternatively, or in addition to, the injector (not shown) and the patch 9001 may be coupled prior to securing the patch 9001 and injector to the body of the subject, as shown in Panel B. The patch may also comprise an opening 9021, which may comprise a pierceable membrane 9023. In some cases, the opening 9021 is a slit, and the material of the pierceable membrane 9023 comprises a self-healing elastomer (i.e., the opening closes after the cannula is retracted away from the body of the subject). The adhesive layer 9003 of the patch 9001 may comprise a feature 9011 (e.g., tab), which may allow for separation of the adhesive layer 9003 of the patch 9001 from the adhesive layer 9013 of the injector 9007. FIG. 91 shows a bottom-up and cross-sectional view of the patch of FIG. 90. The patch comprises an opening 9021, which is an opening of a pierceable membrane 9023. In some cases, the opening 9021 is a slit, and the material of the pierceable membrane 9023 comprises a self-healing elastomer and/or absorbent material. The adhesive layer 9003 of the patch may comprise a feature 9011 (e.g., tab), which may allow for separation of the adhesive layer 9003 of the patch from the adhesive layer of the injector.

Figure 92:
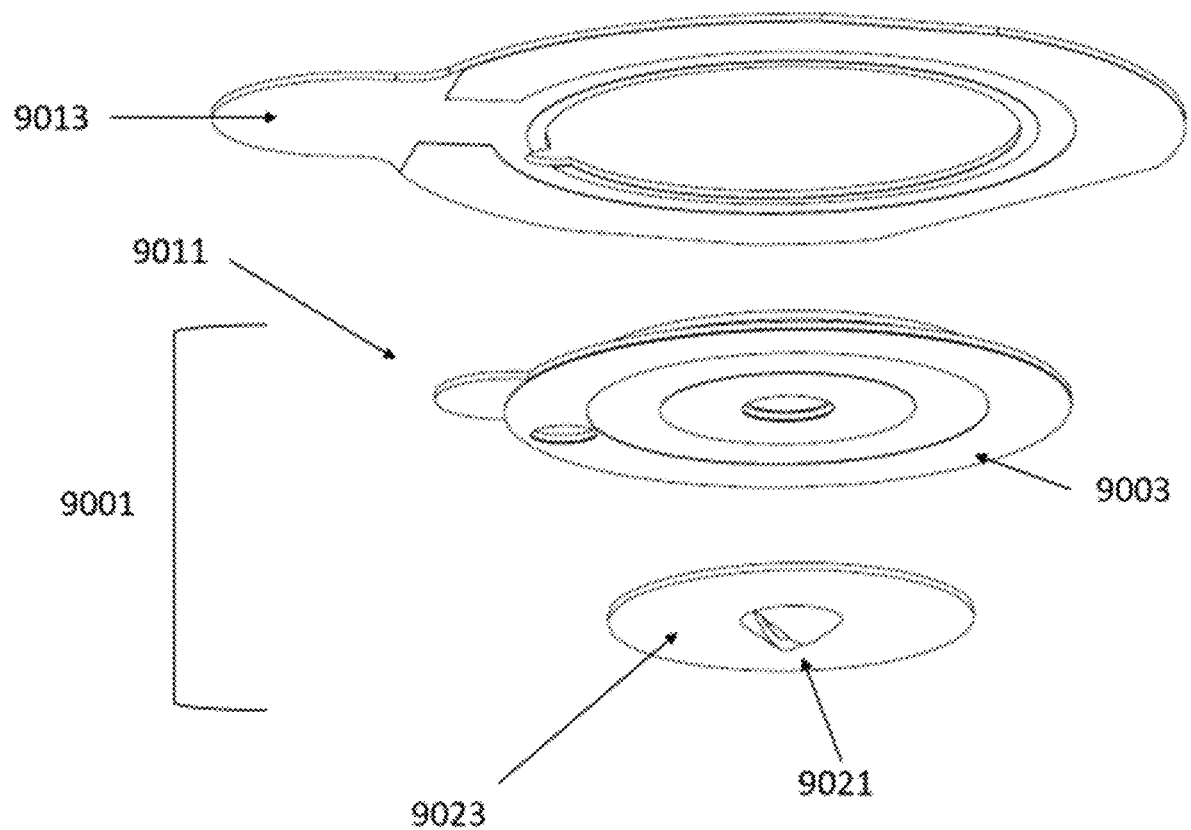
FIG. 92 shows a schematic of another example patch with a pierceable membrane configured to couple to an injector.

FIG. 92 shows an exploded view of the adhesive layers of the patch and injector of FIG. 90. The patch 9001 comprises a pierceable membrane 9023, which can comprise an opening 9021. The pierceable membrane 9023 can be decoupled from the patch and may remain secured to the body of the subject (e.g., as a bandage). In some cases, the opening 9021 is a slit, and the material of the pierceable membrane 9023 comprises a self-healing elastomer as well as absorbent materials. The adhesive layer 9003 of the patch 9001 may comprise a feature 9011 (e.g., tab), which may allow for separation of the adhesive layer 9003 of the patch from the adhesive layer 9013 of the injector.

In some examples, the patch may be configured to couple to an autoinjector. FIG. 93 shows an example patch comprising a pierceable membrane coupled to an autoinjector 9307. In Panel A the patch 9301 includes an adhesive layer 9303. The patch may also comprise a sensor (not shown) that may adhere to the adhesive layer 9303. The adhesive layer 9303 may be used to secure the patch 9301 to the body of the subject, and in some cases, the adhesive layer 9303 may be secured to the body of the subject. In such cases, the adhesive layer 9303 comprises an absorbent material (e.g., bandage pad) and will remain on the body of the subject following injection. The patch 9301 can be configured so that the patch 9301 is applied to the body of the subject, which may be secured separately from the autoinjector

9307. Alternatively, or in addition to, the autoinjector 9307 and the patch 9301 may be coupled prior to securing the patch 9301 to the body of the subject, as shown in Panel B. The patch may also comprise an opening 9321, which may be a part of a pierceable membrane 9323. In some cases, the opening 9321 is a slit, and the material of the pierceable membrane 9323 comprises a self-healing elastomer (i.e., the opening closes after the cannula is retracted away from the body of the subject). The adhesive layer 9303 of the patch 9301 may comprise a feature 9311 (e.g., tab), which may allow for separation of the adhesive layer 9303 of the patch 9301 from the autoinjector. In some instances, the patch 9301 may also comprise a sensor unit 9305, which may comprise a PCB chip.

Embodiments of the disclosure provide a combination of reporting both the injector and the patient state during and after the injection. The patch and associated battery and circuitry are initially physically coupled to the injector. In an alternative embodiment, the patch could be applied and allow for connection of the one or more injectors. The patch circuit can communicate, e.g., via a communication interface, to the receiver the one or more parameters of the injector before being secured to the patient. Once the patch/injector is secured to the patient, the patch communicates both the patient and injector states. When the injector is removed, the patch remains on the patient directly on the injection site to transmit the state of the injection site. The patch could remain there for just a few hours if that is enough time to insure no reaction has occurred, or the patch can remain until the next injector/patch is applied. That is, upon completion of an injection, a patient may remove the injector and keep the patch on. The patch may continue to provide data (up to several days) until the next administration where it is replaced.

There are a number of situations where the physician might be reluctant to let the patient self-administer at home because of potential adverse reactions. If the patch were able to monitor for any potential complications (ISR's, heart rate, respiration, temperature, etc), and transmit a signal to the physician if there was anything unusual, it might give the physician confidence to send the patient home for injections. In an outcome-based healthcare model, there is a significant benefit to the system knowing that the patient is improving with the therapy with quantitative data as evidence. In the instance where the patient's health is acutely changing (or over the long-term), the ability for a treating physician to get involved earlier through notification based on trends of continuously accumulated data and intervene has long term benefit to the patient and overall outcome.

This type of "detachable" monitoring patch can also be extremely useful in clinical studies. The patients could be monitored for a variety of parameters during the study that could increase compliance and reduce complications and could even make enrollment easier. For example, if a patient is required to remain in the physician's office for 4 hours after each injection to monitor for ISR's, they might be able to eliminate this wait with the patch monitoring, which could result in improved recruitment. Moreover, such a device can allow for longitudinal studies that measure patient compliance and that provide for increased accuracy of data transmission (e.g., by obviating the need for manual recording of data).

The patch concept is not limited to the injector described above. This patch with and/or without electronics can also be adapted to other injectors. These devices could include autoinjectors. In view of the above, embodiments of the disclosure may provide, for example, a patch that can include electronics or just comprise a bandage material (see e.g., FIGS. 90-93). In some examples, the patch may be connected to the injector, and securing of the patch and injector may occur via a force applied to the patch and injector, thereby obviating the need for a separate patch application. Alternatively, the patch may be applied by the injector directly to the injection site and may covers the cannula entry point with an expandable/contractible element. As described elsewhere herein, the patch may be magnetically coupled to the injector. In some examples, the patch may be mechanically coupled to the injector with a user-intended release mechanism. In some cases, the patch may be smaller than the total adhesive patch used to adhere the injector. The patch may comprise an adhesive pad that is the same size or smaller than a dimension of the patch. In some examples, the patch may transmit injector data prior to application to the patient, transmit both injector and patient data after application to the patient, and/or transmit patient data after removal of the injector.

Example Applications/Uses

Figure 94:
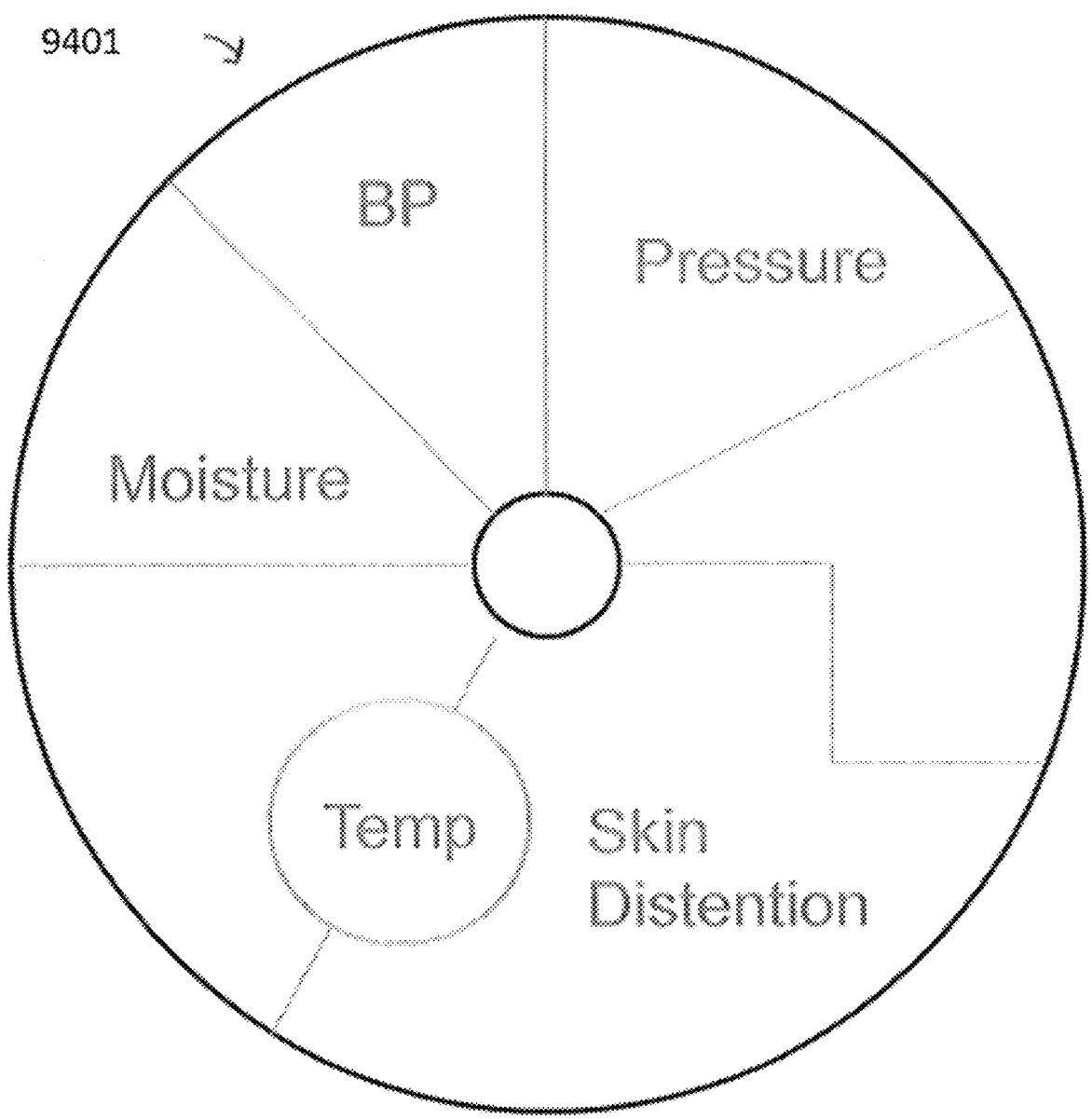
FIG. 94 shows a schematic of an embodiment of a patch sensor of the injector and patch of any of FIGS. 59-93.

As illustrated in FIG. 94, the sensor 9401 of the patch may customized per patient or physician requirements to measure specific device and/or patient attributes or physiological parameters.

One or more sensors may be used to measure the device and/or patient attributes or physiological parameters. Non-limiting examples of types of sensors include temperature sensors, interstitial pressure sensors, skin resistance sensors, skin distention sensors, acoustic sensors, vibration sensors, heart rate sensors, blood pressure sensors (BP in FIG. 94), color or other optical sensors, moisture sensors, chemical sensors (e.g., that sense, measure or detect drug concentration, Histamine, oxygen, etc.).

One or more sensors may be used to measure one or more device attributes, such as the presence of skin, tracking of the delivery of the substance, and/or occlusion of the device (e.g., the cannula of the injector).

Figure 95:
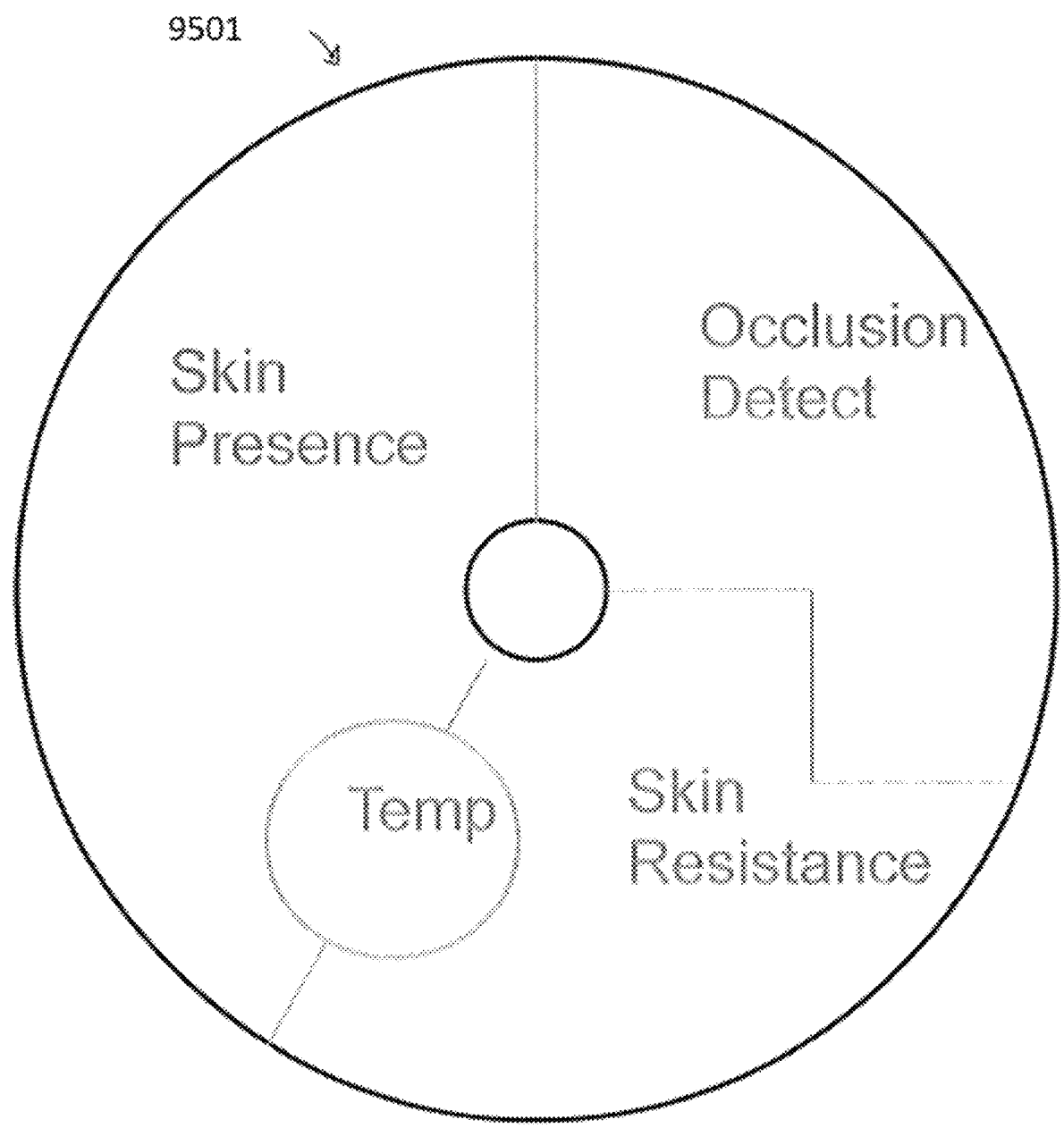
FIG. 95 shows a schematic of the sensor adhesive layer of the patch in an alternative embodiment of the disclosure.

As illustrated in FIG. 95, the sensors may alternatively be incorporated into the sensor adhesive layer 9501. As noted previously, any useful combination of patient sensing attributes may provide for meaningful evidence of conclusions or outcomes. For example: a site reaction may be detected using a temperature measurement, a skin resistance and/or impedance measurement, and a color measurement, or any combination thereof. In another example of correlating pain with measured site reaction, a temperature measurement, a skin resistance or impedance measurement, a color measurement, skin distention measurement, or interstitial pressure measurement, or any combination thereof, may be used. In yet another example of monitoring contraindicated activities during the therapy, a vibration measurement, a heart rate measurement, and/or a moisture measurement (e.g., to indicate sweat levels), or combinations thereof, may be used. In another example, monitoring for wet injection may use a moisture measurement. Another example of subject outcomes may include monitoring for poor bio-absorption by measuring interstitial pressure, tissue density, temperature, skin resistance/impedance, color, and/or skin distention. In another example of monitoring for systemic adverse reaction, a moisture (sweat) measurement, EMG/ECG, vibration (e.g., a proxy for restlessness), increased sound (e.g., as a proxy for stomach or intestine gas levels) may be used, or any combination thereof.

Figure 96:
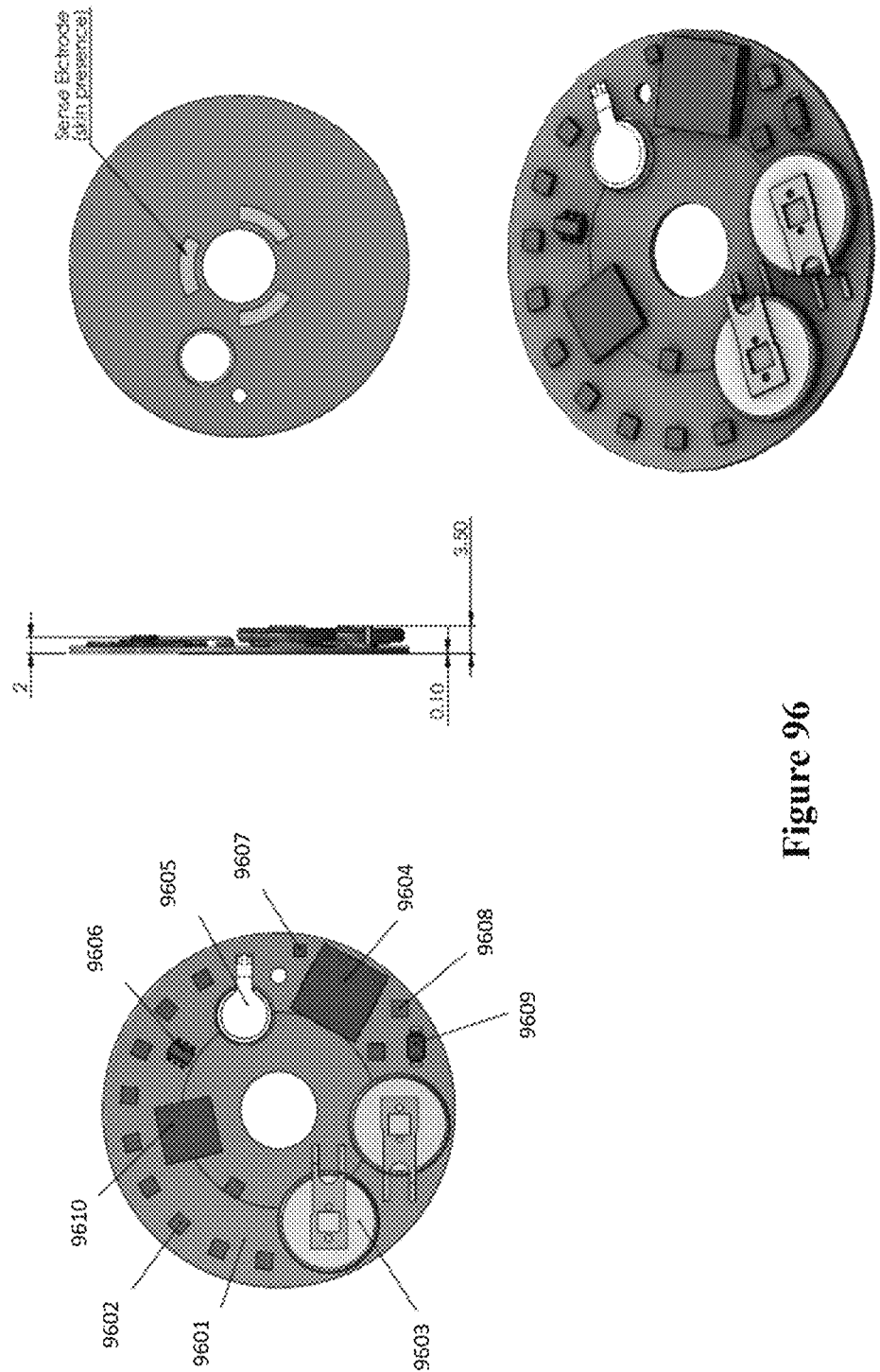
FIG. 96 shows a schematic of sensor adhesive layers of the patch in an embodiment of the present disclosure.

FIG. 96 shows another embodiment of the sensor unit. The sensor unit may comprise, for instance, a PCB 9601, a Hall effect sensor 9602, a coin cell battery 9603, a buzzer 9604, a haptic vibration sensor 9605, a skin presence sensor

9606, a humidity and temperature sensor 9607, a 3D accelerometer and gyroscope 9608, a Reed switch 9609 and a low-power core processor 9610-. The sensor may comprise more than one layer, with different sensors, batteries, and other components distributed in each layer or in distinct layers.

The patch may be used post-injection, after injector removal, for a variety of functions. In non-limiting examples, the patch may be used to close up the injection site to prevent bleeding, use moisture detection to detect any injection site leakage/bleeding, monitor skin temperature and color and pressure to detect ISR's, monitor heartrate/EKG, monitor patient position—upright or recumbent, and/or monitor skin chemistry/sweat.

In some embodiments, the patch can communicate with the patient to remind him or her of the next injection time, provide an alarm if there is injection site reaction or leakage, increase in temperature, color, heartrate etc. Communications between the patch and patient could be visual, audible or tactile.

Embodiments of the patch may be used during an injection to monitor the state of the injector/injector to determine if, for example, the injector is filled, the volume or quantity of the substance (e.g., drug or medicament) that has been filled into the injector, the injector is removed from storage or transfer device base, if the injector is placed on skin, if the safety strip is removed, if the button is pressed, that injection begins, the gas gauge position including delivery tracking, button depressed for pause, the button retracts cannula, injection complete, if the injector is removed from skin, or any of the post-injector parameters associated with measurement of patient physiological parameters previously discussed.

Additional Features/Embodiments

In alternative embodiments, a sensor may detect if another patch is transmitting, or the existing patch was removed. The patch could be clear to allow the patient to see the injection site, and it would be as unobtrusive as possible so the patient could wear the patch and continue to conduct daily activities (shower, swim, etc.).

In further alternative embodiments, sensing elements may be provided that can measure device attributes including: presence of skin (cannula retraction or fall-off sensing), delivery indicator tracking (including fill and dispense), occlusion detection, drug temperature, device status (On/Off Transfer Base, On/Off Patient, Button Status, Pause Events, etc), flowrate, internal injector pressure/injection pressure, adhesive adhesion.

Further embodiments may incorporate patient and device sensing elements to allow for manual and/or automatic intervention (management) on the injector. For example, the flow rate of the injector may be adjusted (e.g., faster, slower, stopped/paused) based on site reaction sensing information (automatic), pain information from patient (manual), bio-absorption rate (automatic) or any combination or variations thereof.

Further embodiments may vibrate (for pain management or notification to user)—Vibration element in injector and/or patch, based on site reaction sensing information, pain information from Patient (manual) or pain sensing information, interstitial pressure/site distention information (automatic), or any combination or variations thereof.

In further embodiments, sound may be provided (e.g., for notification and/or information transfer to the user)—Sound element in injector and/or patch and activated based on sensing information from the patient, device sensing elements (occlusion, drug temp, delivery indication, etc.), or combinations or variations thereof.

In further embodiments, visual indicators may be provided (e.g., indication change, for notification and/or information transfer to the user)—LED or equivalent on injector and/or patch and activated based on sensing information from patient, device sensing elements, the position of the retract button—e.g., to detect premature removal/falloff, sensing information from injector (skin sensing, etc.), sensing information from the patient (high pressure, temp, etc.), or combinations or variations thereof.

In further embodiments, a lockout for the injector button depression (e.g., for security or preventing drug mis-use) may be provided and activated based on sensing information from injector (drug temperature, etc.), sensing information from patient (skin sensing, etc.), sensing information from the mobile application (e.g., time since last injection, user authentication), or variations or combinations thereof.

In further embodiments, subcutaneous/transcutaneous electrical neural stimulation (TENS) (e.g., for pain management or bio-absorption) may be provided. In such cases, an electrode element in cannula and/or patch may be activated based on site reaction sensing information, pain information from patient (manual) or pain sensing information, interstitial pressure/site distention information (automatic), or variations or combinations thereof.

Further embodiments may predict remaining injection time based on e.g., sensing flow rate and fill volume, sensing device pressure and back pressure, drug temperature, body temperature, and fill volume.

Potential features of still further embodiments may also include: the patch sensing if another patch has been applied, the patch being clear to allow visualization of the tissue below, the patch communicating directly with the user/patient, audible signals (e.g., "hey—time for your next injection" or "Call the doctor—you have an ISR"), and/or other tactile options, vibration, electrical stimulation, visual options, light emitting diodes, of the patch regularly transmitting data to receiver or directly to the cloud or intermittent data broadcasting.

Mobile Applications

In another aspect, disclosed herein are systems and methods for generating mobile applications for monitoring one or more health or physiological parameters. A mobile application may be generated using a variety of methods, e.g., an application programming interface (API). The mobile application may comprise a plurality of useful features and may be configured to interact with other mobile applications. In some cases, the mobile application may be configured to display the measurements of one or more physiological parameters from the subject or a parameter of the patch and/or injector. The mobile application may comprise feedback systems that allow for subject or other user input, which may allow for modulation of the patch and/or injector (e.g., amount of substance dispensed). The mobile application may also communicate, e.g., through the communication interface, with a remote server. In some cases, the remote server may be a part of or communicate with a separate electronic device (e.g., mobile device, laptop), which may allow for a clinician or physician to monitor the physiological parameters of the subject. In some cases, the mobile application may allow for inputs from the subject of non-measurable parameters (e.g., pain, discomfort, etc.). The mobile application may also comprise software for data processing. Data processing may include, in non-limiting examples, statistical analysis of data, trend plotting and analysis, and graphical representation of the data. In some cases, the mobile application may be capable of interfacing or combining with other mobile applications, such as a lifestyle tracking application (e.g., to monitor diet and activity), or other useful mobile applications, e.g., location tracking, accelerometer, calendars (e.g., to send reminders), etc.

FIG. 97 illustrates schematically an example workflow of a mobile application for monitoring one or more health or physiological parameters. A mobile device 9700 may be a laptop, a tablet, a phone, or other electronic device (e.g., portable electronic device). Upon opening or selection of the application on the mobile device 9700, a loading screen 9710 may be presented, followed by a menu screen 9720. The menu screen 9720 may provide a plurality of functions 9730. Non-limiting examples of functions 9730 may include starting a new infusion, infusion history, training videos, additional information, and patient profile. Upon selection of a function 9730 (e.g., infusion history), a second screen 9740 pertaining to the function may be presented. In such an example, the subject may be presented with a calendar. In process 9750, the subject may select a second function on the second screen 9740 which presents a third screen 9760. The third screen may display one or more health or physiological parameters of the subject, the device, or the delivery of the substance to the subject (e.g., prescription, time, day of week, regiment, reminders to the patient, alarms, vibrations, etc.). In an example third screen 9980, the calendar may comprise selectable dates that provide information on the one or more health or physiological parameters of the subject on each selected date. In an example fourth screen 9990, the calendar of the mobile application may display additional information, e.g., when the subject has missed an infusion. In an example fifth screen 9790, the calendar of the mobile application may display additional information, e.g., when the subject has received an infusion.

Figure 98:
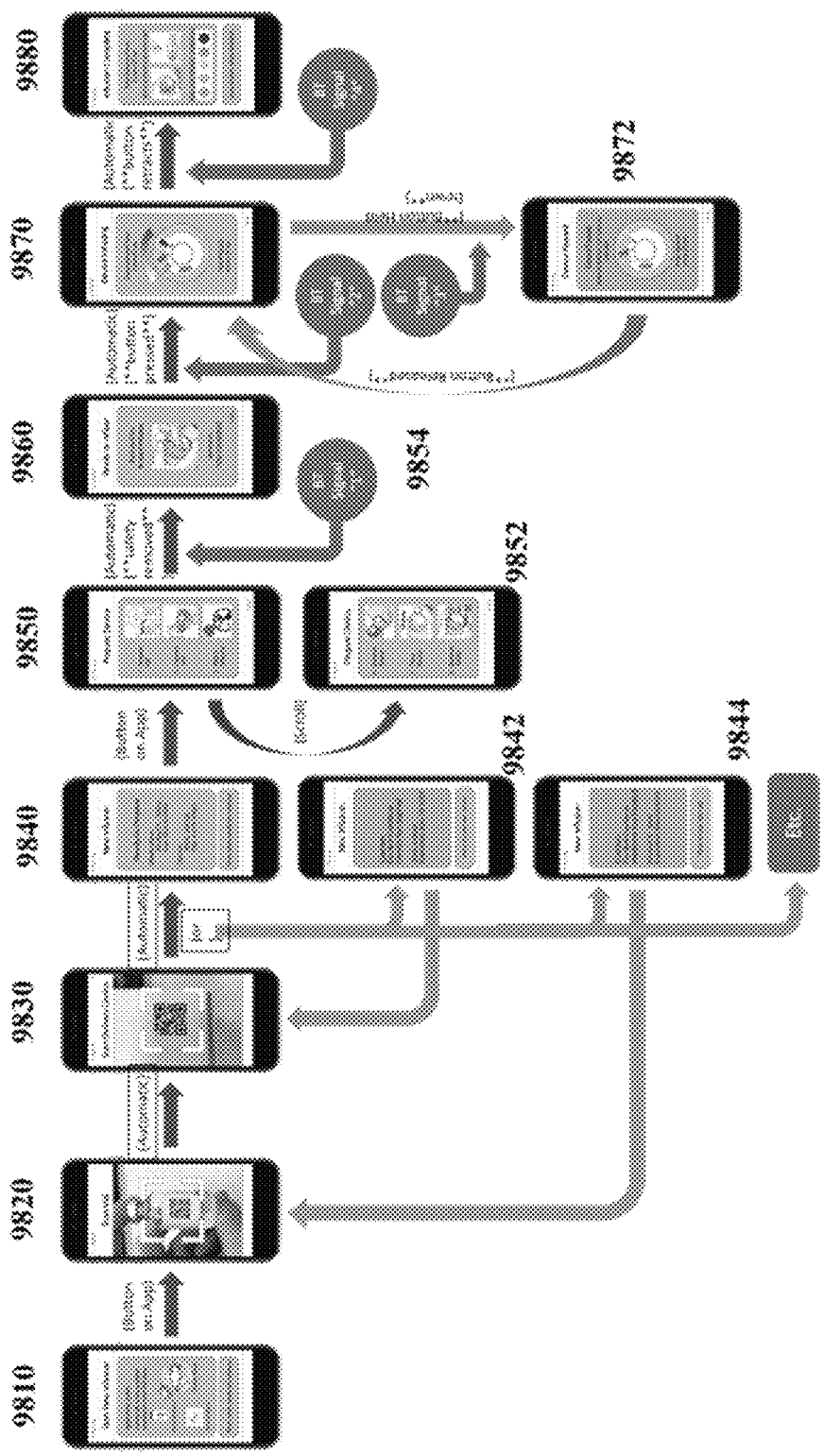
FIG. 98 schematically illustrates another example workflow of a mobile application.

FIG. 98 illustrates schematically an example workflow of a mobile application for monitoring one or more health or physiological parameters, which may be used in conjunction with one or more workflows of the mobile application. Upon selection of a function 9730 (e.g., starting a new infusion, see FIG. 97) from the menu screen 9720 (see FIG. 97), screen 9810 may appear. The mobile application may allow for detection of the substance or medicament, e.g., scanning of a barcode or quick response code (QR code). The mobile application may be integrated with another application on the mobile device such as a camera and display the camera on screen 9820. Screen 9830 shows an example screen of a scanned QR code, which may present information on the substance or device. The mobile application may subsequently verify the drug and device compatibility and/or other parameters of the drug/device, e.g., expiration date, dosage, etc. In cases where the drug or device is inappropriate for the subject (e.g., expired drug), screens 9842 or 9844 may appear, which notify the subject of the inappropriateness of the drug or device. In cases where the drug or device is appropriate for the subject, screen 9850 may appear, which may provide guidance, instructions, or directions to the subject. Instructions may be presented in a continuous scroll format, as exemplified in screen 9852. The mobile application may then be paired with the device. On example screen 9860, additional guidelines may be provided to the subject. Safety features may be included in the application, e.g., if a safety measure (e.g., safety tab) has not been performed by the subject, the mobile application may notify the subject. Screen 9870 may display one or more device parameters (e.g., infusion status, injection of the cannula into the body of the subject, etc.). Incomplete infusion may present screen 9872 which may indicate the status of the infusion and may include other indications of the device parameters (e.g., "device paused"). Upon completion of the delivery of the substance or drug, screen 9880 may be displayed, which may indicate the status of the infusion. In some cases 9880 may present the subject with options to rank the infusion experience. Multiple steps in the process may also comprise communication steps 9854 (e.g., via Bluetooth, Wi-Fi) to a separate device, cloud computing, clinician server, etc.

FIG. 99 illustrates another example workflow of a mobile application for monitoring one or more health or physiological parameters, which may be used in conjunction with one or more workflows of the mobile application. Upon selection of a function 9730 (e.g., training videos, see FIG. 97) from the menu screen 9720 (see FIG. 97), screen 9900 may appear. The mobile application may comprise a variety of tutorials or training information for the subject. FIG. 99A demonstrates schematically a plurality of devices or systems which may be integrated with the mobile application. Upon selection of a device or system (e.g., syringe transfer system, handheld system, vial transfer system, reconstitution system), screens 9905, 9910, 9915, or 9920 may appear, which may comprise a video demonstrating a tutorial or method of use of the device or system. FIG. 99B illustrates schematically another example workflow of a mobile application for monitoring one or more health or physiological parameters, which may be used in conjunction with one or more workflows of the mobile application. Upon selection of a function 9730 (e.g., additional information, see FIG. 97) from the menu screen 9720 (see FIG. 97), screen 9925 may appear, which may comprise a menu displaying one or more health of physiological parameters or one or more device parameters. Additional information may be available to the subject (e.g., prescription information, device information, etc.). Upon selection of a function in the menu, screen 9930 or 9945 may appear, which may further comprise options to display additional information, e.g., safety information (e.g., screen 9935 or 9950) or questions and answers (e.g., screen 9940 or 9955). FIG. 99C illustrates schematically another example workflow of a mobile application for monitoring one or more health or physiological parameters, which may be used in conjunction with one or more workflows of the mobile application. Upon selection of a function 9730 (e.g., patient profile, see FIG. 97) from the menu screen 9720 (see FIG. 97), screen 9970 may appear, which may comprise a menu. The menu may include options for the subject to view and/or input patient information (e.g., gender, height, weight, activity level). Additional settings may be implemented in the mobile application, such as alarms, alerts, emails, notifications, etc.

Computer Systems

Figure 100:
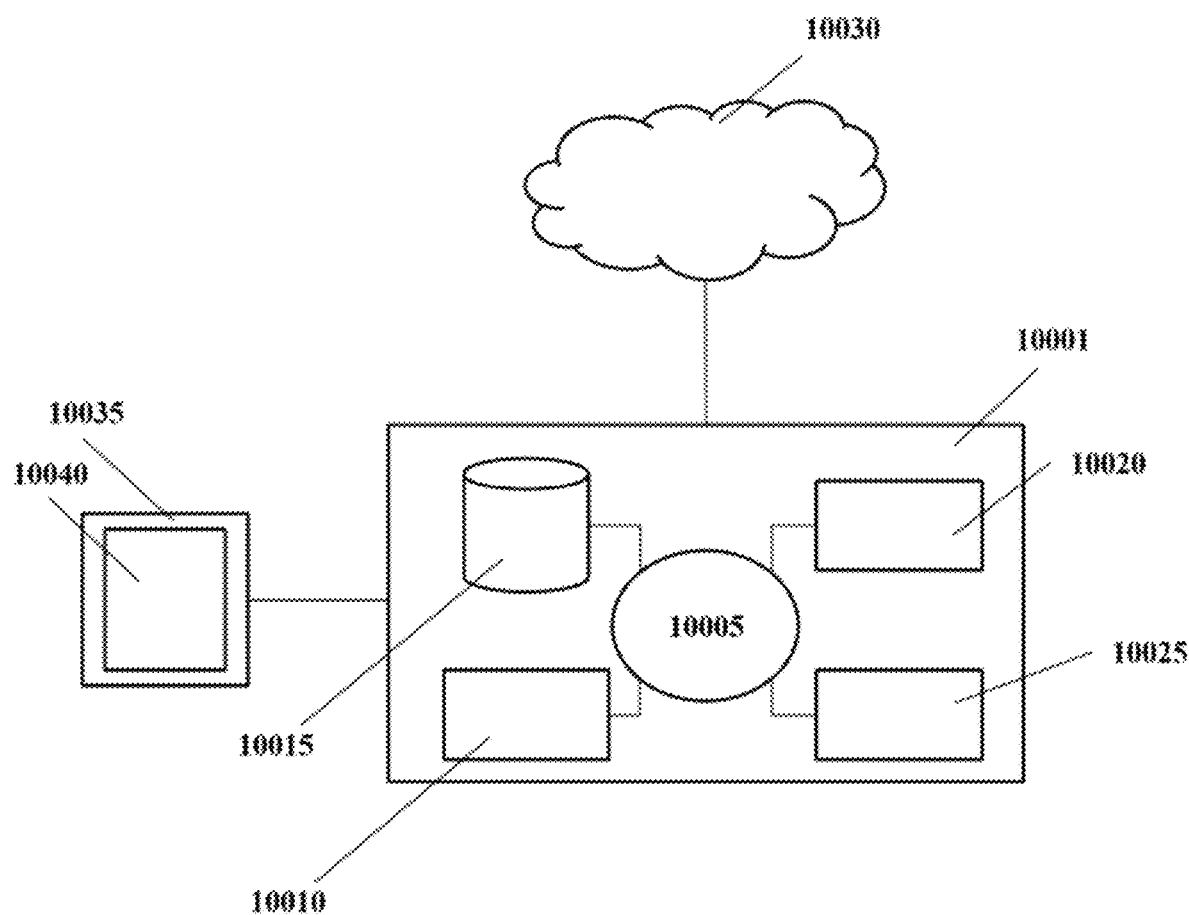
FIG. 100 shows a computer system that is programmed or otherwise configured to implement methods provided herein.

The present disclosure provides computer systems that are programmed to implement methods of the disclosure. FIG. 100 shows a computer system 10001 that is programmed or otherwise configured to transmit and/or receive data, and process data. The computer system 10001 can regulate various aspects of the present disclosure, such as, for example, methods for data analysis, subject monitoring and measurement of physiological or health parameters, and providing an output of the physiological or health parameters. The computer system 10001 can be an electronic device of a user or a computer system that is remotely located with respect to the electronic device. The electronic device can be a mobile electronic device.

The computer system 10001 includes a central processing unit (CPU, also "processor" and "computer processor"

herein) 10005, which can be a single core or multi core processor, or a plurality of processors for parallel processing. The computer system 10001 also includes memory or memory location 10010 (e.g., random-access memory, read-only memory, flash memory), electronic storage unit 10015 (e.g., hard disk), communication interface 10020 (e.g., network adapter) for communicating with one or more other systems, and peripheral devices 10025, such as cache, other memory, data storage and/or electronic display adapters. The memory 10010, storage unit 10015, interface 10020 and peripheral devices 10025 are in communication with the CPU 10005 through a communication bus (solid lines), such as a motherboard. The storage unit 10015 can be a data storage unit (or data repository) for storing data. The computer system 10001 can be operatively coupled to a computer network ("network") 10030 with the aid of the communication interface 10020. The network 10030 can be the Internet, an internet and/or extranet, or an intranet and/or extranet that is in communication with the Internet. The network 10030 in some cases is a telecommunication and/or data network. The network 10030 can include one or more computer servers, which can enable distributed computing, such as cloud computing. The network 10030, in some cases with the aid of the computer system 10001, can implement a peer-to-peer network, which may enable devices coupled to the computer system 10001 to behave as a client or a server.

The CPU 10005 can execute a sequence of machine-readable instructions, which can be embodied in a program or software. The instructions may be stored in a memory location, such as the memory 10010. The instructions can be directed to the CPU 10005, which can subsequently program or otherwise configure the CPU 10005 to implement methods of the present disclosure. Examples of operations performed by the CPU 10005 can include fetch, decode, execute, and writeback.

The CPU 10005 can be part of a circuit, such as an integrated circuit. One or more other components of the system 10001 can be included in the circuit. In some cases, the circuit is an application specific integrated circuit (ASIC).

The storage unit 10015 can store files, such as drivers, libraries and saved programs. The storage unit 10015 can store user data, e.g., user preferences and user programs. The computer system 10001 in some cases can include one or more additional data storage units that are external to the computer system 10001, such as located on a remote server that is in communication with the computer system 10001 through an intranet or the Internet.

The computer system 10001 can communicate with one or more remote computer systems through the network 10030. For instance, the computer system 10001 can communicate with a remote computer system of a user (e.g., Located at a physician's office or a physician's mobile device). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 10001 via the network 10030.

Methods as described herein can be implemented by way of machine (e.g., computer processor) executable code stored on an electronic storage location of the computer system 10001, such as, for example, on the memory 10010 or electronic storage unit 10015. The machine executable or machine-readable code can be provided in the form of software. During use, the code can be executed by the processor 10005. In some cases, the code can be retrieved from the storage unit 10015 and stored on the memory 10010 for ready access by the processor 10005. In some situations, the electronic storage unit 10015 can be precluded, and machine-executable instructions are stored on memory 10010.

The code can be pre-compiled and configured for use with a machine having a processer adapted to execute the code or can be compiled during runtime. The code can be supplied in a programming language that can be selected to enable the code to execute in a pre-compiled or as-compiled fashion.

Aspects of the systems and methods provided herein, such as the computer system 10001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 10001 can include or be in communication with an electronic display 10035 that comprises a user interface (UI) 10040. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 10005. The algorithm can, for example, process data, perform statistical analyses, plot or graphically represent data, and provide feedback for one or more systems disclosed herein (e.g., the patch and/or injector).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for measuring a health or physiological parameter from a subject, comprising:
   (a) providing (i) a patch comprising a first housing comprising a sensor, and (ii) an injector comprising a second housing, wherein said second housing encases a cannula, a fluid flow path, and a reservoir comprising a substance, wherein said cannula is in fluid communication with said fluid flow path, and wherein said fluid flow path is in fluid communication with said reservoir, wherein said first housing and said second housing are in a locked configuration such that said patch remains attached to said injector;
   (b) securing said patch to a body of said subject;
   (c) with said patch secured to said body of said subject, directing said cannula through an opening and into said body of said subject;
   (d) subsequent to (c), (i) directing said substance from said reservoir to said fluid flow path, and (ii) directing said substance from said fluid flow path into said subject through said cannula, wherein subsequent to directing said substance into said subject, said first housing and said second housing are in an unlocked configuration such that said injector is removable from said patch;
   (e) removing said injector from said patch to leave said patch secured to said body of said subject; and
   (f) subsequent to (e), using said sensor to (i) measure said health or physiological parameter from said subject, and (ii) provide one or more outputs corresponding to said health or physiological parameter from said subject.

2. The method of claim 1, further comprising using a pump integrated with said cannula to direct said substance from said fluid flow path into said subject through said cannula.

3. The method of claim 1, wherein in (c), said cannula extends towards said body of said subject.

4. The method of claim 1, wherein said patch comprises a pierceable membrane, wherein said pierceable membrane is pierced by said cannula to generate said opening.

5. The method of claim 4, wherein said pierceable membrane comprises an absorbent material.

6. The method of claim 1, wherein said reservoir is secured to said injector.

7. The method of claim 6, wherein said reservoir is removable from said injector.

8. The method of claim 6, wherein said reservoir is part of said injector.

9. The method of claim 1, wherein said substance is a medicament.

10. The method of claim 9, wherein said medicament is for treating one or more diseases selected from the group of a cardiovascular disease, musculoskeletal disease, gastrointestinal disease, dermatological disease, immunological disease, ophthalmological disease, hematological disease, neurological disease, cancer, endocrinological disease, metabolic disease, and respiratory disease.

11. The method of claim 1, wherein said reservoir contains a formulation comprising said substance.

12. The method of claim 1, wherein said patch comprises a communication interface for transmitting data corresponding to said health or physiological parameter to an electronic device in communication with said communication interface.

13. The method of claim 12, wherein said communication interface comprises a wireless communication interface.

14. The method of claim 13, wherein said wireless communication interface is a near field communication interface, a Bluetooth interface, a WiFi interface, or an optical wireless interface.

15. The method of claim 12, wherein said communication interface comprises a wired communication interface.

16. The method of claim 1, wherein said sensor is selected from the group consisting of a conductivity sensor, impedance sensor, capacitance sensor, charge sensor, humidity sensor, temperature sensor, heart rate sensor, interstitial pressure sensor, resistance sensor, distension sensor, acoustic sensor, vibration sensor, blood pressure sensor, color sensor, chemical sensor, and a substance-tracking sensor.

17. The method of claim 1, wherein said patch or said injector comprises an additional sensor different from said sensor.

18. The method of claim 17, wherein said patch comprises said additional sensor.

19. The method of claim 17, wherein said injector comprises said additional sensor.

20. The method of claim 1, further comprising using said sensor to measure said health or physiological parameter from said subject prior to directing said substance from said fluid flow path into said subject through said cannula.

21. The method of claim 1, wherein said patch further comprises one or more transducers configured to generate an output signal, wherein said output signal comprises a vibration signal, audio signal, electrical signal, or visual signal, or a combination thereof.

22. The method of claim 1, wherein said patch measures a plurality of health or physiologic parameters, including said health or physiologic parameter.

23. The method of claim 1, wherein said patch receives data from said injector.

24. The method of claim 1, wherein said injector is an autoinjector.

25. The method of claim 1, wherein said one or more outputs comprises a signal selected from the group consisting of an audio signal, a vibration signal, an electrical signal, and a visual signal.

26. The method of claim 1, wherein said patch comprises said opening and (c) comprises directing said cannula through said opening of said patch and into said body of said subject.

27. The method of claim 1, wherein said removing of (e) comprises directing said injector away from said body of said subject.

28. The method of claim 1, wherein in (d) said substance is directed into said subject while said injector is secured to said patch at a first location, wherein in (f) said patch is secured to said body of said subject at a second location, and wherein said first location and said second location are substantially the same.

* * * * *